US010344067B2

(12) United States Patent
Ungerechts et al.

(10) Patent No.: US 10,344,067 B2
(45) Date of Patent: Jul. 9, 2019

(54) RNA VIRUSES EXPRESSING IL-12 FOR IMMUNOVIROTHERAPY

(71) Applicants: DEUTSCHES KREBSFORSCHUNGSZENTRUM, Heidelberg (DE); RUPRECHT-KARLS UNIVERSITAET, Heidelberg (DE)

(72) Inventors: Guy Ungerechts, Heidelberg (DE); Christine Engeland, Heidelberg (DE); Ruta Veinalde, Heidelberg (DE)

(73) Assignees: DEUTSCHES KREBSFORSCHUNGSZENTRUM, Heidelberg (DE); RUPRECHT-KARLS UNIVERSITAET, Heidelberg (DE)

(*) Notice: Subject to any disclaimer, the term of this patent is extended or adjusted under 35 U.S.C. 154(b) by 0 days.

(21) Appl. No.: 15/441,545

(22) Filed: Feb. 24, 2017

(65) Prior Publication Data

US 2017/0247425 A1 Aug. 31, 2017

Related U.S. Application Data

(60) Provisional application No. 62/299,788, filed on Feb. 25, 2016.

(51) Int. Cl.

| | |
|---|---|
| ***A61K 35/768*** | (2015.01) |
| ***C07K 16/28*** | (2006.01) |
| ***C07K 16/30*** | (2006.01) |
| ***C07K 14/54*** | (2006.01) |
| *A61K 39/00* | (2006.01) |
| *A61K 38/00* | (2006.01) |

(52) U.S. Cl.

CPC ...... *C07K 14/5434* (2013.01); *C07K 16/2818* (2013.01); *C07K 16/2827* (2013.01); *C07K 16/2887* (2013.01); *C07K 16/3007* (2013.01); *A61K 38/00* (2013.01); *A61K 2039/505* (2013.01); *A61K 2039/507* (2013.01); *A61K 2039/5256* (2013.01); *C07K 2317/622* (2013.01); *C12N 2760/18043* (2013.01); *C12N 2760/18432* (2013.01); *C12N 2760/18443* (2013.01)

(58) Field of Classification Search

CPC ....... A61K 35/768; C07K 16/28; C07K 16/30

See application file for complete search history.

(56) References Cited

U.S. PATENT DOCUMENTS

| | | | | |
|---|---|---|---|---|
| 2010/0081796 A1* | 4/2010 | Brinkmann | C07K 16/2863 | 530/387.3 |
| 2014/0370039 A1* | 12/2014 | Medin | A61K 38/208 | 424/185.1 |
| 2015/0250837 A1* | 9/2015 | Nolin | C07K 16/2818 | 424/281.1 |
| 2017/0065650 A1* | 3/2017 | Engeland | C12N 7/00 | |

FOREIGN PATENT DOCUMENTS

| | | | |
|---|---|---|---|
| EP | 0404097 | A2 | 12/1990 |
| WO | 93/01161 | A1 | 1/1993 |
| WO | 2015/128313 | A1 | 9/2015 |

OTHER PUBLICATIONS

Combredet et al., A Molecularly Cloned Schwarz Strain of Measles Virus Vaccine Induces Strong Immune Responses in Macaques and Transgenic Mice Journal of Virology, Nov. 2003, p. 11546-11554.*

Russell et al., Oncolytic virotherapy, 2012, Nature Biotechnology pp. 1-13.*

K. Abiko et al., British Journal of Cancer, 2015, 112, pp. 1501-1509.

Andtbacka et al., J.Clin. Oncol. 2013, 31, suppl. abstract LBA9008.

Current Protocols in Molecular Biology, John Wiley & Sons, N.Y., 1993, 6.3.1-6.3.6.

Da-Fei Feng and Russell F. Doolittle, "Progressive Sequence Alignment as a Prerequisite to Correct Phylogenetic Trees", J. Mol. Evol., 1987, 25, pp. 351-360.

G. Galfre and C. Milstein, "[1] Preparation of Monoclonal Antibodies: Strategies and Procedures", Methods in Enzymology, vol. 73, 1981, pp. 3-46.

Grossardt et al., "Granulocyte-Macrophage Colony-Stimulating Factor-Armed Oncolytic Measles Virus is an Effective Therapeutic Cancer Vaccine", Human Gene Therapy, 2013, 24, pp. 644-654.

Heo et al., "Randomized dose-finding clinical trial of oncolytic immunotherapeutic vaccinia JX-594 in liver cancer", Nat. Med. 2013, 19(3), pp. 329-336.

Desmond G. Higgins and Paul M. Sharp, "Fast and sensitive multiple sequence alignments on a microcomputer", Cabios Communications, 1989, vol. 5, No. 2, pp. 151-153.

Hoffman et al., "Vaccination of Rhesus Macaques with a Recombinant Measles Virus Expressing Interleukin-12 Alters Humoral and Cellular Immune Responses", J. Infectious Diseases, 2003, 188, pp. 1553-1561.

Holliger et al., "Diabodies": Small bivalent and bispecific antibody fragments, Proc. Natl. Acad. Sci., 1993, vol. 90, pp. 6444-6448.

Peter J. Hudson and Christelle Souriau, "Engineered antibodies", Nature Medicine, 2003, vol. 9, No. 1, pp. 129-134.

(Continued)

*Primary Examiner* — Maria G Leavitt

(74) *Attorney, Agent, or Firm* — J.A. Lindeman & Co., PLLC; Sulay Jhaveri; Jeffrey Lindeman

(57) ABSTRACT

The present invention relates to a recombinant virus of the family Paramyxoviridae, comprising at least one expressible polynucleotide encoding an IL-12 polypeptide, wherein said IL-12 polypeptide is an IL-12 fusion polypeptide comprising a p35 subunit of an IL-12 and a p40 subunit of an IL-12; to a polynucleotide encoding the same, and to a kit comprising the same. Moreover, the present invention relates to a method for treating cancer in a subject afflicted with cancer, comprising contacting said subject with a recombinant virus of the family Paramyxoviridae of the invention, and thereby, treating cancer in a subject afflicted with cancer.

7 Claims, 19 Drawing Sheets

Specification includes a Sequence Listing.

(56) References Cited

OTHER PUBLICATIONS

Klevenz et al., "Peptide aptamers: exchange of the thioredoxin-A scaffold by alternative platform proteins and its influence on target protein binding", CMLS, Cell. Mol. Life Sci., 2002, 59, pp. 1993-1998.
G. Koehler and C. Milstein, "Continuous cultures of fused cells secreting antibody of predefined specificity", Nature,1975, vol. 256, pp. 495-496.
Melcher et al., "Thunder and Lightning: Immunotherapy and Oncolytic Viruses Collide", Molecular Therapy, 2011, vol. 19, No. 6, pp. 1008-1016.
Saul B. Needleman and Christian D. Wunsch, "A General Method Applicable to the Search for Similarities in the Amino Acid Sequence of Two Proteins", J. Mol. Biol., 1970, 48, pp. 443-453.
Quetglas et al., "Virotherapy with a Semliki Forest Virus-Based Vector Encoding IL12 Synergizes with PD-1/PD-L1 Blockade", Cancer Immunol. Res., 2015, 3(5), pp. 449-454.
Russell et al., "Oncolytic Virotherapy", Nat. Biotechnol., 2012, 30(7), pp. 658-670.
Temple F. Smith and Michael S. Waterman, "Comparison of Biosequences", Advances in Applied Mathematics, 1981, 2, pp. 482-489.

* cited by examiner

RNA VIRUSES EXPRESSING IL-12 FOR IMMUNOVIROTHERAPY

CROSS-REFERENCE TO RELATED APPLICATION

This application claims the benefit of U.S. Provisional Application No. 62/299,788, filed Feb. 25, 2016, which application is incorporated herein by reference.

FIELD OF THE INVENTION

This invention relates to biotechnology, including modified viruses, especially for the treatment or prevention of a human disease.

BACKGROUND

Interleukin 12 (IL-12) is a heterodimeric polypeptide interleukin consisting of two subunits, p35 and p40, encoded by two separate genes, IL-12A and IL-12B, respectively. IL-12 is produced in response to immune stimuli by dendritic cells, macrophages, neutrophils, and by human B-lymphoblastoid cells, and has been known as an important stimulator of immune cell activity, in particular of T cells and natural killer cells, which are, among other effects, stimulated to secrete IFN-γ by IL-12. IFN-γ, in turn, is known to stimulate expression of immune checkpoint blockade proteins on non-immune cells, e.g. of PD-L1, a mechanism used by cancer cells to evade the immune system (Abiko et al. (2015), British journal of cancer 112(9): 1501; Quetglas et al. (2015) Cancer Research 75(15 Supplement): 281). Due to the known immunostimulatory effects of IL-12, it was attempted to use a recombinant measles virus expressing both subunits of IL-12 as a vaccine to improve immune response against measles virus. However, it was found that the transgene had a detrimental effect on the neutralizing antibody response and that lymphoproliferative responses were not improved (Hoffman et al. (2003), J Infect Dis 188:1553).

Oncolytic viruses (OV) which replicate selectively in tumor cells are an emerging modality of cancer treatment. Aside from direct cytopathic effects and lysis of tumor cells, interactions of OV with the immune system can trigger systemic anti-tumor immunity. OV have been modified to express immunomodulatory transgenes to further enhance these effects (Melcher et al., Mol Ther. 2011, 19: 1008-1016). The vaccinia virus JX-594 and herpesvirus talimogene laherpavec (TVEC), both harboring GM-CSF, have shown promising results in clinical phase II and III trials (Heo et al., Nat Med. 2013, 19: 329-336 and Andtbacka et al. J Clin Oncol. 2013, 31, suppl; abstr LBA9008).

RNA viruses, in particular members of the family Paramyxoviridae like, e.g. measles virus (MV), have also shown potential use in oncolysis. Viruses of the family Paramyxoviridae are negative-sense single-stranded RNA viruses and include human pathogens like, e.g. human parainfluenza viruses, mumps virus, human respiratory syncytial virus, and measles virus. From wild type measles virus, several non-pathogenic strains, including a vaccine strain, have been derived, which have been shown to remain oncolytic. The measles virus vaccine strain has been developed as a vector platform to target multiple tumor entities and several clinical trials are ongoing (Russell et al., Nat Biotechnol. 2012, 30: 658-670). Recently, the capacity of oncolytic MV encoding GM-CSF to support the induction of a specific anti-tumor immune response in terms of a tumor vaccination effect was demonstrated (Grossardt et al. Hum Gene Ther. 2013, 24: 644-654.).

There is, however, still a need in the art for improved cancer therapies, in particular for improved oncolytic virus therapies. It is therefore an objective of the present invention to provide an improved oncolytic virus, which fully or partially avoids the short-comings of known oncolytic viruses.

SUMMARY OF THE INVENTION

The present invention relates to a recombinant virus of the family Paramyxoviridae, comprising at least one expressible polynucleotide encoding an IL-12 polypeptide, wherein said IL-12 polypeptide is an IL-12 fusion polypeptide comprising a p35 subunit of an IL-12 and a p40 subunit of an IL-12; to a polynucleotide encoding the same, and to a kit comprising the same. Moreover, the present invention relates to a method for treating cancer in a subject afflicted with cancer, comprising contacting said subject with a recombinant virus of the family Paramyxoviridae of the invention, and, thereby, treating cancer in a subject afflicted with cancer.

Relative activation corresponds to ratio of the optical density (absorbance at 450 nm minus 570 nm) of the respective samples to activated splenocytes. Data for one of three independent experiments are shown; (B) splenocytes were stimulated with recombinant murine IL-2 and cultivated in the presence of medium from Vero-αHis infected with MeVac encoding FmIL-12 or eGFP. After 48 h the supernatants were collected and IFN-γ concentration measured by ELISA. Mean results with standard error of the mean of triplicate splenocyte cultures per FmIL-12 concentration are shown. IFN-γ concentration in the eGFP controls was close to background.

Figure 1:
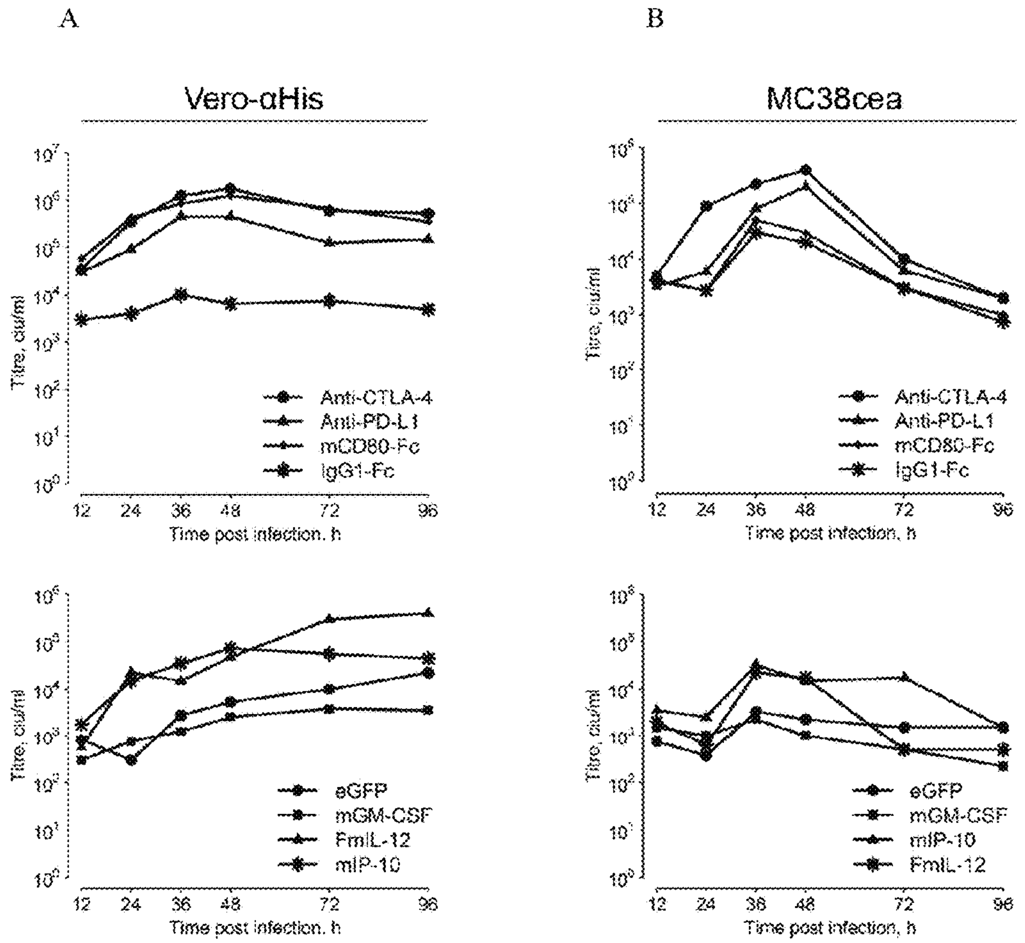
FIG. 1: One step growth curves in Vero-αHis (A) and MC38cea (B) cells: Cells were transduced with MeVac encoding the respective transgenes at MOI=3. Cell suspensions were collected by scraping in the culture medium and titre determined at the depicted time points.
Figure 2:
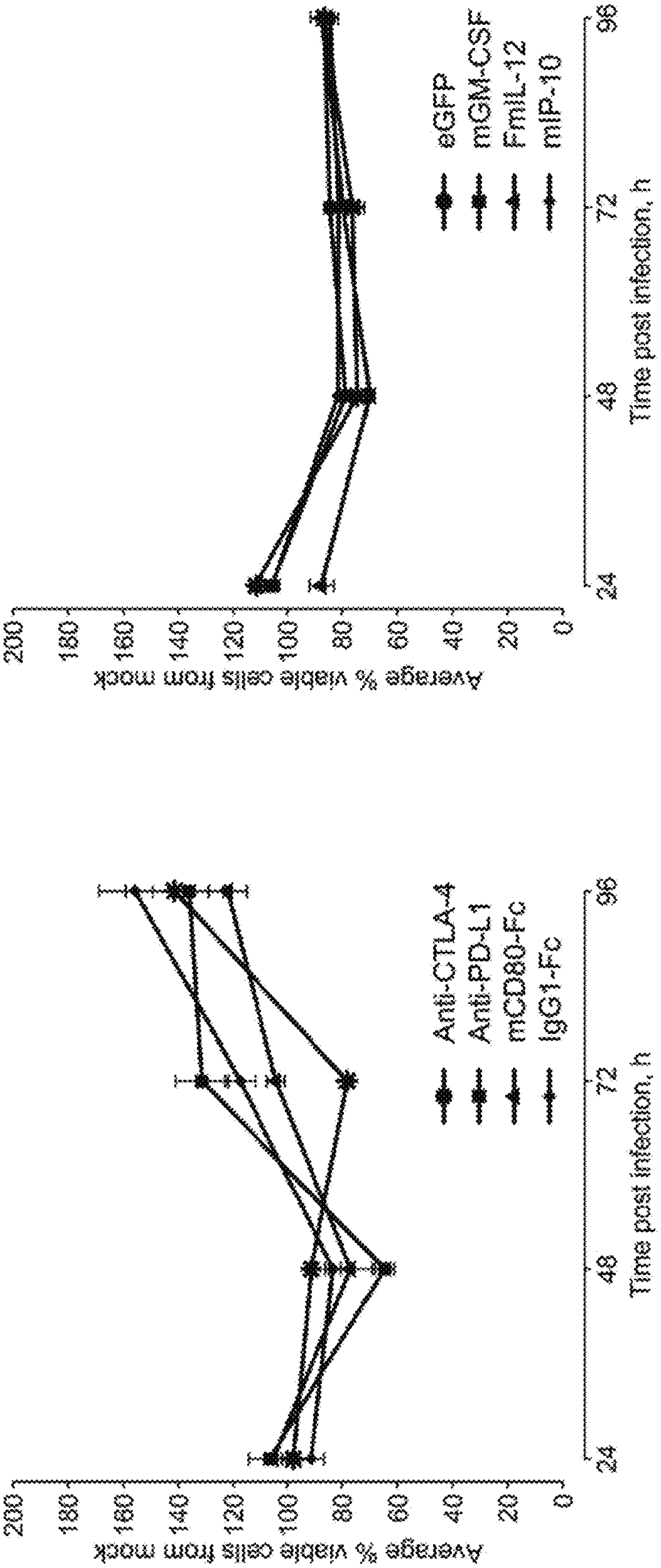
FIG. 2: Cytotoxic effect in the target MC8cea cells: Cells were transduced with MeVac encoding the respective transgenes at MOI=5 and cell viability was determined by XTT assay at the depicted time points. Mean results of triplicate infections per time point with standard errors of the mean (not visible for some data points) are shown.
Figure 3:
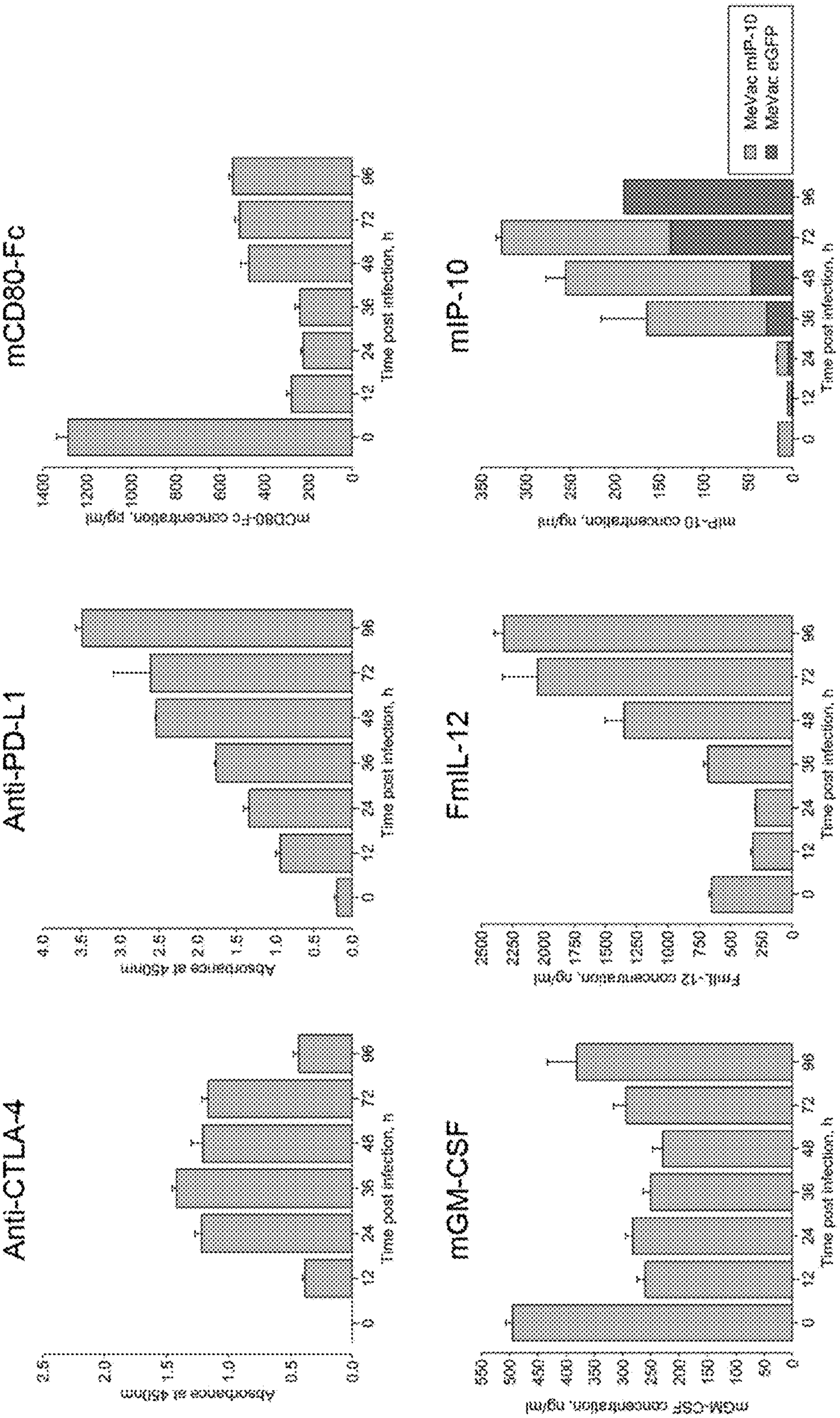
FIG. 3: Expression of MeVac encoded immunomodulators in MC38cea cells. MC38cea cells were transduced with MeVac encoding the respective immunomodulators and eGFP or IgG1-Fc as control vectors at MOI=3. Supernatant samples were collected at the depicted time points and transgene expression detected by ELISA. Unspecific binding was controlled by IgG1-Fc (upper panels) or eGFP (lower panels) supernatants and subtracted from the specific measurements. In case of mIP-10 an increase of the signal was observed in the eGFP controls which was not subtracted from the specific measurements and is depicted accordingly.
Figure 4:
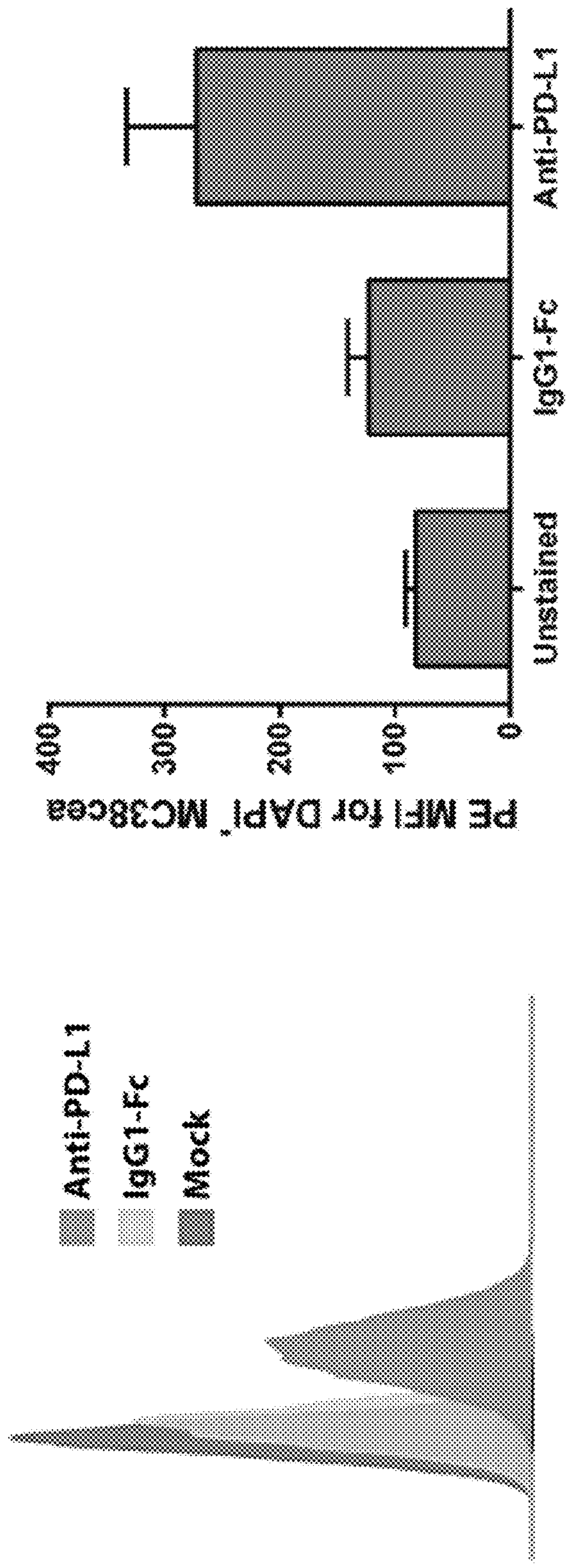
FIG. 4: MeVac encoded anti-PD-L1 binding to MC38cea cells. MC38cea cells were incubated with supernatant from Vero-αHis infected with MeVac encoding anti-PD-L1 or IgG1-Fc. For detection of bound anti-PD-L1, cells were stained with primary Ab specific for HA tag and secondary Ab coupled to PE. DAPI staining was used to exclude dead cells and samples were analyzed by flow cytometry. (A) Overlay histogram for PE of DAPI-MC38cea populations from one of three independent experiments is shown on panel (B). (B) Average median fluorescence intensity (MFI) of PE for DAPI-populations with standard error of the means from the three independent experiments is shown on the left panel.
Figure 5:
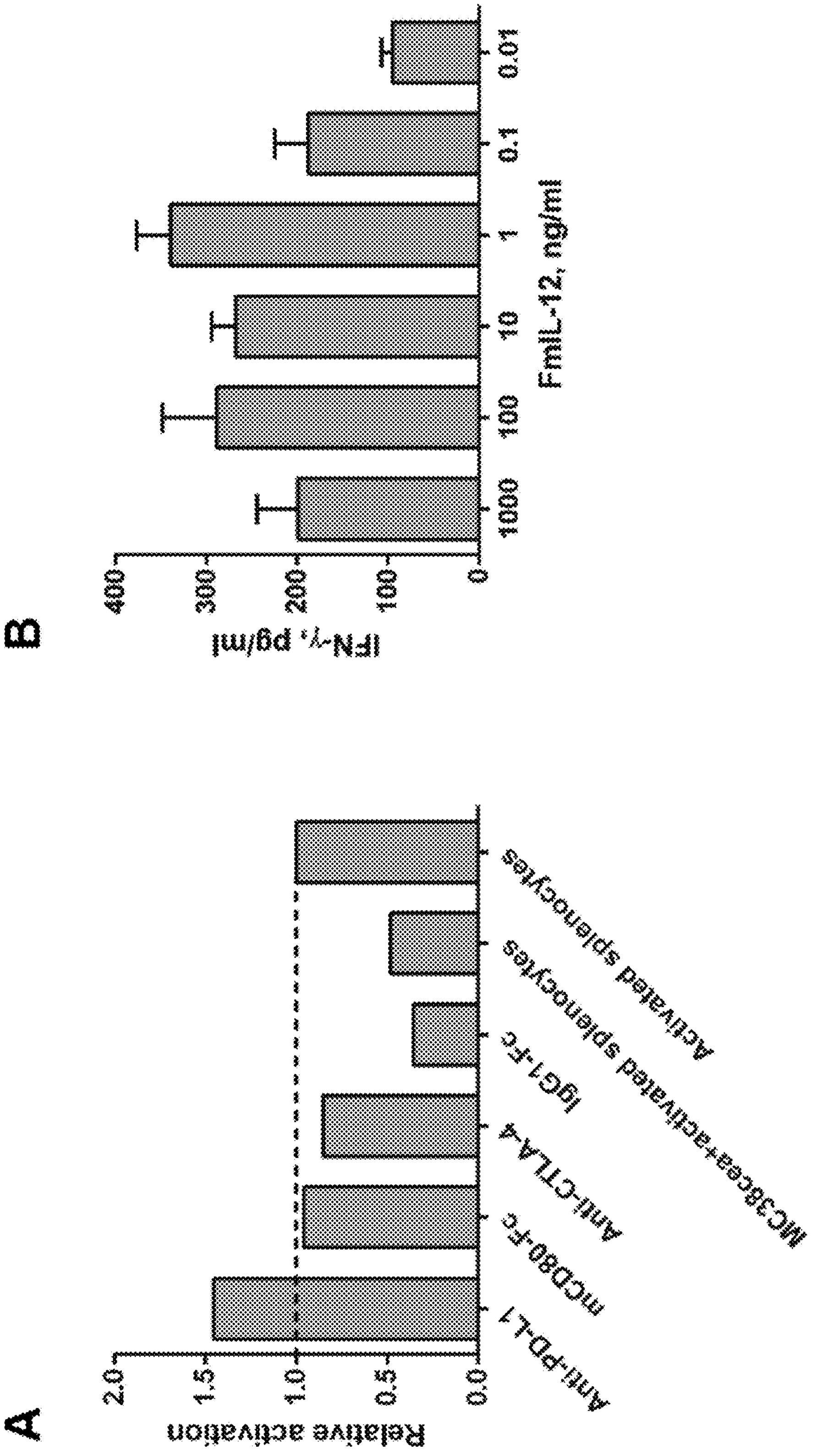
FIG. 5: Functionality of MeVac encoded immunomodulators. (A) MC38cea cells were treated with supernatants from Vero-αHis cells infected with MeVac encoding the respective immunomodulators and cocultured in ratio 2:1 with murine splenocytes in the presence of PMA and ionomycin in 96-well plate. After 24 h the supernatants were collected and IFN-γ concentration measured by ELISA.
Figure 6:
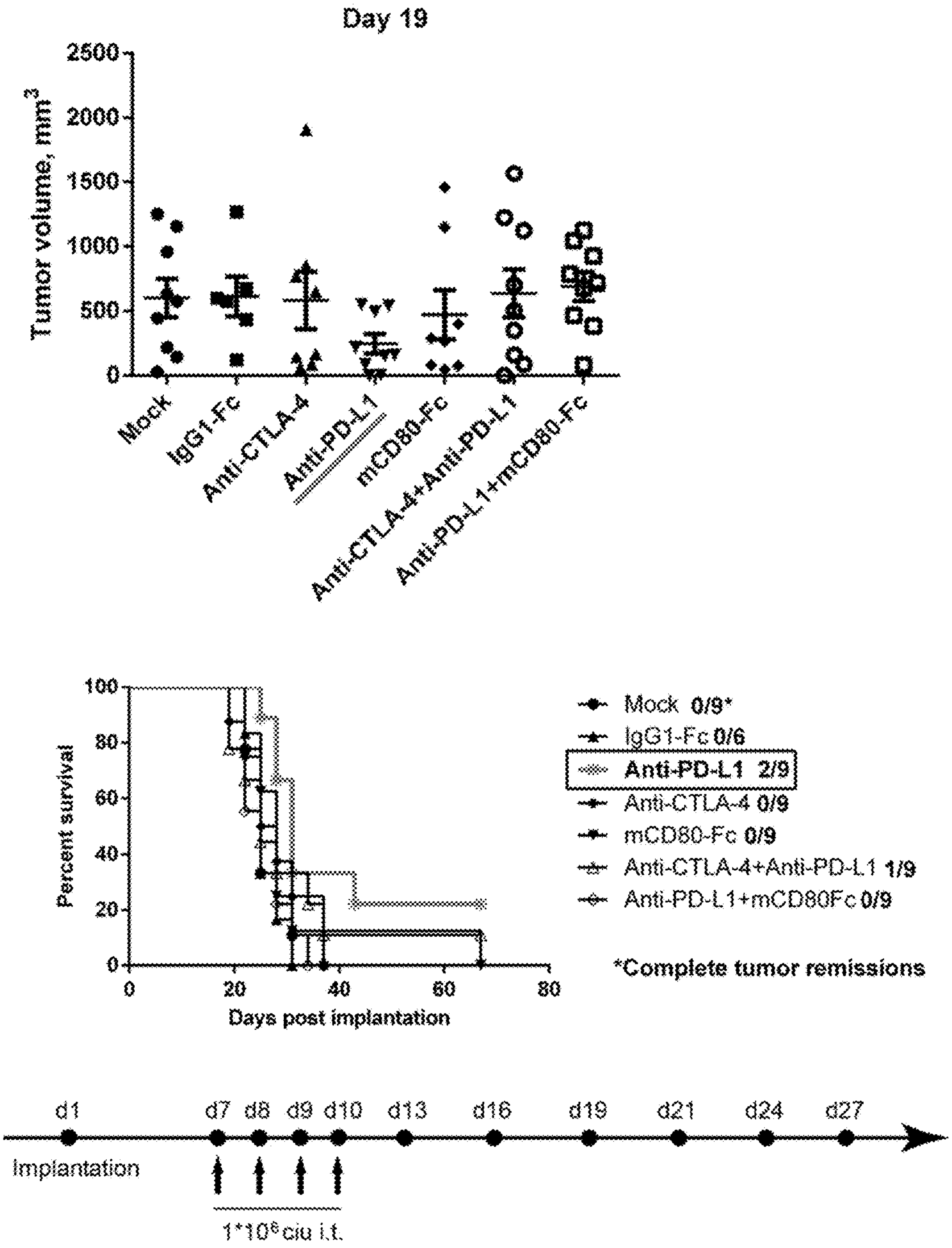

FIG. 6: Therapeutic efficacy of immunomodulatory MeVac in vivo: Breaking immunosuppression: MC38cea cells were implanted subcutaneously (s.c.) into the right flank of C57BL/6J mice (6-9 animals per group). When tumors reached an average volume of 50 mm3 mice received intratumoral injections with $1\times10^6$ cell infectious units (ciu) with the respective viruses on four consecutive days in 100 μl. Tumor volume was determined every third day and mice were sacrificed when tumor volumes exceeded 1500 $mm^3$ or when ulceration occurred.

Figure 7:
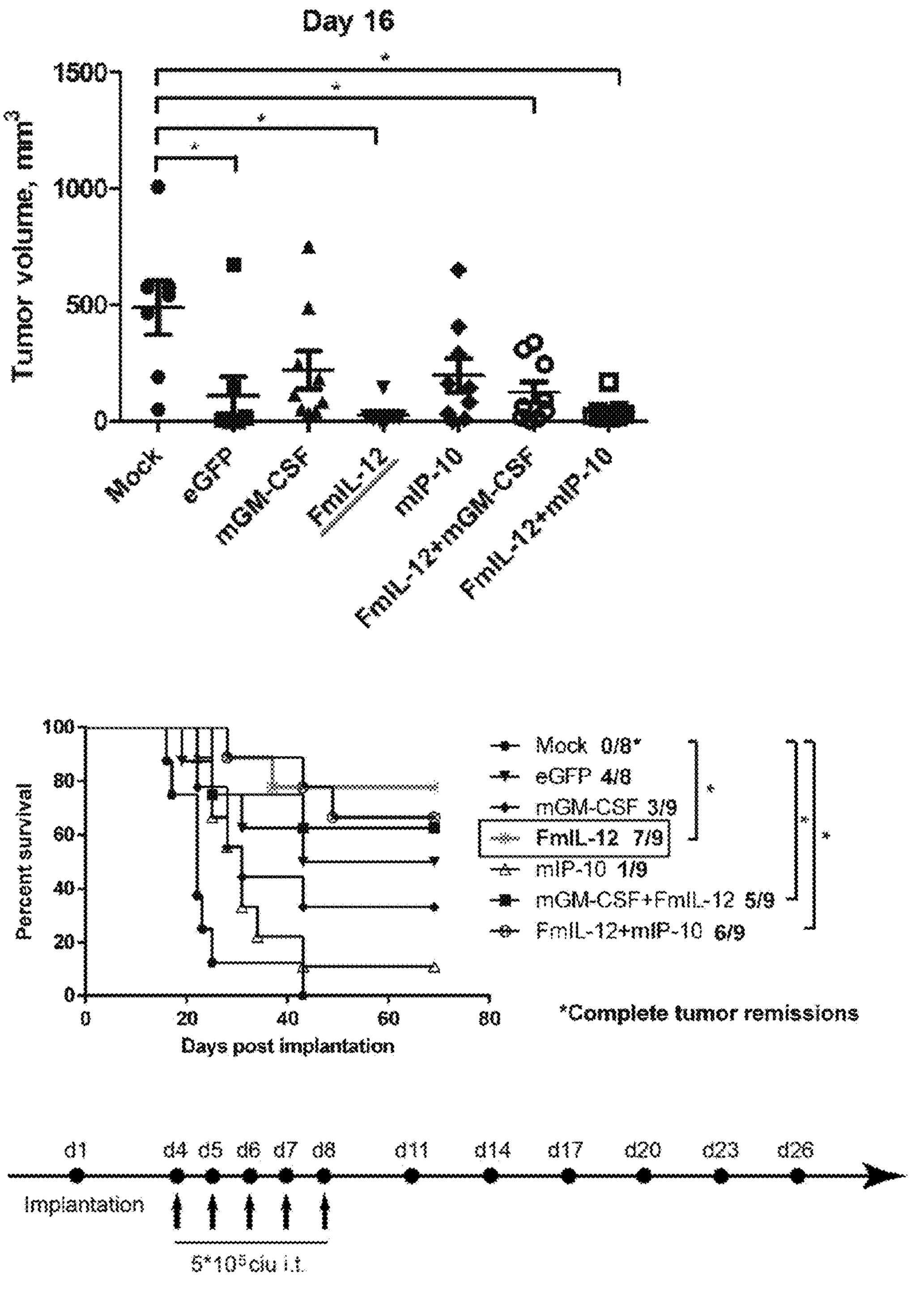

FIG. 7: Therapeutic efficacy of immunomodulatory MeVac in vivo: Activating DCs and effector cells: Therapeutic. MC38cea cells were implanted subcutaneously (s.c.) into the right flank of C57BL/6J mice (6-9 animals per group). When tumors reached an average volume of 50 mm3 mice received intratumoral injections with $5\times10^5$ ciu with the respective viruses on five consecutive days in 100 μl. Tumor volume was determined every third day and mice were sacrificed when tumor volumes exceeded 1500 $mm^3$ or when ulceration occurred.

Figure 8:
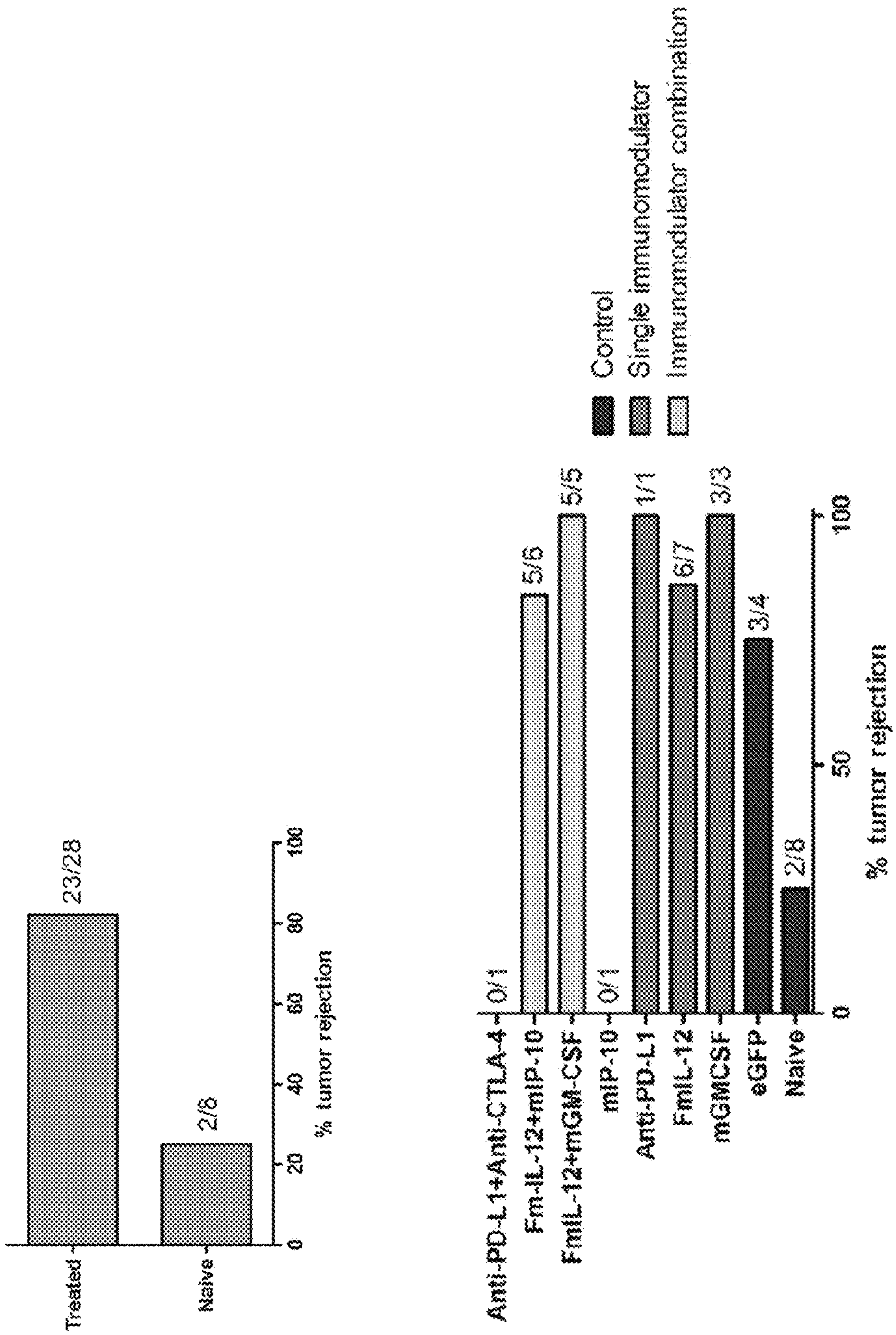

FIG. 8: Rechallenge of long term survivors with MC38cea. Mice experiencing complete tumor remission in the experiments identifying the most effective MeVac vectors and were rechallenged with MC38cea cells 3 to 6 months after the initinal tumor cell implantation. Eight 1 mice served as a control group. 1×105 MC38cea cells were implanted subcutaneously (s.c.) in the left flank of the mice. Tumor engraftment rates were monitored.

Figure 9:
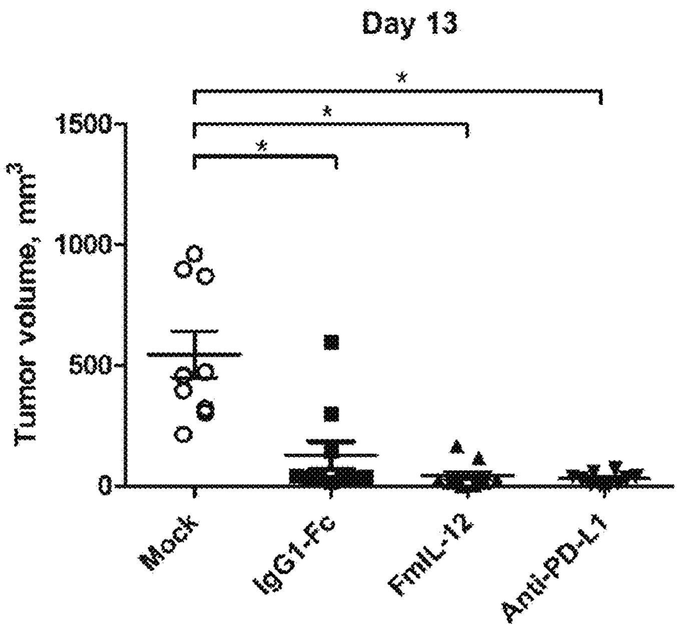
Figure 9:
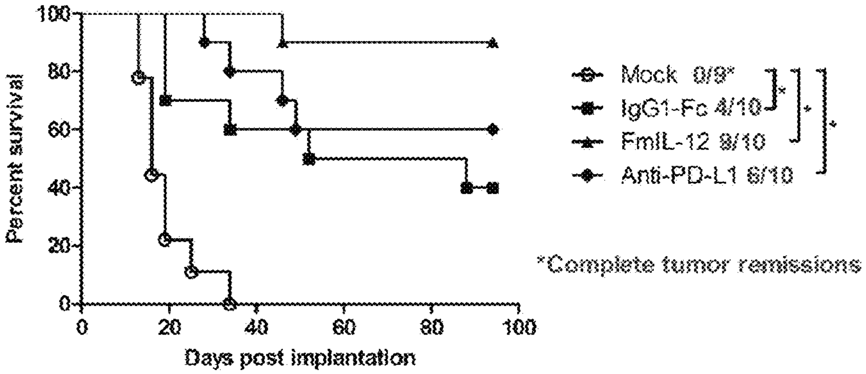
Figure 9:
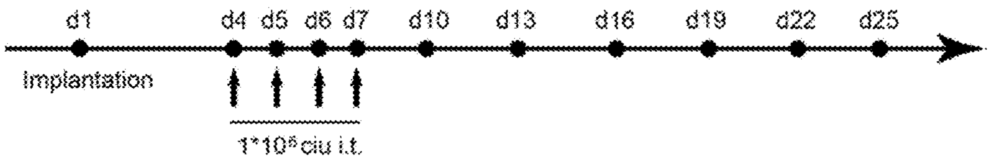

FIG. 9: Comparison of therapeutic efficacy of MeVac encoding FmIL-12 and anti-PD-L1. MC38cea cells were implanted subcutaneously (s.c.) into the right flank of C57BL/6J mice (10 animals per group). When tumors reached an average volume of 50 mm3 mice received intratumoral injections with 1×106 ciu with the respective viruses on four consecutive days in 100 μl. Tumor volume was determined every third day and mice were sacrificed when tumor volumes exceeded 1500 mm3 or when ulceration occurred.

Figure 10:
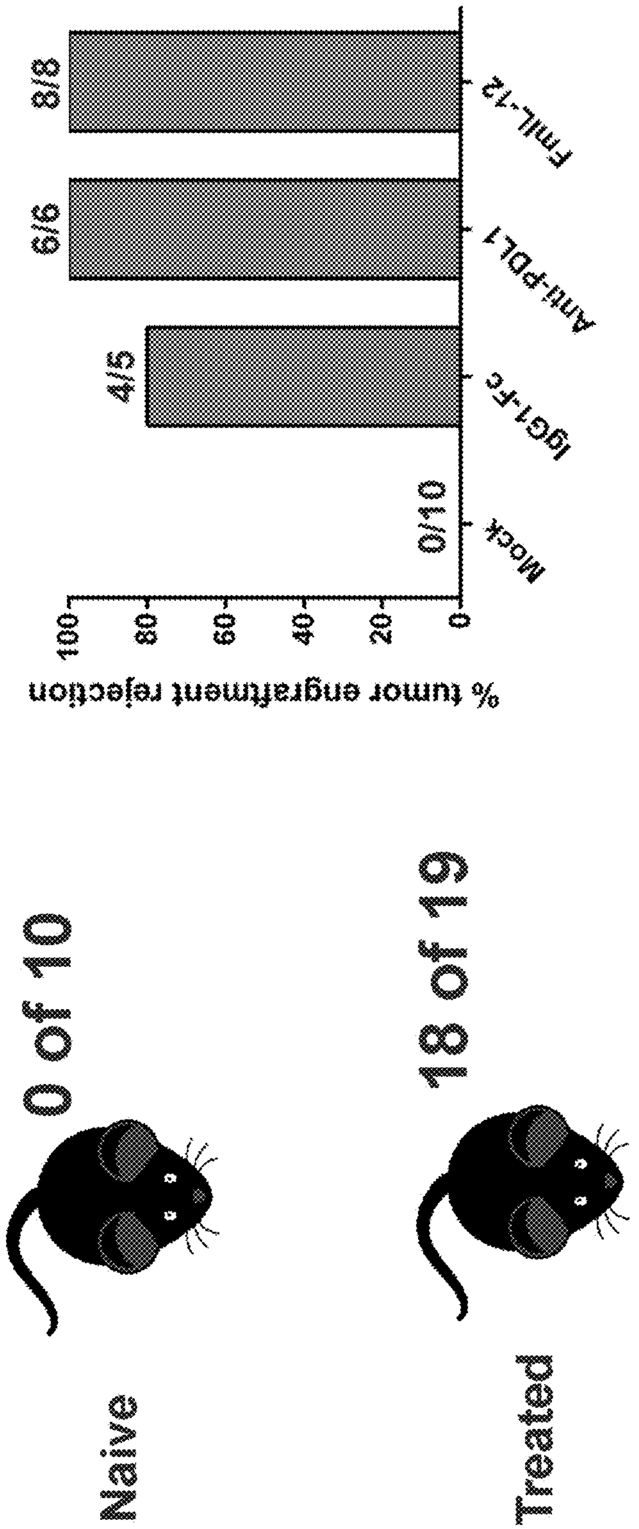

FIG. 10: Rechallenge of long term survivors from the experiment comparing efficacy of FmIL-12 and anti-PD-L1 encoding vectors with MC38cea. Mice were rechallenged with MC38cea cells ca. 6 months after the initinal tumor cell implantation. Ten 1 mice served as a control group. 1×105 MC38cea cells were implanted subcutaneously (s.c.) in the left flank of the mice. Tumor engraftment rates were monitored.

Figure 11:
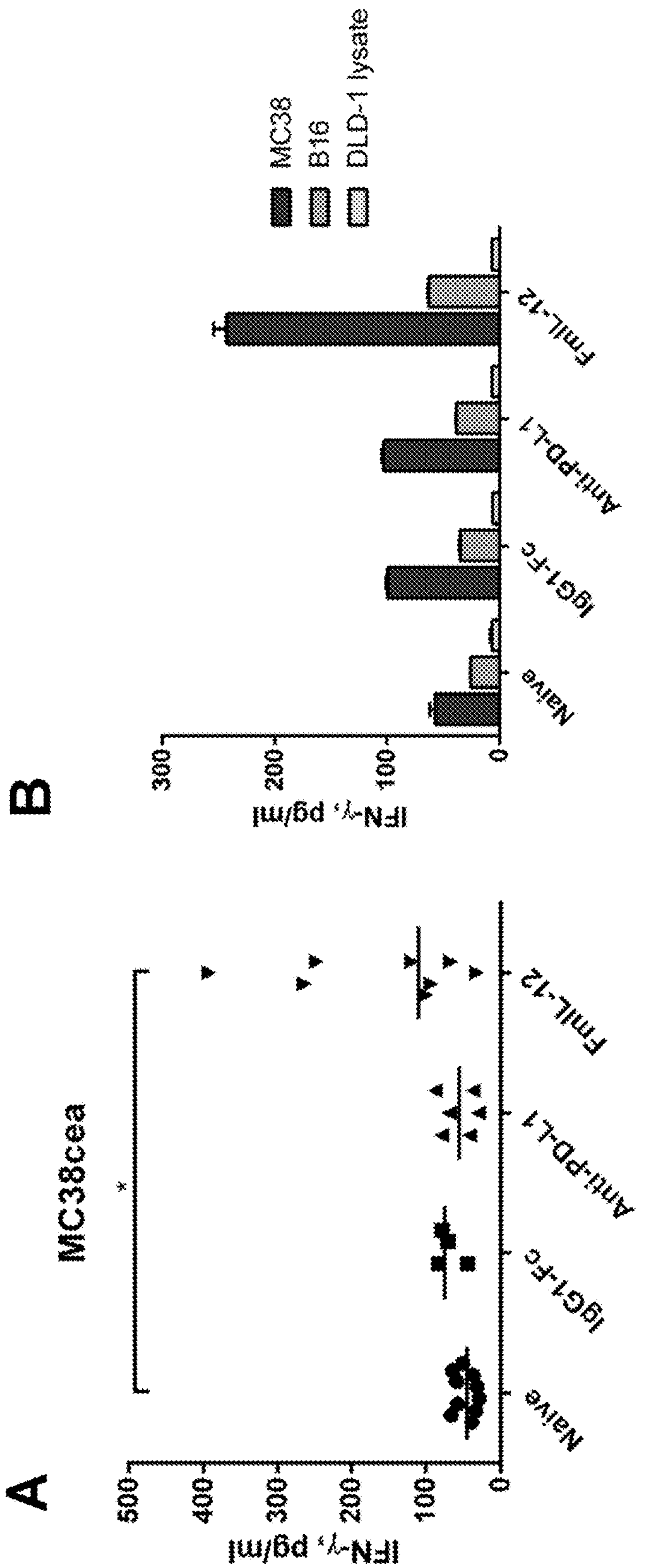

FIG. 11: IFN-γ memory recall in murine splenocytes from mice experiencing complete tumor remissions in MeVac FmIL-12 versus MeVac anti-PD-L1 efficacy experiment. Anti-tumor: Freshly isolated splenocytes from mice treated with MeVac encoding the respective immunomodulators or naïve mice were stimulated with recombinant murine IL-2 and cocultivated with MC38cea (A) or MC38 (B) and B16 (B) tumor cells or irrelevant human cell lysate (DLD-1). After 48 h of cultivation cell culture medium was collected and IFN-γ concentration was measured by ELISA. IFN-γ concentrations in the individual cocultures with median in the group (A) or average concentration from two replicate measurements with standard error of the mean (SEM) are shown (B).

Figure 12:
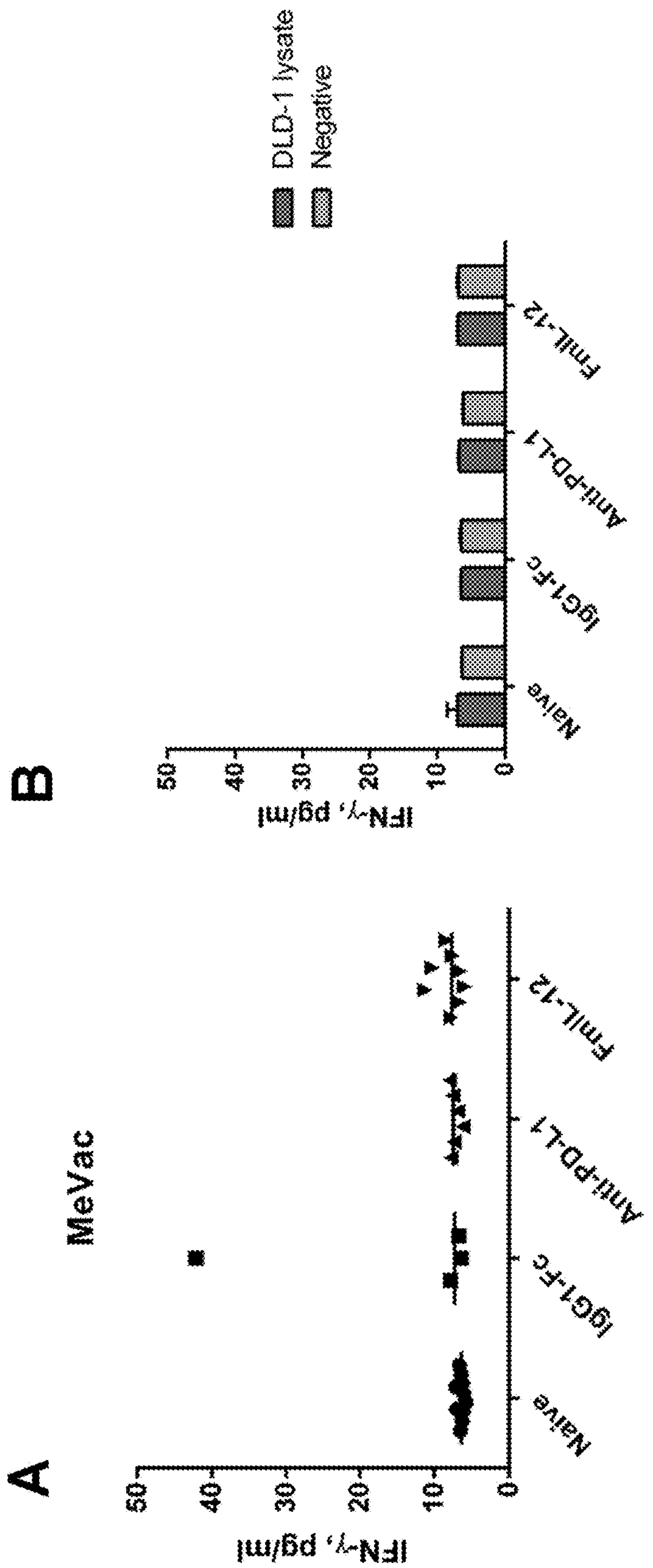

FIG. 12: IFN-γ memory recall in murine splenocytes from mice experiencing complete tumor remissions in MeVac FmIL-12 versus MeVac anti-PD-L1 efficacy experiment: Anti-MeVac: Freshly isolated splenocytes from mice treated with MeVac encoding the respective immunomodulators or naïve mice were stimulated with recombinant murine IL-2 and cocultivated with MeVac (A) or as controls with an irrelevant human cell lysate (DLD-1) (B) or as a negative control splenocytes were cultivated alone. After 48 h of cultivation cell culture medium was collected and IFN-γ concentration was measured by ELISA. IFN-γ concentrations in the individual cocultures with median in the group (A) or average concentration from two replicate measurements with standard error of the mean (SEM) are shown (B).

Figure 13:
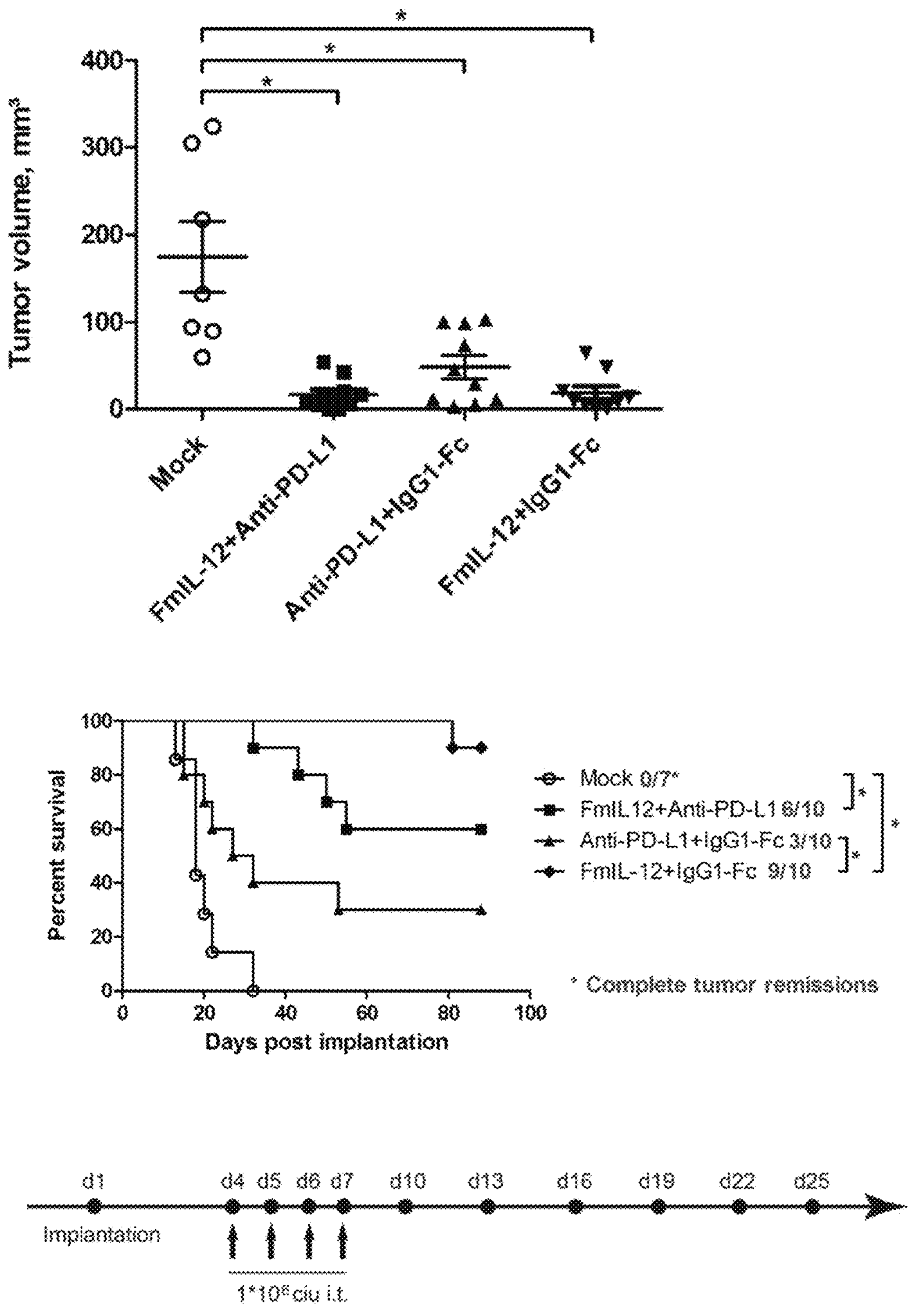

FIG. 13: Comparison of therapeutic efficacy of combination of MeVac encoding Fm-IL-12 and anti-PD-L1 with either vector in combination with a control vector encoding IgG1-Fc. MC38cea cells were implanted subcutaneously (s.c.) into the right flank of C57BL/6J mice (8-10 animals per group). When tumors reached an average volume of 50 mm3 mice received intratumoral injections with 1×106 ciu with the respective viruses on four consecutive days in 100 μl. Tumor volume was determined every third day and mice were sacrificed when tumor volumes exceeded 1500 mm3 or when ulceration occurred.

Figure 14:
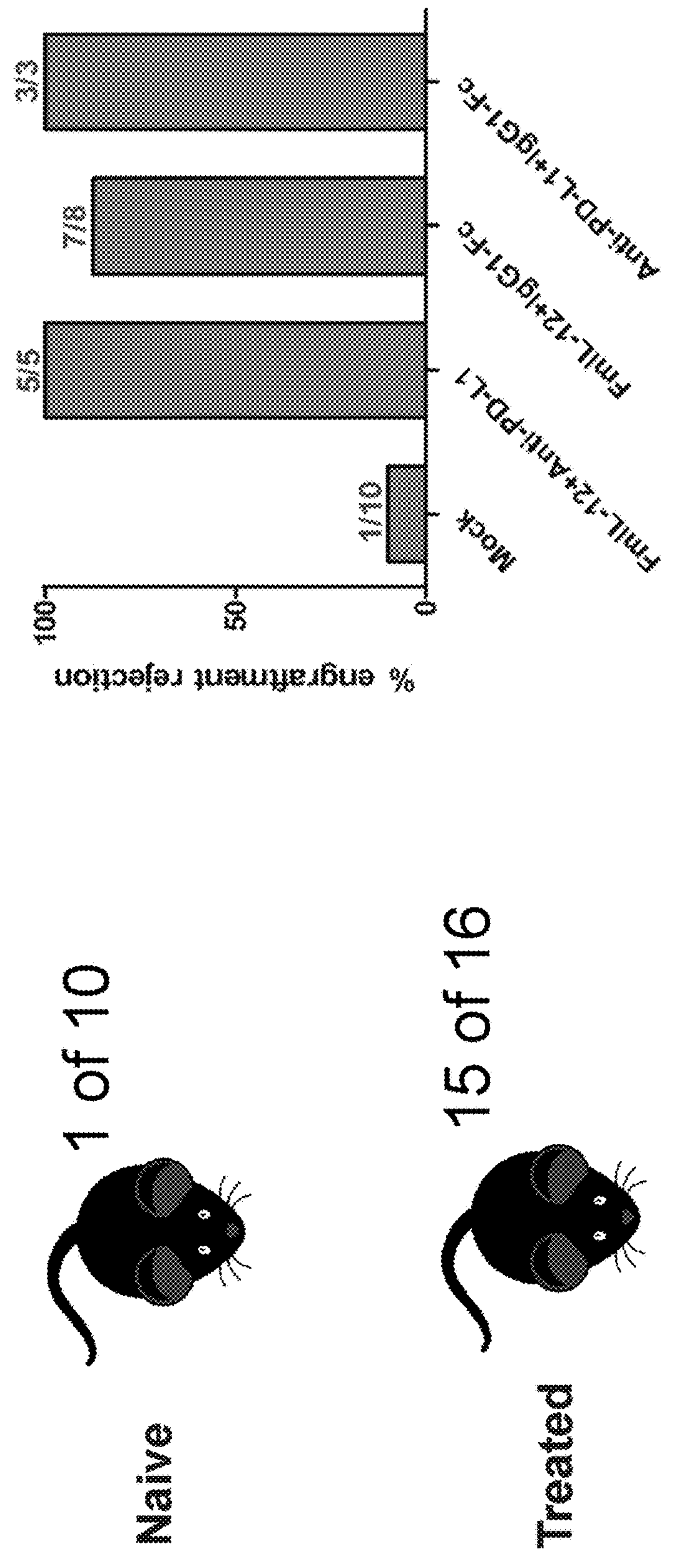

FIG. 14: Rechallenge of long term survivors from the experiment comparing efficacy of combination of MeVac encoding Fm-IL-12 and anti-PD-L1 with either vector in combination with a control vector encoding IgG1-Fc. Mice were rechallenged with MC38cea cells ca. 5 months after the initinal tumor cell implantation. Ten 1 mice served as a control group. 1×105 MC38cea cells were implanted subcutaneously (s.c.) in the left flank of the mice. Tumor engraftment rates were monitored.

Figure 15:
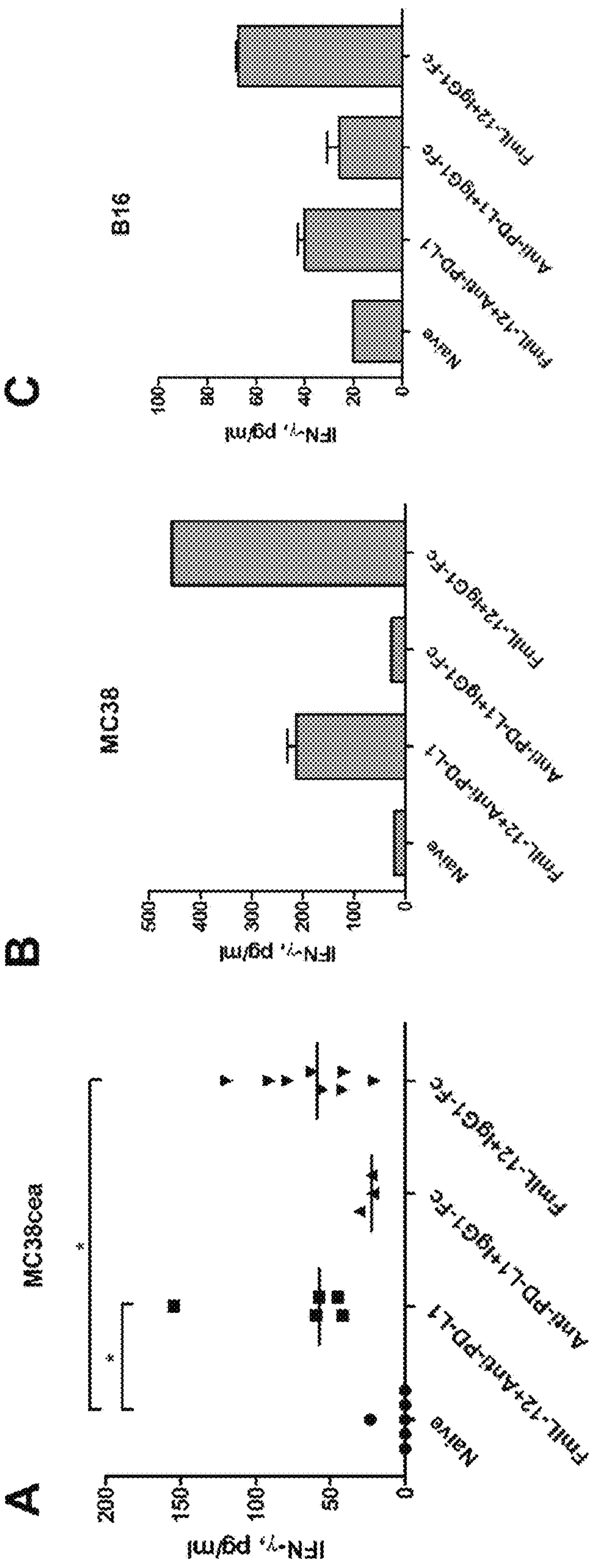

FIG. 15: IFN-γ memory recall in murine splenocytes from mice experiencing complete tumor remissions in MeVac FmIL-12 and MeVac anti-PD-L1 combination experiment: Anti-tumor: Freshly isolated splenocytes from mice treated with MeVac encoding the respective immunomodulators or naïve mice were stimulated with recombinant murine IL-2 and cocultivated with MC38cea (A), MC38 (B) or B16 (C) tumor cells. After 48 h of cultivation cell culture medium was collected and IFN-γ concentration was measured by ELISA. IFN-γ concentrations in the individual cocultures with median in the group (A) or average concentration from two replicate measurements with standard error of the mean (SEM) are shown (B).

Figure 16:
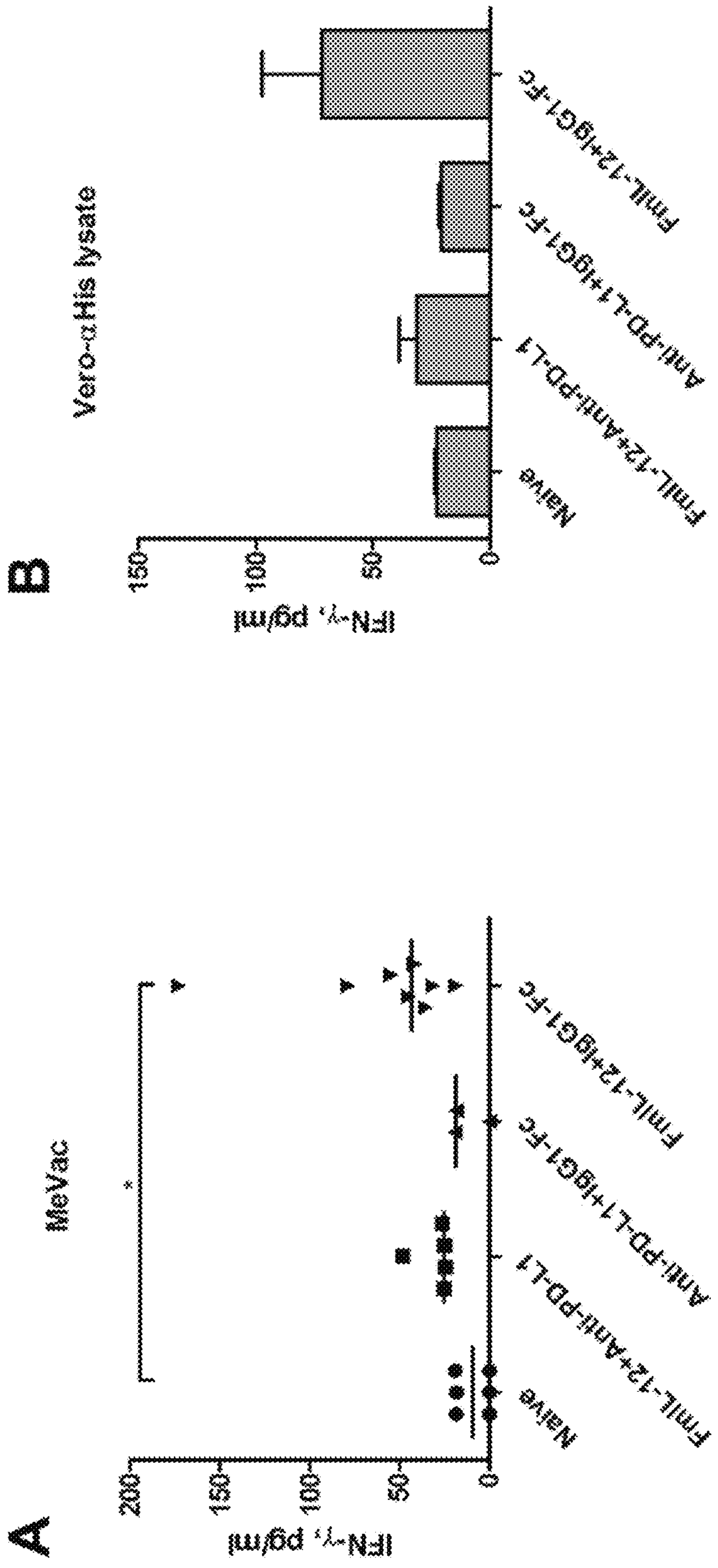

FIG. 16: IFN-γ memory recall in murine splenocytes from mice experiencing complete tumor remissions in MeVac FmIL-12 and MeVac anti-PD-L1 combination experiment: Anti-MeVac: Freshly isolated splenocytes from mice treated with MeVac encoding the respective immunomodulators or naïve mice were stimulated with recombinant murine IL-2 and cocultivated with MeVac (A) or Vero-αHis lysate (B). After 48 h of cultivation cell culture medium was collected and IFN-γ concentration was measured by ELISA. IFN-γ concentrations in the individual cocultures with median in the group (A) or average concentration from two replicate measurements with standard error of the mean (SEM) are shown (B).

Figure 17:
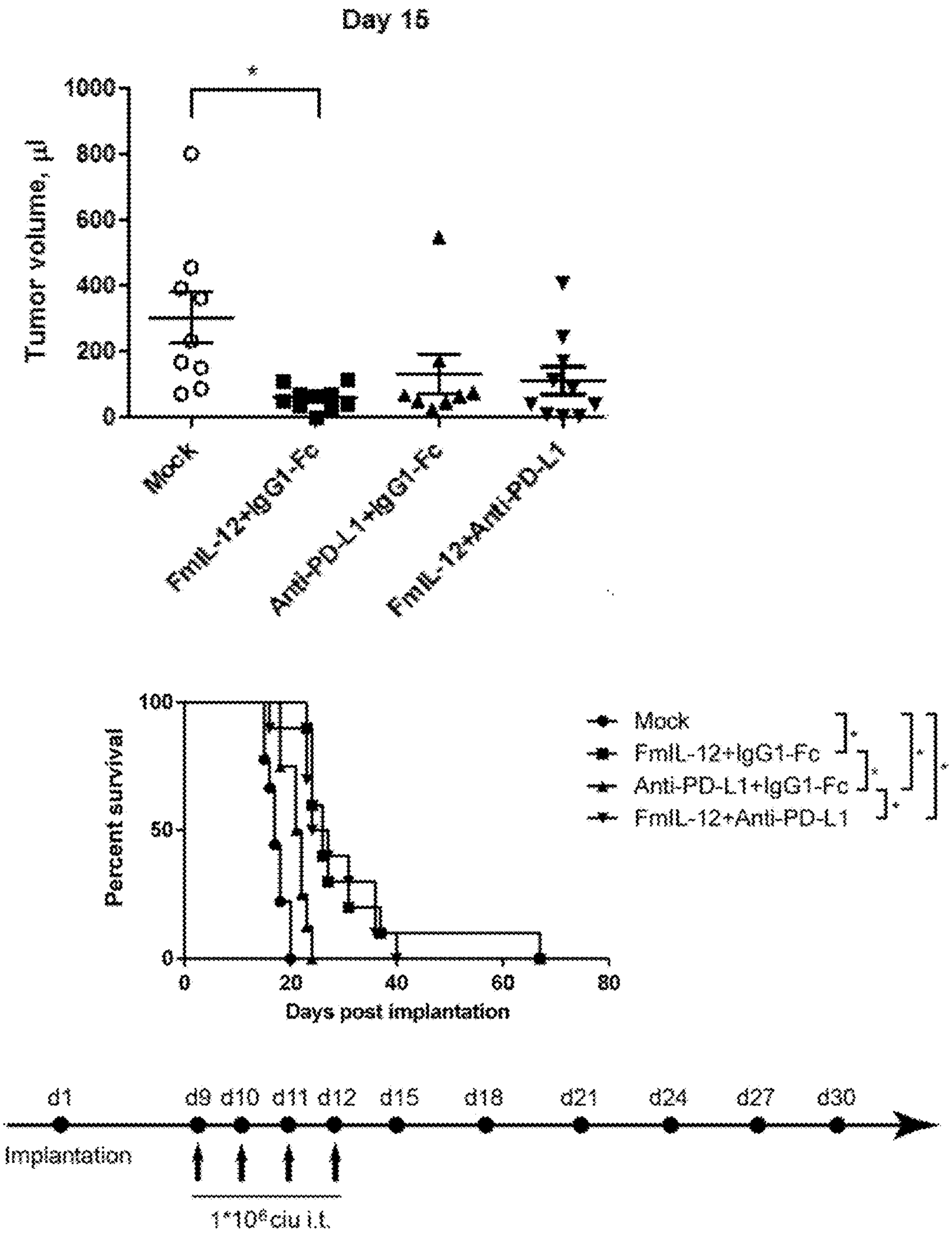

FIG. 17: Comparison of therapeutic efficacy of combination of MeVac encoding Fm-IL-12 and anti-PD-L1 with either vector in combination with a control vector encoding IgG1-Fc. B16-CD20 cells were implanted subcutaneously (s.c.) into the right flank of C57BL/6J mice (8-10 animals per group). When tumors reached an average volume of 50 mm3 mice received intratumoral injections with 1×106 ciu with the respective viruses on four consecutive days in 100 μl. Tumor volume was determined every third day and mice were sacrificed when tumor volumes exceeded 1500 mm3 or when ulceration occurred.

Figure 18:
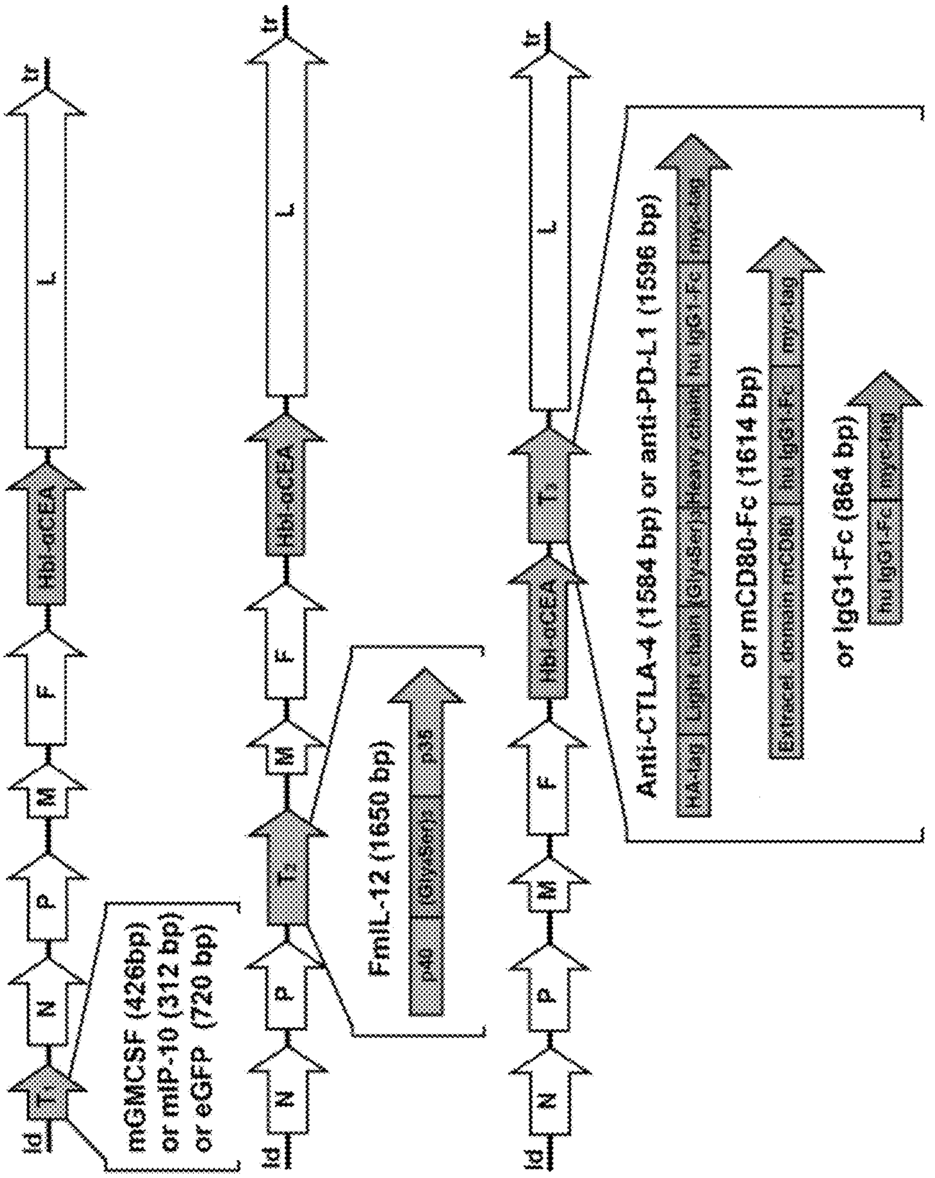

FIG. 18: Schemes of the constructed recombinant MeVac genomes. Transgenes encoding different immunomodulators as well as eGFP and IgG1-Fc as controls were inserted in different positions of MeVac genome. Murine IL-12 was inserted as a fusion protein consisting of p40 and p35 protein subunits linked by a (Gly4Ser)3 linker (FmIL-12). Murine CD80 was inserted as a soluble form of the protein consisting of the extracellular part of the protein fused to a human IgG1-Fc (CD80-Fc). The MeVac H gene in the novel constructs was fully retargeted to human CEA (hCEA) antigen by ablating attachment to the natural receptors, fusing the H protein to a single chain antibody (7cab) against the hCEA and including a six-histidine tag at the C terminus to allow specific transduction of murine MC38cea cells via human CEA antigen and Vero-αHis cells via anti-His 7cab.

Figure 19:
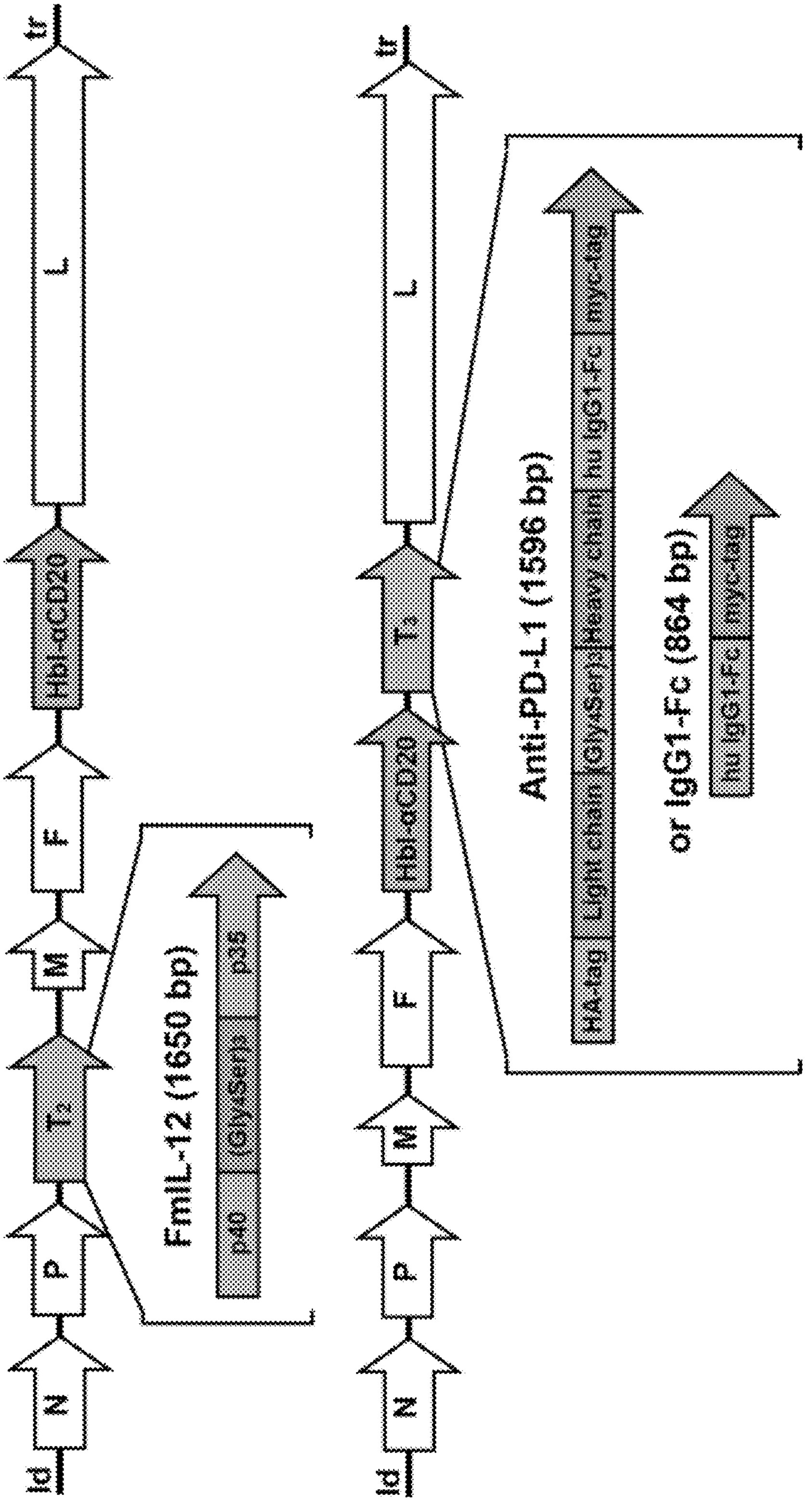

FIG. 19: Scheme of MeVac genomes encoding FmIL-12 or anti-PD-L1 or IgG1-Fc retargeted to human CD20. MeVac H gene was fully retargeted to human CD20 antigen by ablating attachment to the natural receptors, fusing the H protein to a single chain antibody (7cab) against the CD20 and including a six-histidine tag at the C terminus to allow specific transduction of murine melanoma B16-CD20 cells via human CD20 antigen and Vero-αHis cells via anti-His 7cab.

DETAILED DESCRIPTION OF THE INVENTION

Accordingly, the present invention relates to a recombinant virus of the family Paramyxoviridae, comprising an expressible polynucleotide encoding an IL-12 polypeptide, wherein said IL-12 polypeptide is an IL-12 fusion polypeptide comprising a p35 subunit of an IL-12 and a p40 subunit of an IL-12.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value ±20%.

The terms "virus" and "virus of the family Paramyxoviridae" are known to the skilled person. Preferably, the virus of the family Paramyxoviridae is a member of the genus Morbillivirus. More preferably, the virus of the family Paramyxoviridae is a measles virus (MV), still more preferably an MV of strain Edmonston A or B, preferably B. Most preferably, the virus of the family Paramyxoviridae is an MV of vaccine strain Schwarz/Moraten.

The term "recombinant virus", as used herein, relates to a virus comprising a genome modified by biotechnological means as compared to known, naturally occurring, virus genomes. Preferably, the recombinant virus is a virus comprising a genome modified as compared to naturally occurring virus genomes. Preferred biotechnological means for modifying a viral genome are known to the skilled person and include any of the methods of molecular cloning, in particular recombinant DNA techniques including, without limitation, cleavage of DNA by restriction enzymes, ligation of DNA, polymerase chain reaction (PCR), cloning of viral genomes, and the like. It is understood by the skilled person that viruses of the family Paramyxoviridae have a single-stranded (−)-RNA as a genome. Accordingly, the genome of the recombinant virus of the present invention, preferably, is obtained by cloning an expression vector as described herein below comprising an expressible nucleotide sequence encoding said recombinant virus genome, followed by expressing said expressible nucleotide sequence encoding said recombinant virus in a permissive host cell. Alternatively, the recombinant virus genome may also be expressed in non-permissive host cells, e.g., preferably, from rodents or other higher eukaryotes. Preferably, the recombinant virus of the present invention is a recombinant virus of the family Paramyxoviridae, more preferably a recombinant Morbillivirus, most preferably, a recombinant measles virus (MV). As will be understood by the skilled person, the recombinant virus of he present invention may comprises further modifications as compared to a naturally occurring virus. Preferably, the recombinant virus comprises a polypeptide mediating a modified tropism and/or a polynucleotide encoding the same. More preferably, said polypeptide mediating a modified tropism is a fusion polypeptide of a viral membrane integral polypeptide or of a viral membrane associated polypeptide with a polypeptide mediating binding to a target, e.g. a cell, preferably a specific kind of cell, more preferably a cancer cell. Preferably, said fusion polypeptide comprises a viral hemagglutinin or a fragment thereof, preferably a membrane integral fragment thereof. Preferably, said fusion polypeptide comprises a single-chain antibody specifically binding to a target molecule, e.g. to Carcinoembryonic antigen (CEA) or CD20. Most preferably, said fusion polypeptide is a fusion polypeptide of a truncated viral hemagglutinin with an anti-CD20 single-chain antibody or with an anti-CEA single-chain antibody. Preferably, the recombinant virus comprises a polynucleotide comprising the nucleic acid sequence of any one of SEQ ID Nos: 4 to 7, 14, and 15. SEQ ID NO: 4 is an artificial MV genome encoding an IL-12 fusion polypeptide comprising the mouse p40 subunit of IL-12 and the mouse p35 subunit of IL-12 as specified elsewhere herein. SEQ ID NO: 5 is an artificial MV genome encoding an IL-12 fusion polypeptide comprising the human p40 subunit of IL-12 and the human p35 subunit of IL-12 as specified elsewhere herein. SEQ ID NO: 6 is an artificial MV genome encoding an IL-12 fusion polypeptide comprising the mouse p40 subunit of IL-12 and the mouse p35 subunit of IL-12 as specified elsewhere herein, and a fusion polypeptide comprising a viral hemagglutinin and an anti-human-CEA single-chain antibody. SEQ ID NO: 7 is an artificial MV genome encoding an IL-12 fusion polypeptide comprising the mouse p40 subunit of IL-12 and the mouse p35 subunit of IL-12 as specified elsewhere herein, and a fusion polypeptide comprising a viral hemagglutinin and an anti-human-CD20 single-chain antibody. SEQ ID NO: 14 is an artificial MV genome derived from strain Edmonston B encoding an IL-12 fusion polypeptide comprising the mouse p40 subunit of IL-12 and the mouse p35 subunit of IL-12 as specified elsewhere herein. SEQ ID NO: 15 is an artificial MV genome encoding an IL-12 fusion polypeptide comprising the human p40 subunit of IL-12 and the human p35 subunit of IL-12 as specified elsewhere herein.

As used herein, the term "IL-12" relates to an interleukin 12 which is, in principle, known to the skilled person. Preferably, IL-12 is the heterodimeric IL-12 having the activity of stimulating the immune response of a subject. Preferably, the IL-12 is an IL-12 of a vertebrate species, more preferably of a mammal, even more preferably of a rat, a mouse, or a human, most preferably of a human. Preferably, the IL-12 has the subunits of rat IL-12, i.e. p35 comprising the amino acid sequence of Genbank Acc. No: NP_445842.1 GI:16758120, and p40 comprising the amino acid sequence of Genbank Acc. No: NP_072133.1 GI:12018288. Preferably, the subunits of the rat IL-12 are encoded by a polynucleotide comprising the nucleic acid sequence of Genbank Acc. No: NM_053390.1 GI:16758119 (rat mRNA expressed from the rat IL-12A gene) and/or of Genbank Acc. No: NM_022611.1 GI:12018287 (rat mRNA expressed from the rat IL-12B gene). More preferably, the IL-12 has the subunits of mouse IL-12, i.e. p35 comprising the amino acid sequence of Genbank Acc. No: NP_001152896.1 GI:226874945, and p40 comprising the amino acid sequence of Genbank Acc. No: NP_001290173.1 GI:735997434. Preferably, the subunits of the mouse IL-12 are encoded by a polynucleotide comprising the nucleic acid sequence of Genbank Acc. No: NM_001159424.2 GI:746816821 (mouse mRNA expressed from the mouse IL-12A gene) and/or of Genbank Acc. No: NM_001303244.1 GI:735997433 (mouse mRNA expressed from the mouse IL-12B gene). Most preferably, the IL-12 has the subunits of human IL-12, i.e. p35 comprising the amino acid sequence of Genbank Acc. No: NP_000873.2 GI:24430219, and p40 comprising the amino acid sequence of Genbank Acc. No: NP_002178.2 GI:24497438. Preferably, the subunits of the human IL-12 are encoded by a polynucleotide comprising the nucleic acid sequence of Genbank Acc. No: NM_000882.3 GI:325974478 (human mRNA expressed from the human IL-12A gene) and/or of Genbank Acc. No: NM_002187.2 GI:24497437 (human mRNA expressed from the human IL-12B gene). In its natural form, IL-12 is a secreted interleukin, i.e. it is processed and transported from the interior of the producing cell to the exterior of the producing cell by said producing cell. Accordingly, IL-12 preferably is a secreted IL-12.

More preferably, the IL-12 according to the present invention is an IL-12 fusion polypeptide comprising a p40 subunit of an IL-12 and a p35 subunit of an IL-12, preferably comprising subunits as specified herein above. More preferably, the p40 subunit and the p35 subunit of said IL-12 fusion polypeptide are from the same species; i.e. preferably, the p40 subunit and the p35 subunit of said IL-12 fusion polypeptide are a rat p40 subunit and a rat p35 subunit, more preferably are a mouse p40 subunit and a mouse p35 subunit, most preferably are a human p40 subunit and a human p35 subunit. Preferably, said p40 subunit and said p35 subunit are comprised in the order N-terminus—p40 subunit—p35 subunit—C-terminus in said fusion polypeptide. Preferably, said p40 subunit and said p35 subunit are separated by a linker, i.e., the fusion polypeptide comprises the structure p40-linker-35.

The term "linker" is known to the skilled person and, preferably, relates to a short sequence of amino acids separating two domains of a polypeptide or two components of a fusion polypeptide. The skilled person knows how to select appropriate linker sequences in order to construct functional fusion polypeptides, e.g. from Xue et al. (2004), NAR 32 (Web server issue):W562. Preferably, said linker comprises of from 1 to 50, more preferably of from 2 to 25, most preferably of from 10 to 20 amino acids. Preferably, the amino acids of the linker are small amino acids and/or amino acids promoting turns in protein structure; accordingly, the amino acids comprised in the linker, preferably, are glycine, alanine, serine, and/or proline. Preferably, the linker has a repetitive structure; thus, preferably, the linker comprises of from 1 to 10, more preferably of from 2 to 5, most preferably 3 repetitions of an amino acid sequence comprising 3 or 4, preferably 5 amino acids. Preferably, the repetitive sequence of the linker comprises the sequence (glycine$_x$-serine), with x=3 to 6, preferably 4 to 6, more preferably 4 or 6. More preferably, the repetitive sequence of the linker comprises the sequence (glycine$_4$-serine), i.e. gly-gly-gly-gly-ser (SEQ ID NO:1), preferably repeated as specified above. Thus, preferably the linker comprises or consists of the amino acid sequence -(glycine$_4$-serine)$_n$-, with n=1 to 10, preferably n=2 to 5, more preferably n=3. Most preferably, the linker has the amino acid sequence of SEQ ID NO:8. Also more preferably, the repetitive sequence of the linker comprises the sequence (glycine$_6$-serine), i.e. gly-gly-gly-gly-gly-gly-ser (SEQ ID NO 9).

As used herein, the term "fusion polypeptide" relates to a polypeptide wherein all components, e.g. p35 subunit, linker, and p40 subunit, are covalently linked and, preferably, are produced as a contiguous polypeptide chain. Thus, preferably, the fusion polypeptide of the present invention, preferably, is expressed from a single gene. Thus, the IL-12 of the present invention preferably is fused mouse IL-12 (FmIL-12), preferably comprising the amino acid sequence of SEQ ID NO:10, preferably encoded by a polynucleotide comprising the nucleic acid sequence of SEQ ID NO:11. More preferably, the IL-12 of the present invention preferably is fused human IL-12 (FhIL-12), preferably comprising the amino acid sequence of SEQ ID NO:12, preferably encoded by a polynucleotide comprising the nucleic acid sequence of SEQ ID NO:13.

The terms "polypeptide" and "fusion polypeptide", as used herein, preferably encompass variants of said polypeptides and fusion polypeptides as specified elsewhere herein.

Preferably, the recombinant virus of the family Paramyxoviridae of the present invention further comprises at least one expressible polynucleotide encoding a further activator of the immune response, preferably an immunoglobulin or part thereof, preferably a secreted immunoglobulin.

As used herein, the term "further activator of the immune response" relates to a compound which, when contacted with a mixture of immune cells and immune-response inducing cells, e.g. cancer cells, causes at least one type of immune cell to be more active as compared to an immune cell of the same type comprised in the same mixture but lacking said compound. As used herein, the term IL-12 as specified elsewhere herein relates to an activator of the immune response, but not to a further activator of the immune response. Preferably, the immune cell activated is a cell mediating a response increasing a subject's resistance to an antigen, i.e. preferably, said immune cell is not a tolerance-mediating immune cell. Preferably, the immune cell activated by the further activator of the immune response is a T-cell, more preferably a helper T-cell or a cytotoxic T-cell. Most preferably, the immune cell activated by the further activator of the immune response is a cytotoxic T-cell expressing PD-1. Measures of immune cell activity are known to the skilled person and include, preferably, expression of activation markers, production of antibodies, excretion of cytokines, and release of cytotoxins, e.g. perforin, granzymes, and/or granolysin.

Preferably, the further activator of the immune response is an antagonist of a signaling pathway causing at least one type of immune cell to become inhibited. Accordingly, preferably, the further activator of the immune response is a ligand for an immune checkpoint blockade protein. More preferably, the further activator of the immune response is a ligand for an immune checkpoint blockade protein. Still more preferably, the activator of the immune response is an inhibitor of PD-1 receptor signaling. It is understood by the skilled person that signaling through a receptor signaling pathway can be inhibited by either preventing the receptor from being activated, or by preventing the signal generated by the activated receptor from being further transmitted. Accordingly, preferably, the further activator of the immune response is a PD-L1 antagonist, the term "antagonist" relating to a compound binding to the molecule the effect of which is antagonized and through said binding preventing said molecule from interacting with its native binding partner in a productive, i.e. signaling-inducing, way. Preferred assays for said activity are described e.g. in WO 2015/128313 A1.

Preferably, the further activator of the immune response is an antagonist as described above selected from the list of molecule types consisting of a peptide aptamer, an anticalin, a Designed Ankyrin Repeat Protein (DARPin), an inhibitory peptide, and, preferably, an immunoglobulin, more preferably, an antibody.

In the context of this invention, a "peptide aptamer" is a peptide specifically binding its interaction partner and having the activity of activating the immune response as specified herein above, preferably, the activity of being an antagonist of PD-L1 as specified herein above. Peptide aptamers, preferably, are peptides comprising 8-80 amino acids, more preferably 10-50 amino acids, and most preferably 15-30 amino acids. They can e.g. be isolated from randomized peptide expression libraries in a suitable host system like baker's yeast (see, for example, Klevenz et al., Cell Mol Life Sci. 2002, 59: 1993-1998). A peptide aptamer, preferably, is a free peptide; it is, however, also contemplated by the present invention that a peptide aptamer is fused to a polypeptide serving as "scaffold", meaning that the covalent linking to said polypeptide serves to fix the three-dimensional structure of said peptide aptamer to one specific conformation. More preferably, the peptide aptamer is fused to a transport signal, in particular a peptide export signal.

As used herein, the term "anticalin" relates to an artificial polypeptide derived from a lipocalin specifically binding its interaction partner. Similarly, a "Designed Ankyrin Repeat Protein" or "DARPin", as used herein, is an artificial polypeptide comprising several 14cab14i14 repeat motifs and specifically binding its interaction partner. The anticalins and the DARPins of the present invention have the activity of activating the immune response as specified herein above, preferably, the activity of being an antagonist of PD-L1 as specified herein above.

As used herein, the term "inhibitory peptide" relates to any chemical molecule comprising at least one peptide having the activity of activating the immune response as specified herein above, preferably, the activity of being an antagonist PD-L1 as specified herein above. Preferably, the inhibitory peptide comprises a peptide having an amino acid sequence corresponding to an amino acid sequence of at least five, at least six, at least seven, at least eight, at least nine, at least ten, at least eleven, at least twelve, at least 13, at least 14, or at least 15 consecutive amino acids comprised in a PD-L1 polypeptide. Preferably, the inhibitory peptide comprises a peptide having an amino acid sequence corresponding to an amino acid sequence of 5 to 200, more preferably 6 to 100, even more preferably 7 to 50, or, most preferably, 8 to 30 consecutive amino acids comprised in a PD-L1 polypeptide. Moreover, also encompassed are variants of the aforementioned inhibitory peptides. Such variants have at least the same essential biological activity as the specific inhibitory peptides.

As used herein, the term "immunoglobulin" relates to a polypeptide being a soluble immunoglobulin, preferably an antibody from any of the classes IgA, IgD, IgE, IgG, or IgM, preferably having the activity of binding, more preferably specifically binding, a molecule of interest. Immunoglobulins against antigens of interest can be prepared by well known methods using, e.g., a purified molecule of interest or a suitable fragment derived therefrom as an antigen. A fragment which is suitable as an antigen may be identified by antigenicity determining algorithms well known in the art. Such fragments may be obtained either from one of the molecules of interest by proteolytic digestion, may be a synthetic peptide, or may be obtained by recombinant expression. Preferably, a peptide of a molecule of interest used as an antigen is located at the exterior of a cell expressing the molecule of interest; i.e. preferably, the epitope the binding domain interacts with, preferably, is an extracellular domain. Preferably, the immunoglobulin of the present invention is a monoclonal antibody, a human or humanized antibody or primatized, chimerized antibody or a fragment thereof, so long as they exhibit the desired binding activity as specified elsewhere herein. Also comprised as antibodies of the present invention are a bispecific antibody, a synthetic antibody, or a chemically modified derivative of any of these. Preferably, the antibody of the present invention shall specifically bind (i.e. does only to a negligible extent or, preferably, not cross react with other polypeptides or peptides) to a molecule of interest as specified above. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature. 1975. 256: 495; and Galfré, Meth. Enzymol. 1981, 73: 3, which comprise the fusion of mouse myeloma cells to spleen cells derived from immunized mammals. As will be understood by the skilled person, a molecule of interest, bound by an immunoglobulin of the present invention, may also be an Fc receptor or a complement protein binding an Fc part of an antibody; accordingly, the immunoglobulin preferably is an Fc domain of an antibody, more preferably a soluble Fc domain of an antibody, most preferably a secreted soluble Fc domain of an antibody. Preferably, said antibody the Fc domain is derived from is an IgG, more preferably an IgG1, most preferably a human IgG1. Preferably, the secreted soluble Fc domain comprises the amino acid sequence of SEQ ID NO: 16 or a variant thereof, preferably encoded by the nucleic acid sequence of SEQ ID NO: 17. More preferably, the immunoglobulin is an antagonistic anti-PD-L1 antibody, still more preferably comprising the amino acid sequence of SEQ ID NO:2 or a variant thereof, preferably encoded by a polynucleotide comprising the nucleic acid sequence of SEQ ID NO:3 or a variant thereof. More preferably, the immunoglobulin is an antagonistic anti-PD-L1 antibody, more preferably comprising the amino acid sequence of SEQ ID NO:2, preferably encoded by a polynucleotide comprising the nucleic acid sequence of SEQ ID NO:3.

"Immunoglobulin fragments" comprise a portion of an intact immunoglobulin, preferably of an antibody, in an embodiment, comprise the antigen-binding region thereof. Examples of antibody fragments and fusion proteins of variable regions include Fab, Fab', F(ab')2, and Fv fragments; diabodies; linear antibodies; single-chain antibody molecules; single-domain-antibodies (VHH), also known as nanobodies, and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. "Fv" is the minimum antibody fragment which contains a complete antigen-binding site. Preferably, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs, also referred to as complementarity determining regions (CDRs)) of each variable domain interact to define an antigen-binding site. Collectively, the six HVRs of one scFv confer antigen-binding specificity to the antibody. However, even a single variable domain (or half of an Fv comprising only three HVRs specific for an antigen) has the ability to recognize and bind antigen, although at a lower affinity than the entire binding site. The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson et al., Nat. Med. 9 (2003) 129-134; and Hollinger et al., PNAS USA 90 (1993) 6444-6448. Triabodies and tetrabodies are also described in Hudson et al., Nat. Med. 9 (2003) 129-134.

The term "secreted", as used herein, relates to a compound being transferred from the interior of a host cell to the exterior of said host cell by a mechanism intrinsic to said host cell. Preferably, secretion of a polypeptide or fusion polypeptide is mediated by a, preferably eukaryotic, signal peptide mediating import of said peptide or polypeptide into the lumen of the endoplasmic reticulum and, more preferably, by the absence of retention signals. Signal peptides causing secretion of peptides or polypeptides are known in the art. Preferably, the signal peptide is an IL-12 signal peptide. Also preferably, the signal peptide is or comprises an Ig leader sequence. More preferably, the signal peptide is or comprises a human Ig leader sequence. Still more preferably, the signal peptide is or comprises a matching leader sequence, i.e. a leader sequence selected from the same Ig kappa subgroup as the variable light chain of the antibody, preferably, of the single-chain antibody.

As used herein, the terms "polypeptide variant" relates to any chemical molecule comprising at least one polypeptide or fusion polypeptide as specified elsewhere herein, having the indicated activity, but differing in primary structure from said polypeptide or fusion polypeptide indicated above. Thus, the polypeptide variant, preferably, is a mutein having the indicated activity. Preferably, the polypeptide variant comprises a peptide having an amino acid sequence corresponding to an amino acid sequence of 5 to 200, more preferably 6 to 100, even more preferably 7 to 50, or, most preferably, 8 to 30 consecutive amino acids comprised in a polypeptide as specified above. Moreover, also encompassed are further polypeptide variants of the aforementioned polypeptides. Such polypeptide variants have at least essentially the same biological activity as the specific polypeptides. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the whole length of the polypeptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to herein may be allelic variants or any other species specific homologs, paralogs, or orthologs. Moreover, the polypeptide variants referred to herein include fragments of the specific polypeptides or the aforementioned types of polypeptide variants as long as these fragments and/or variants have the biological activity as referred to above. Such fragments may be or be derived from, e.g., degradation products or splice variants of the polypeptides. Further included are variants which differ due to posttranslational modifications such as phosphorylation, glycosylation, ubiquitinylation, sumoylation, or myristylation, by including non-natural amino acids, and/or by being peptidomimetics.

The term "expressible polynucleotide", as used herein, relates to a polynucleotide operatively linked to at least one expression control sequence causing transcription of the nucleic acid sequence comprised in said polynucleotide to occur, preferably in eukaryotic cells or isolated fractions thereof, preferably into a translatable mRNA or into a viral genome. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Preferably, the aforesaid at least one expression control sequence is an expression control sequence of a (−)strand RNA virus, more preferably of a Paramyxovirus as described herein above, most preferably of an MV. Thus, preferably, at least one expression control sequence comprises a (−)strand RNA viral regulatory sequence ensuring initiation of transcription (consensus "gene start signal", preferably consensus MV "gene start signal") and termination signals (consensus "gene stop signal", preferably, consensus MV "gene stop signal") ensuring termination of transcription and stabilization of the transcript. It is known in the art that production of viral particles in permissive host cells can be initiated by transfecting into said permissive host cells one or more expressible DNA constructs encoding (i) a recombinant viral anti-genome, (ii) the viral L gene, (iii) the viral P gene, and (iv) the viral N gene. It is also understood by the skilled person that, once a viral genome and the aforesaid viral genes were expressed in said host cell, replication and assembly of viral particles occurs in the cytoplasm of the host cell and is, therefore, solely dependent on viral regulatory signals. The term polynucleotide, as used herein, preferably encompasses polynucleotide variants as specified elsewhere herein. Preferably, the expressible polynucleotide encoding an IL-12 is comprised in the genome of the recombinant virus of the family Paramyxoviridae in a region corresponding to the region intervening the P and the M gene of measles virus.

The term "polynucleotide encoding a recombinant virus", as used herein, relates to a polynucleotide comprising a nucleic acid sequence or nucleic acid sequences required for generating a virus particle or a virus-like particle in a host cell. It is understood by the skilled person that a virus is constituted by a polynucleotide genome and at least one kind of capsid polypeptide. Accordingly, the polynucleotide encoding a recombinant virus of the present invention, preferably, comprises a recombinant virus genome. As will be understood by the skilled person, in case the polynucleotide encoding a recombinant virus is comprised in a virus according to the present invention, i.e. a virus of the family Paramyxoviridae, the polynucleotide is (−)strand RNA. It is also understood by the skilled person that in case the polynucleotide is DNA comprised in a host cell, at least an RNA-dependent RNA polymerase activity will additionally be required to produce viral particles from said DNA polynucleotide. Preferably, the polynucleotide encoding a recombinant virus comprises or consists of the nucleic acid sequence as specified elsewhere herein. As annotated herein, the sequence of the DNA copy of negative-strand (−)RNA viruses is annotated in the usual 5'→3'-orientation; this corresponds to the viral sequence in antigenomic (+)RNA orientation with respect to the natural 3'→5'-orientation of negative-strand (−)RNA viruses.

The term "polynucleotide variant", as used herein, relates to a variant of a polynucleotide related to herein comprising a nucleic acid sequence characterized in that the sequence can be derived from the aforementioned specific nucleic acid sequence by at least one nucleotide substitution, addition and/or deletion, wherein the polynucleotide variant shall have the activity as specified for the specific polynucleotide. Preferably, said polynucleotide variant is an ortholog, a paralog or another homolog of the specific polynucleotide. Also preferably, said polynucleotide variant is a naturally occurring allele of the specific polynucleotide. Polynucleotide variants also encompass polynucleotides comprising a nucleic acid sequence which is capable of hybridizing to the aforementioned specific polynucleotides, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of a polypeptide of the present invention. Conserved domains of a polypeptide may be identified by a sequence comparison of the nucleic acid sequence of the polynucleotide or the amino acid sequence of the polypeptide of the present invention with sequences of other organisms. As a template, DNA or cDNA from bacteria, fungi, or plants preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))), which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences is also encompassed as a variant polynucleotide of the present invention. The fragment shall still encode a polypeptide or fusion polypeptide which still has the activity as specified. Accordingly, the polypeptide encoded may comprise or consist of the domains of the polypeptide of the present invention conferring the said biological activity. A fragment as meant herein, preferably, comprises at least 50, at least 100, at least 250 or at least 500 consecutive nucleotides of any one of the specific nucleic acid sequences or encodes an amino acid sequence comprising at least 20, at least 30, at least 50, at least 80, at least 100 or at least 150 consecutive amino acids of any one of the specific amino acid sequences.

The polynucleotides of the present invention either consist of, essentially consist of, or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and are described elsewhere herein.

The polynucleotide of the present invention shall be provided, preferably, either as an isolated polynucleotide (i.e. isolated from its natural context) or in genetically modified form. The polynucleotide, preferably, is DNA, including cDNA, or RNA. The term encompasses single as well as double stranded polynucleotides. Moreover, preferably, comprised are also chemically modified polynucleotides including naturally occurring modified polynucleotides such as glycosylated or methylated polynucleotides or artificial modified one such as biotinylated polynucleotides.

As used herein, the term "host cell" relates to a vertebrate cell. Preferably, the cell is a mammalian cell, more preferably, a mouse, rat, cat, dog, hamster, guinea pig, sheep, goat, pig, cattle, or horse cell. Still more preferably, the host cell is a primate cell. Most preferably, the host cell is a human cell. Preferably, the host cell is a tumor cell, more preferably a cancer cell.

Advantageously, it was found in the work underlying the present invention that oncolytic measles virus can be engineered to express IL-12, in particular an IL-12 fusion polypeptide, while infecting cancer cells and that IL-12 expression strongly enhances the immune response induced by the measles virus against said cancer cells. Moreover, it was found that by further expressing immunoglobulins, in particular an anti-PD-L1 antibody, measles virus can further augment the immunological response to cancer cells, thus further contributing to their elimination.

The definitions made above apply mutatis mutandis to the following. Additional definitions and explanations made further below also apply for all embodiments described in this specification mutatis mutandis.

The present invention further relates to a polynucleotide encoding the recombinant virus of the family Paramyxoviridae according to the present invention.

The present invention further relates to a host cell comprising the recombinant virus of the family Paramyxoviridae of the present invention and/or the polynucleotide encoding the recombinant virus of the family Paramyxoviridae of the present invention.

As used herein, the term "host cell" relates to a host cell as specified herein above. Moreover, the host cell comprising the polynucleotide encoding the recombinant virus of the family Paramyxoviridae of the present invention may also be a bacterial, yeast, or insect cell, preferably a bacterial cell of the genus *Escherichia*, more preferably an *Escherichia coli* cell.

The present invention also relates to a medicament comprising (a) (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist; (ii) a recombinant virus of the family Paramyxoviridae comprising an expressible polynucleotide encoding an IL-12 fusion polypeptide of the present invention; (iii) a polynucleotide encoding the recombinant virus of the family Paramyxoviridae of (i) and/or (ii), (iv) a host cell comprising the recombinant virus of the family Paramyxoviridae and/or the polynucleotide encoding the recombinant virus of the family Paramyxoviridae according to; or (v) any combination of (i) to (iv); and (b) at least one pharmacologically acceptable excipient.

The terms "medicament" and "pharmaceutical composition", as used herein, relate to the compounds of the present invention and optionally one or more pharmaceutically acceptable carrier, i.e. excipient. The compounds of the present invention can be formulated as pharmaceutically acceptable salts. Acceptable salts comprise acetate, methyl ester, HCl, sulfate, chloride and the like. The pharmaceutical compositions are, preferably, administered locally, topically or systemically. Suitable routes of administration conventionally used for drug administration are oral, intravenous, or parenteral administration as well as inhalation. A preferred route of administration is intra-tumoral administration. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The excipient(s) must be acceptable in the sense of being compatible with the other ingredients of the formulation and being not deleterious to the recipient thereof. The excipient employed may be, for example, a solid, a gel or a liquid carrier. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 μg for a polypeptide or polynucleotide, or $10^4$-$10^8$ viral particles for a virus or a virus-like particle; however, doses below or above this exemplary range are envisioned, especially considering the aforementioned factors. Progress can be monitored by periodic assessment. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

Accordingly, the present invention also relates to a method for treating cancer in a subject afflicted with cancer, comprising a) contacting said subject with
   (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;
   (ii) a recombinant virus of the family Paramyxoviridae comprising an expressible polynucleotide encoding an IL-12 fusion polypeptide of the present invention;
   (iii) a polynucleotide encoding the recombinant virus of the family Paramyxoviridae of (i) and/or (ii),
   (iv) a host cell comprising the recombinant virus of the family Paramyxoviridae of (i) and/or (ii) and/or the polynucleotide encoding the recombinant virus of the family Paramyxoviridae according to (iii); or
   (v) any combination of (i) to (iv), and thereby,
b) treating cancer in a subject afflicted with cancer.

The methods of treatment of the present invention, preferably, may comprise steps in addition to those explicitly mentioned above. For example, further steps may relate, e.g., to localizing a tumor and/or diagnosing cancer for step a), or administration of additional medication for step b). Moreover, one or more of said steps may be performed by automated equipment. The method of the present invention, preferably, is an in vivo method of treatment.

The term "treatment" refers to an amelioration of the diseases or disorders referred to herein or the symptoms accompanied therewith to a significant extent. Said treating as used herein also includes an entire restoration of the health with respect to the diseases or disorders referred to herein. It is to be understood that treating as used in accordance with the present invention may not be effective in all subjects to be treated. However, the term shall require that, preferably, a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20% at least 50% at least 60%, at least 70%, at least 80%, or at least 90% of the subjects of a given cohort or population. Preferably, treating cancer is reducing tumor burden in a subject. As will be understood by the skilled person, effectiveness of treatment of e.g. cancer is dependent on a variety of factors including, e.g. cancer stage and cancer type.

As used herein, the term "subject" relates to a vertebrate. Preferably, the subject is a mammal, more preferably, a mouse, rat, cat, dog, hamster, guinea pig, sheep, goat, pig, cattle, or horse. Still more preferably, the subject is a primate. Most preferably, the subject is a human. Preferably, the subject is afflicted with a disease caused or aggravated by an insufficient response of the immune response of said subject, more preferably, the subject is afflicted with cancer.

The term "cancer", as used herein, relates to a disease of an animal, including man, characterized by uncontrolled growth by a group of body cells ("cancer cells"). This uncontrolled growth may be accompanied by intrusion into and destruction of surrounding tissue and possibly spread of cancer cells to other locations in the body. Preferably, also included by the term cancer is a relapse. Thus, preferably, the cancer is a solid cancer, a metastasis, or a relapse thereof.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, fibrosarcoma, gallbladder cancer, gastric cancer, gastrointestinal stromal tumor, gestational trophoblastic tumor, hairy cell leukemia, head and neck cancer, hepatocellular cancer, 27cab27i27 lymphoma, hypopharyngeal cancer, hypothalamic and visual pathway glioma, intraocular melanoma, 27cab27i sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenström macroglobulinemia, and wilms tumor. More preferably, the cancer is a solid cancer, a metastasis, or a relapse thereof. Most preferably, the cancer is a tumor derived from malignant melanoma, head and neck cancer, hepatocellular carcinoma, pancreatic carcinoma, prostate cancer, renal cell carcinoma, gastric carcinoma, colorectal carcinoma, lymphomas or leukemias.

Preferably, the method of treatment of the present invention comprises contacting a subject with a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist. Thus, preferably, the method comprises contacting a subject with a recombinant virus of the family Paramyxoviridae comprising an expressible polynucleotide encoding an IL-12, wherein said recombinant virus of the family Paramyxoviridae is not a virus disclosed in WO 2015/128313 A1. Preferably, said recombinant virus of the family Paramyxoviridae of (i) is a recombinant virus of the family Paramyxoviridae comprising an expressible polynucleotide encoding an IL-12 polypeptide and not comprising an expressible polynucleotide encoding a ligand for an immune checkpoint blockade protein. More preferably, the recombinant virus of the family Paramyxoviridae of (i) is a recombinant virus of the family Paramyxoviridae comprising an expressible polynucleotide encoding an IL-12 polypeptide as the only expressible polynucleotide encoding an activator of the immune response, i. e. preferably, the recombinant virus of the family Paramyxoviridae comprising an expressible polynucleotide encoding an IL-12 does not comprise an expressible polynucleotide encoding a further activator of the immune response.

The present invention further relates to an in vitro method for activating immune cells with antitumor activity in a sample comprising cancer cells and immune cells, comprising a) contacting said sample comprising cancer cells and immune cells with (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;

(ii) a recombinant virus of the family Paramyxoviridae comprising an expressible polynucleotide encoding an IL-12 fusion polypeptide of the present invention;

(iii) a polynucleotide encoding the recombinant virus of the family Paramyxoviridae of (i) and/or (ii), (iv) a host cell comprising the recombinant virus of the family Paramyxoviridae of (i) and/or (ii) and/or the polynucleotide encoding the recombinant virus of the family Paramyxoviridae according to (iii); or (v) any combination of (i) to (iv), and thereby, b) activating immune cells with antitumor activity comprised in said sample.

The method for activating immune cells with antitumor activity may comprise steps in addition to those explicitly mentioned above. For example, further steps may relate, e.g., to providing the recombinant virus of the family Paramyxoviridae for step a), administering further activating compounds, e.g. cytokines, to the immune cells in step b), or separating immune cells from cancer cells after step b). Moreover, one or more of said steps may be performed by automated equipment.

Moreover, the present invention relates to a recombinant virus of the family Paramyxoviridae of the present invention for use in treatment of inappropriate cell proliferation.

The term "inappropriate cell proliferation" relates to any proliferation of cells of a subject which is not appropriate to the physiological state of said subject and/or to the tissue context of said cells. Preferably, inappropriate cell proliferation is caused or aggravated by an inhibition or insufficient activation of the immune system, more preferably inhibition or insufficient activation of T cells. Also preferably, inappropriate cell proliferation is cancer.

The present invention further relates to a kit comprising at least (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;

(ii) a recombinant virus of the family Paramyxoviridae comprising an expressible polynucleotide encoding an IL-12 fusion polypeptide of the present invention;

(iii) a polynucleotide encoding the recombinant virus of the family Paramyxoviridae of (i) and/or (ii), (iv) a host cell comprising the recombinant virus of the family Paramyxoviridae of (i) and/or (ii) and/or the polynucleotide encoding the recombinant virus of the family Paramyxoviridae according to (iii); or (v) any combination of (i) to (iv), housed in a container.

The term "kit", as used herein, refers to a collection of the aforementioned components. Preferably, said components are combined with additional components, preferably within an outer container. The outer container, also preferably, comprises instructions for carrying out a method of the present invention. Examples for such the components of the kit as well as methods for their use have been given in this specification. The kit, preferably, contains the aforementioned components in a ready-to-use formulation. Preferably, the kit may additionally comprise instructions, e.g., a user's manual for applying the recombinant virus of the family Paramyxoviridae with respect to the applications provided by the methods of the present invention. Details are to be found elsewhere in this specification. Additionally, such user's manual may provide instructions about correctly using the components of the kit. A user's manual may be provided in paper or electronic form, e.g., stored on CD or CD ROM. The present invention also relates to the use of said kit in any of the methods according to the present invention.

Moreover, the present invention relates to a use of (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;

(ii) a recombinant virus of the family Paramyxoviridae comprising an expressible polynucleotide encoding an IL-12 fusion polypeptide of the present invention;

(iii) a polynucleotide encoding the recombinant virus of the family Paramyxoviridae of (i) and/or (ii), (iv) a host cell comprising the recombinant virus of the family Paramyxoviridae of (i) and/or (ii) and/or the polynucleotide encoding the recombinant virus of the family Paramyxoviridae according to (iii); or (v) any combination of (i) to (iv), for the manufacture of a medicament for treating inappropriate cell proliferation, preferably for treating cancer.

Summarizing the findings of the present invention, the following embodiments are preferred:

1. A recombinant virus of the family Paramyxoviridae, comprising an expressible polynucleotide encoding an IL-12 polypeptide, wherein said IL-12 polypeptide is an IL-12 fusion polypeptide comprising a p40 subunit of an IL-12 and a p35 subunit of an IL-12.

2. The recombinant virus of the family Paramyxoviridae of embodiment 1, wherein said p40 subunit and said p35 subunit of said IL-12 fusion polypeptide are from the same species.

3. The recombinant virus of the family Paramyxoviridae of embodiment 1 or 2, wherein said p40 subunit and said p35 subunit of said IL-12 fusion polypeptide are a mouse p40 subunit and a mouse p35 subunit or a variant thereof, preferably are a human p40 subunit and a human p35 subunit or a variant thereof.

4. The recombinant virus of the family Paramyxoviridae of any one of embodiments 1 to 3, wherein said p40 subunit and said p35 subunit of said IL-12 fusion polypeptide are a Claim subunit and a mouse p35 subunit, preferably are a human p40 subunit and a human p35 subunit.

5. The recombinant virus of the family Paramyxoviridae of any one of embodiments 1 to 4, wherein said IL-12 fusion polypeptide comprises the structure p40-linker-p35.

6. The recombinant virus of the family Paramyxoviridae of any one of embodiments 1 to 5, wherein said linker is -(glycine$_4$-serine)$_n$-, with n=1 to 10, preferably n=2 to 5, more preferably n=3.

7. The recombinant virus of the family Paramyxoviridae of any one of embodiments 1 to 5, wherein said linker is -(glycine$_6$-serine)-.

8. The recombinant virus of the family Paramyxoviridae of any one of embodiments 1 to 7, wherein said expressible polynucleotide encoding an IL-12 is comprised in the genome of the recombinant virus of the family Paramyxoviridae in a region corresponding to the region intervening the P and the M gene of measles virus.

9. The recombinant virus of the family Paramyxoviridae of any one of embodiments 1 to 8, further comprising at least one expressible polynucleotide encoding a further activator of the immune response.

10. The recombinant virus of the family Paramyxoviridae of embodiment 9, wherein said further activator of the immune response is an immunoglobulin or fragment thereof.

11. The recombinant virus of the family Paramyxoviridae of embodiments 9 or 10, wherein said further activator of the immune response is a secreted immunoglobulin.

12. The recombinant virus of the family Paramyxoviridae of any one of embodiments 9 to 11, wherein said further activator of the immune response is an Fc domain of an antibody.

13. The recombinant virus of the family Paramyxoviridae of any one of embodiments 9 to 12, wherein said further activator of the immune response is a secreted soluble Fc domain of a human IgG1 antibody.

14. The recombinant virus of the family Paramyxoviridae of any one of embodiments 9 to 13, wherein said further activator of the immune response is a secreted soluble activator of the immune response.

15. The recombinant virus of the family Paramyxoviridae of any one of embodiments 9 to 14, wherein said further activator of the immune response is a single-chain antibody or a nanobody.

16. The recombinant virus of the family Paramyxoviridae of any one of embodiments 9 to 15, wherein said further activator of the immune response is a secreted soluble anti-PD-L1 antibody.

17. The recombinant virus of the family Paramyxoviridae of embodiment 16, wherein said secreted soluble anti-PD-L1 antibody comprises an amino acid sequence according to SEQ ID NO: 2.

18. The recombinant virus of the family Paramyxoviridae of any one of embodiments 1 to 17, wherein said recombinant virus is a recombinant Morbillivirus, preferably, a recombinant measles virus (MV).

19. The recombinant virus of the family Paramyxoviridae of any one of embodiments 1 to 18, wherein said recombinant MV is derived from MV strain Edmonston A or B, preferably B, more preferably from MV vaccine strain Schwarz/Moraten.

20. The recombinant virus of the family Paramyxoviridae of any one of embodiments 1 to 19, wherein the at least one expressible polynucleotide encoding an IL-12 polypeptide is comprised in a polynucleotide encoding the recombinant virus of the family Paramyxoviridae.

21. The recombinant virus of the family Paramyxoviridae of any one of embodiments 1 to 20, wherein said polynucleotide encoding the recombinant virus of the family Paramyxoviridae comprises the nucleic acid sequence of any one of SEQ ID Nos: 4 to 7, 14, and 15.

22. A polynucleotide encoding the recombinant virus of the family Paramyxoviridae according to any one of embodiments 1 to 21.

23. The polynucleotide according to embodiment 22, wherein said polynucleotide comprises the nucleic acid sequence any one of SEQ ID Nos: 4 to 7, 14, and 15.

24. A host cell comprising the recombinant virus of the family Paramyxoviridae according to any one of embodiments 1 to 21 and/or the polynucleotide encoding the recombinant virus of the family Paramyxoviridae according to embodiment 21 or 22.

25. A medicament comprising (a) (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;
  - (ii) a recombinant virus of the family Paramyxoviridae according of any one of embodiments 1 to 21,
  - (iii) a polynucleotide encoding the recombinant virus of the family Paramyxoviridae of (i) and/or (ii),
  - (iv) a host cell comprising the recombinant virus of the family Paramyxoviridae according to (i) or (ii) and/or a polynucleotide encoding the recombinant virus of the family Paramyxoviridae of (iii); or
  - (v) any combination of (i) to (iv); and (b) at least one pharmacologically acceptable excipient.

26. A method for treating cancer in a subject afflicted with cancer, comprising a) contacting said subject with
  - (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;
  - (ii) a recombinant virus of the family Paramyxoviridae according of any one of embodiments 1 to 21,
  - (iii) a polynucleotide encoding the recombinant virus of the family Paramyxoviridae of (i) and/or (ii),
  - (iv) a host cell comprising the recombinant virus of the family Paramyxoviridae according to (i) or (ii) and/or a polynucleotide encoding the recombinant virus of the family Paramyxoviridae of (iii); or
  - (v) any combination of (i) to (iv); and, thereby, b) treating cancer in a subject afflicted with cancer.

27. The method of embodiment 26, wherein said recombinant virus of the family Paramyxoviridae of (i) is a recombinant virus of the family Paramyxoviridae comprising an expressible polynucleotide encoding an IL-12 polypeptide and not comprising an expressible polynucleotide encoding a ligand for an immune checkpoint blockade protein.

28. The method of embodiment 26 or 27, wherein said recombinant virus of the family Paramyxoviridae of (i) is a recombinant virus of the family Paramyxoviridae comprising an expressible polynucleotide encoding an IL-12 polypeptide as the only expressible polynucleotide encoding an activator of the immune response.

29. The method of any one of embodiments 26 to 28, wherein said cancer is a solid cancer, a metastasis, or a relapse thereof.

30. The method of any one of embodiments 26 to 29, wherein treating cancer is reducing tumor burden.

31. The method of any one of embodiments 26 to 30, wherein said cancer is malignant melanoma, head and neck cancer, hepatocellular carcinoma, pancreatic carcinoma, prostate cancer, renal cell carcinoma, gastric carcinoma, colorectal carcinoma, lymphomas or leukemias.

32. An in vitro method for activating immune cells with antitumor activity in a sample comprising cancer cells and immune cells, comprising a) contacting said sample comprising cancer cells and immune cells with
  - (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;
  - (ii) a recombinant virus of the family Paramyxoviridae according of any one of embodiments 1 to 21,
  - (iii) a polynucleotide encoding the recombinant virus of the family Paramyxoviridae of (i) and/or (ii),
  - (iv) a host cell comprising the recombinant virus of the family Paramyxoviridae according to (i) or (ii) and/or a polynucleotide encoding the recombinant virus of the family Paramyxoviridae of (iii); or
  - (v) any combination of (i) to (iv); and thereby, b) activating immune cells with antitumor activity comprised in said sample.

33. Use of (i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;

(ii) a recombinant virus of the family Paramyxoviridae according of any one of embodiments 1 to 21, (iii) a polynucleotide encoding the recombinant virus of the family Paramyxoviridae of (i) and/or (ii), (iv) a host cell comprising the recombinant virus of the family Paramyxoviridae according to (i) or (ii) and/or a polynucleotide encoding the recombinant virus of the family Paramyxoviridae of (iii); or (v) any combination of (i) to (iv);

for the manufacture of a medicament for treating cancer.

34. A recombinant virus of the family Paramyxoviridae according to any one of embodiments 1 to 21 and/or a polynucleotide according to embodiment 22 or 23 for use in medical treatment.

35. A recombinant virus of the family Paramyxoviridae
(i) comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist; and/or
(ii) according of any one of embodiments 1 to 21, for use in treatment of inappropriate cell proliferation.

36. The recombinant virus of the family Paramyxoviridae for use of embodiment 35, wherein treatment of inappropriate cell proliferation is cancer treatment.

37. A kit comprising
(i) a recombinant virus of the family Paramyxoviridae comprising an expressible polynucleotide encoding an IL-12 and not comprising an expressible polynucleotide encoding a CTLA-4 antagonist, a PD-1 antagonist, a CD80 antagonist, a CD86 antagonist, or a PD-L1 antagonist;
(ii) a recombinant virus of the family Paramyxoviridae according of any one of embodiments 1 to 21,
(iii) a polynucleotide encoding the recombinant virus of the family Paramyxoviridae of (i) and/or (ii),
(iv) a host cell comprising the recombinant virus of the family Paramyxoviridae according to (i) or (ii) and/or a polynucleotide encoding the recombinant virus of the family Paramyxoviridae of (iii); or
(v) any combination of (i) to (iv);
housed in a container.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

EXAMPLES

Example 1: Cell Culture

Vero African green monkey kidney cells were obtained from the American Type Culture Collection (Manassas, Va.). Vero-αHis cell line stably expressing a single chain antibody (38cab) against $His_6$ tag (Nakamura et al. 2005) was a kind gift of S. J. Russel (Mayo Clinic, Rochester, Minn.). Murine colon adenocarcinoma cells MC38cea (transduced for stable expression of human CEA antigen) and the parental MC38 cell line were a gift of R. Cattaneo (Mayo Clinic, Rochester, Minn.). B16-CD20 have previously been generated by transducing the parental cell line with a lentiviral vector encoding human CD20 (Engeland et al. 2014). All cell lines were cultivated in either Dulbecco's modified Eagle's medium (DMEM; Life Technologies, Darmstadt, Germany) or Roswell Park Memorial Institute 1640 medium (RPMI 1640; Life Technologies) supplemented with 10% Fetal Calf Serum (FCS) at 37° C. in a humidified atmosphere with 5% $CO_2$ and routinely tested for mycoplasma contamination.

Example 2: Cloning of Recombinant MeVac Genomes

The cDNA plasmids encoding recombinant MeV genomes were constructed on the basis of the commercially used Schwarz/Moraten vaccine strain (MeVac) (Combredet et al. 2003). Transgenes were inserted in additional transcription units (ATUs) containing additional gene-end gene-start signals and a unique cloning site. Transgenes smaller than 1 kbp including murine GM-CSF (426 bp), murine IP-10 (312 bp) and eGFP (720 bp) were inserted into the leader position of pcMeVac as MluI-AscI fragments via the unique AscI restriction site. The mGM-CSF and eGFP fragments were amplified from the MeV Edmonston B (Nse) vaccine strain genomes encoding the respective transgenes (Grossardt et al. 2013). The mIP-10 (mCxcl10) gene was amplified with primers flanking the novel construct and adding a MluI site and a Kozak sequence (GCCACC) in the 5'-end and a two nucleotide TA spacer and AscI site in the 3'-end using cDNA obtained from murine splenocytes.

Cassette encoding a murine IL-12 fusion protein (FmIL-12) consisting of murine IL-12 p40 and p35 subunits linked by a $(Gly_4Ser)_3$ for insertion into MeV genome had previously been constructed by C. Grossardt (Grossardt 2013) based on results of Lieschke and colleagues (Lieschke et al. 1997). FmIL-12 construct (1650 bp) was excised from pCG expression vector (constructed by C. Grossardt) as PauI-MluI fragment and inserted into the MeVac genome downstream the P ORF via the unique MauBI cloning site.

Antibodies against negative murine T cell regulators CTLA-4 and PD-L1 as well as soluble form of murine CD80 T cell costimulatory molecule and human IgG1-Fc fragment for use as a control were inserted into the ATU downstream the H gene. Cassettes encoding antibodies against murine CTLA-4 and PD-L1 and human IgG1-Fc fragment previously designed by C. E. Engeland (Engeland et al. 2014) were used as templates. The respective constructs were excised from pCG expression vectors as MluI-PauI fragments and inserted into the pcMeVac H-ATU via the unique MauBI cloning site.

Murine CD80 molecule was inserted for expression from MeVac in a soluble form. CD80-Fc was constructed by fusing the extracellular part of the murine CD80 with the same human IgG1-Fc region as used in both anti-CTLA-4 and anti-PD-L1 constructs via fusion PCR. The first PCR fragment consisting of the MluI restriction site followed by Kozak sequence (GCCACC), murine CD80 signal peptide, extracellular part (up to the asparagine in position 246) of murine CD80 and first 26 nucleotides of the hinge of IgG1-Fc was synthesized using pCG vector encoding murine CD80 as a template. The second PCR fragment consisting of the human IgG1-Fc region followed by myc tag, stop codon and AscI restriction site was synthesized using pCG vector encoding human IgG1-Fc as a template. The obtained PCR products were fused with flanking primers in an overlap PCR obtaining the mCD80-Fc construct of 1614 bp. The mCD80-Fc was inserted into the pcMeVac H-ATU as a MluI-AscI fragment via the unique MauBI cloning site.

MeVac genomes encoding the previously described transgenes with a fully retargeted MeV H attachment gene were constructed to allow targeted transduction of murine MC38cea and B16-CD20 cells. MeVac H gene was exchanged for H gene with mutated attachment sites to the natural MeV receptors CD46 and CD150, fused to a single chain antibody (39cab) against human CEA or CD20 and containing a C-terminal $His_6$tag. The retargeting system allows a flexible change of the targeted antigen by exchanging the specific 39cab as a SfiI-NotI fragment.

Example 3: Virus Propagation and Titration

Recombinant MeVac particles were obtained from cDNA constructs according to Radecke et al. (Radecke et al. 1995)

and propagated on Vero-αHis cells according to Nakamura et al. (Nakamura et al. 2005). For propagation Vero-αHis cells were infected at a multiplicity of infection (MOI) of 0.03 and cultivated at 37° C. 5% $CO_2$ until syncytia had spread across the whole cell layer (36-48 h post infection). Subsequently culture medium was completely removed, cells were scraped and collected and viral particles released by one freeze-thaw cycle. Cellular debris was removed by centrifugation at 6000×g for 5 min. The amount of viral particles was determined by 1:10 serial dilution titrations in octuplicates on $1.5\times10^4$Vero-αHis cells per well in 96-well cell culture plates. Individual syncytia were counted 72 h post infection and titers calculated as cell infectious units per ml (ciu/ml).

Example 4: Statistical Analyses

Statistical analyses were performed using GraphPad Prism software (version 5.04; GraphPad Software, La Jolla, Calif.). Tumor volumes and ELISA results in restimulation experiments were analysed by one-way ANOVA with Tukey's multiple comparison test. Survival curves were analyzed by log-rank (Mantel-Cox) test with Bonferroni-Holm correction for multiple comparisons. Result was considered statistically significant if p value was lower than 0.05 after correcting for multiple comparisons.

Example 5: Characterization of Virus Replication

Vero-αHis and MC38cea cells were seeded in 12-well plates ($1\times10^5$ cells per well). After 12 h the cell culture medium was removed and cells were infected with the respective viruses at MOI=3 in 300 μl OptiMEM in triplicates for each time point and cultivated at 37° C. 5% $CO_2$. After adsorption for ca. 2 h the inoculum was removed and substituted with 1 ml DMEM+10% FCS per well. Cells were scraped in the culture medium at the designated time points, collected and snap frozen in liquid nitrogen. The amount of viral particles was determined by 1:10 serial dilution titrations in quadruplicates on $1.5\times10^4$ Vero-αHis cells per well in 96-well cell culture plates. Individual syncytia were counted 72 h post infection and titers calculated as ciu/ml.

Example 6: Assessment of Virus Cytotoxic Potential In Vitro

MC38cea cells were seeded in 6-well plates ($2\times10^5$ cells per well). After 12 h the cell culture medium was removed and cells were infected with the respective viruses at MOI=5 in 800 μl OptiMEM in triplicates for each time point and cultivated at 37° C. 5% $CO_2$. After adsorption for ca. 2 h the inoculum was removed and substituted with 2 ml DMEM+10% FCS per well. At the designated time points cell viability was determined using Colorimetric Cell Viability Kit III (XTT) (PromoKine, Heidelberg, Germany) according to instructions of the manufacturer.

Example 7: Characterization of Transgene Expression

MC38cea cells were seeded in 12-well plates ($1\times10^5$ cells per well). After 12 h the cell culture medium was removed and cells were infected with the respective viruses at MOI=3 in 300 μl OptiMEM in triplicates for each time point and cultivated at 37° C. 5% $CO_2$. After adsorption for ca. 2 h 700 μl DMEM+10% FCS per well was added. Supernatants were collected at the designated time points. Time point 0 h was represented by inoculum in OptiMEM used for infection. Expression of the respective immunomodulators was detected by ELISA. Commercially available ELISA kits were used for detection of mGM-CSF, FmIL-12, mIP-10 (R&D Systems, Wiesbaden, Germany) and CD80-Fc (Boster Biological Technology, Offenbach, Germany) according to instructions of the manufacturer. Anti-CTLA-4 and anti-PD-L1 were detected by binding to their respective murine proteins. Ninety-six well plates (Nunc Maxisorp, Thermo Fisher Scientific, Schwerte, Germany) were coated with 100 ng recombinant His-tagged murine CTLA-4 or PD-L1 (Life Technologies). Wells were blocked and 100 μl of the respective samples were added and incubated for 2 h. After washing the antibodies were detected with anti-human IgG-Fc Biotin (clone HP-6071; Sigma-Aldrich, Taufkirchen, Germany), Peroxidase conjugated Streptavidin (Dianova, Hamburg, Germany) and 1-Step Ultra-TMB ELISA Substrate Solution (Thermo Scientific, Karlsruhe, Germany). Absorbance was measured using Infinite M200 Pro microplate reader and i-control software (Tecan, Mannedorf, Switzerland).

Example 8: Flow Cytometry for Detection of Anti-PD-L1 Binding to MC38cea Cells Vero-αHis cells were seeded in 15 cm cell culture dishes and infected with MeVac encoding anti-PD-L1 or IgG1-Fc with M01=0.03. Supernatants were collected (15 ml per plate) when syncytia had spread over the whole cell layer (ca. 36 h post infection). $1\times10^6$ MC38cea cells were incubated with anti-PD-L1 or IgG1-Fc containing supernatant previously collected from one fully infected 15 cm dish for 1 h with rotation at room t°. After washing the bound anti-PD-L1 was detected by staining with anti-HA (clone HA-7; Sigma-Aldrich) and goat anti-mouse IgG PE (polyclonal; BD Biosciences, Heidelberg, Germany). The stained cells were resuspended in DPBS with 0.2 μg/ml DAPI (Sigma-Aldrich) and directly acquired on LSRII flow cytometer (BD Biosciences) collecting at least 10000 events per sample.

Example 9: Isolation of Murine Splenocytes

Spleens were aseptically isolated and maintained in RPMI 1640 (Life Technologies, Darmstadt, Germany) at 4° C. until further processing. Spleen was passed through a 100 μm nylon cell strainer (BD Biosciences, Heidelberg, Germany) into 10 ml RPMI 1640 and cells were pelleted at 300×g for 5 min. For red blood cell lysis pellet was resuspended in 1 ml ACK Lysing solution (Life Technologies), incubated 10 min at room t° and centrifuged at 300×g for 5 min. Cells were resuspended in DPBS (Life Technologies) and cell concentration determined using Neubauer hemocytometer and Trypan blue (Sigma-Aldrich) staining for dead cell exclusion.

Example 10: Functional Assay for MeVac Encoded Anti-PD-L1, CD80-Fc and Anti-CTLA-4

Vero-αHis cells were seeded in 15 cm cell culture dishes and infected with MeVac encoding anti-PD-L1, anti-CTLA-4, CD80-Fc or IgG1-Fc with M01=0.03. Supernatants were collected (15 ml per plate) when syncytia had spread over the whole cell layer (ca. 36 h post infection). $2\times10^5$ MC38cea cells were incubated with 2 ml medium collected from the Vero-αHis infected with the respective viruses for 5 min with rotation at room t° and pelleted by centrifugation 5 min at 300×g. The procedure was repeated six times. The treated cells were resuspended in 100 μl activation medium—RPMI 1640 supplemented with 5% FCS, 1% Penicillin-Streptomycin (Life Technologies), 500 μM ionomycin (Cayman Chemical Company, Hamburg, Germany) and 5 μM PMA (Cayman Chemical Company) and seeded in 96-well plate. $2\times10^5$ freshly isolated splenocytes from C57BL/6J mouse in 100 μl activation medium were added per each well with the treated MC38cea cells. Cells were cocultivated 24 h at 37° C. 5% $CO_2$ and supernatants collected subsequently. IFN-γ concentration was determined using mouse IFN gamma ELISA Ready-SET-Go!® (eBioscience, Frankfurt am Main, Germany) according to the instructions of the manufacturer.

Example 11: Functional Assay for MeVac Encoded FmIL-12

Vero-αHis cells were seeded in 15 cm cell culture dishes and infected with MeVac encoding FmIL-12 or eGFP. Supernatants were collected (15 ml per plate) when syncytia had spread over the whole cell layer (ca. 36 h post infection). FmIL-12 concentration was assessed using Mouse IL-12 p70 Quantikine ELISA Kit (R&D Systems). $2\times10^6$ freshly isolated splenocytes from a C57BL/6J mouse were resuspended in RPMI 1640 supplemented with 10% FCS, 1% Penicillin-Streptomycin solution and 50 U/ml recombinant murine IL-2 (Miltenyi, Bergisch Gladbach, Germany) with varying concentrations of MeVac encoded FmIL-12 or respective parts of supernatant from cells infected with eGFP encoding MeVac. Splenocytes were seeded in 12-well plates and incubated 48 h at 37° C. 5% $CO_2$. Supernatants were collected and IFN-γ concentration assessed using mouse IFN gamma ELISA Ready-SET-Go!® (eBioscience) according to the instructions of the manufacturer.

Example 12: Assessment of Therapeutic Efficacy In Vivo

MC38cea cells were subcutaneously (s.c.) implanted into six to eight weeks old C57Bl/6J mice (Harlan Laboratories, Rossdorf Germany or DKFZ, Heidelberg, Germany). When average tumor volume reached 50-100 $mm^3$ (depending on experiment) treatment was initiated. Mice received intratumoral (i.t.) injections with the respective viruses on four or five consecutive days with $5\times10^5$ or $1\times10^6$ ciu in 100 μl. Mice in the mock group received treatment with 100 μl OptiMEM. Tumor volume was determined every third day measuring largest and smallest diameter with a caliper and calculating the volume using a formula: largest diameter×(smallest diameter)$^2$×0.5. Mice were sacrificed when tumor volume exceeded 1500 $mm^3$, ulceration occurred or signs of severe illness were observed.

Example 13: Antigen Specific IFN-γ Memory Recall with Murine Splenocytes

MC38cea, MC38 and B16 cells were treated with 20 μg/ml mitomycin-C(Sigma-Aldrich) for 2 h with shaking at 37° C. After subsequent washing three times with DPBS cells were resuspended in activation medium containing RPMI 1640 supplemented with 10% FCS, 1% Penicillin-Streptomycin and 50 U/ml recombinant murine IL-2. Freshly isolated murine splenocytes were resuspended in the same activation medium. Cocultures were prepared in 24-well plates seeding $1\times10^5$ mitomycin-c treated tumor cells or $1\times10^6$ ciu MeVac with $1\times10^6$ splenocytes per well in 0.5 ml total volume of activation medium. As controls $1\times10^6$ splenocytes were cocultivated also with Vero-αHis or DLD-1 cell lysates prepared by lysis of $1\times10^6$ cells per ml with one freeze-thaw cycle. Cells were cocultivated for 48 h, supernatants collected and IFN-γ concentration assessed using mouse IFN gamma ELISA Ready-SET-Go!® (eBioscience) according to the instructions of the manufacturer.

REFERENCES

Combredet, C. et al., 2003. A Molecularly Cloned Schwarz Strain of Measles Virus Vaccine Induces Strong Immune Responses in Macaques and Transgenic Mice A Molecularly Cloned Schwarz Strain of Measles Virus Vaccine Induces Strong Immune Responses in Macaques and Transgenic Mice.

Engeland, C. E. et al., 2014. CTLA-4 and PD-L1 Checkpoint Blockade Enhances Oncolytic Measles Virus Therapy. *Molecular Therapy,* 22(11), pp. 1949-1959.

Grossardt, C., 2013. *Engineering Targeted and Cytokine-armed Oncolytic Measles Viruses*. Ruperto-Carola University of Heidelberg.

Grossardt, C. et al., 2013. Granulocyte-Macrophage Colony-Stimulating Factor-Armed Oncolytic Measles Virus Is an Effective Therapeutic Cancer Vaccine. *Human Gene Therapy,* 24(7), pp. 644-654.

Lieschke, G. J. et al., 1997. Bioactive murine and human interleukin-12 fusion proteins which retain antitumor activity in vivo. *Nature biotechnology,* 15(1), pp. 35-40.

Nakamura, T. et al., 2005. Rescue and propagation of fully retargeted oncolytic measles viruses. *Nature biotechnology,* 23(2), pp. 209-14.

Radecke, F. et al., 1995. Rescue of measles viruses from cloned DNA. *The EMBO journal,* 14(23), pp. 5773-84. Available at:

The claimed invention is:

1. A recombinant virus of the family Paramyxoviridae comprising at least one expressible polynucleotide encoding an interleukin 12 (IL-12) polypeptide wherein said IL-12 polypeptide is a fusion protein comprising a p35 subunit of an IL-12 and a p40 subunit of an IL-12, wherein said polynucleotide optionally encodes a ligand for an immune checkpoint blockade protein or a binding domain to a tumor associated antigen, and wherein said recombinant virus is encoded by a polynucleotide comprising the nucleic acid sequence selected from the group consisting of SEQ ID NOS 4 to 7, 14 and 15.

2. A host cell comprising the recombinant virus of the family Paramyxoviridae according to claim 1.

3. A medicament comprising (a) (i) the recombinant virus of the family Paramyxoviridae according to claim 1; and/or (a)(ii) a host cell comprising the recombinant virus of the family Paramyxoviridae according to claim 1; and (b) at least one pharmacological acceptable excipient.

4. A method for treating cancer in a subject afflicted with cancer, comprising administering to said subject a therapeutically effective amount of the medicament according to claim 3, thereby treating cancer in a subject afflicted with cancer.

5. The method of claim 4, wherein said cancer is a solid cancer, a metastasis, or a relapse thereof.

6. The method of claim 4, wherein treating cancer is reducing tumor burden.

7. The method of claim 4, wherein said cancer is malignant melanoma, head and neck cancer, hepatocellular carcinoma, pancreatic carcinoma, prostate cancer, renal cell carcinoma, gastric carcinoma, colorectal carcinoma, lymphomas or leukemias.

* * * * *

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial
<220> FEATURE:
<223> OTHER INFORMATION: artificial linker sequence

<400> SEQUENCE: 1

Gly Gly Gly Gly Ser
1               5
```

<210> SEQ ID NO 2
<211> LENGTH: 502
<212> TYPE: PRT
<213> ORGANISM: Artificial
<220> FEATURE:
<223> OTHER INFORMATION: anti-human PD-L1 single-chain antibody

<400> SEQUENCE: 2

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Thr Phe Gly Gln Gly Thr Lys Val Glu Ile Lys Arg Gly
        115                 120                 125

Gly Gly Gly Ser Gly Gly Gly Gly Ser Gly Gly Gly Gly Ser Gln Val
    130                 135                 140

Gln Leu Val Gln Ser Gly Ala Glu Val Lys Lys Pro Gly Ser Ser Val
145                 150                 155                 160

Lys Val Ser Cys Lys Thr Ser Gly Asp Thr Phe Ser Thr Tyr Ala Ile
                165                 170                 175

Ser Trp Val Arg Gln Ala Pro Gly Gln Gly Leu Glu Trp Met Gly Gly
            180                 185                 190

Ile Ile Pro Ile Phe Gly Lys Ala His Tyr Ala Gln Lys Phe Gln Gly
        195                 200                 205

Arg Val Thr Ile Thr Ala Asp Glu Ser Thr Ser Thr Ala Tyr Met Glu
    210                 215                 220

Leu Ser Ser Leu Arg Ser Glu Asp Thr Ala Val Tyr Phe Cys Ala Arg
225                 230                 235                 240

Lys Phe His Phe Val Ser Gly Ser Pro Phe Gly Met Asp Val Trp Gly
                245                 250                 255

Gln Gly Thr Thr Val Thr Val Ser Ser Val Asp Glu Ala Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365
```

-continued

```
Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Val Asp Asn
            500


<210> SEQ ID NO 3
<211> LENGTH: 1509
<212> TYPE: DNA
<213> ORGANISM: Artificial
<220> FEATURE:
<223> OTHER INFORMATION: anti-human PD-L1 single-chain antibody encoding
      sequence

<400> SEQUENCE: 3

atggaaaccc cagcacagct tctcttcctc ctgctgctct ggctcccaga taccactgga      60

gagattgtcc tgacacagag cccagctaca ctttccctgt ctccgggcga aagagcaacc     120

ctctcttgca gggctagcca gtctgtcagc tcttatctcg cctggtatca gcagaaacca     180

ggccaggctc ccagactgct gatctacgac gctagcaatc gcgccactgg cataccagca     240

cgcttttcag ggtccggcag tggtaccgac ttcaccctga ccatctcctc actggaacct     300

gaggactttg ccgtgtatta ctgtcaacag cggagtaact ggcccacctt tgggcagggc     360

actaaggtgg agatcaaacg cggtggtggt ggatcaggtg gaggcggaag tggaggtggc     420

ggatcccagg tgcaactggt acagagcggc gcagaagtga agaaacccgg gtcctcagtg     480

aaggtcagtt gcaagacatc cggggacacc ttctcaacgt atgccattag ctgggttaga     540

caggctcctg gtcaagggct tgagtggatg ggaggtatca ttcccatatt cgggaaagcg     600

cattatgccc agaagttcca aggcagggtc accatcactg ccgatgaatc cacaagtact     660

gcctacatgg agttgagctc cttgcgtagc gaggatactg cggtgtactt ttgtgcacgg     720

aagtttcact tcgtttcagg gagccctttc gggatggatg tttggggaca gggtacaacg     780

gtgacagtat ccagcgtcga cgaggccaaa tcttgtgaca aaactcacac atgcccaccg     840

tgcccagcac ccgaactcct ggggggaccg tcagtcttcc tcttcccccc aaaacccaag     900

gacaccctca tgatctcccg gacccctgag gtcacatgcg tggtggtgga cgtgagccac     960

gaagaccctg aggtcaagtt caactggtac gtggacggcg tggaggtgca taatgccaag    1020

acaaagccgc gggaggagca gtacaacagc acgtaccgtg tggtcagcgt cctcaccgtc    1080

ctgcaccagg actggctgaa tggcaaggag tacaagtgca aggtctccaa caaagccctc    1140

ccagccccca tcgagaaaac catctccaaa gccaaggggc agccccgaga accacaggtg    1200

tacaccctgc ccccatcccg ggatgagctg accaagaacc aggtcagcct gacctgcctg    1260
```

-continued gtcaaaggct tctatcccag cgacatcgcc gtggagtggg agagcaatgg gcagccggag 1320
aacaactaca agaccacgcc tcccgtgctg gactccgacg gctccttctt cctctacagc 1380
aagctcaccg tggacaagag caggtggcag caggggaacg tcttctcatg ctccgtgatg 1440
catgaggctc tgcacaacca ctacacgcag aagagcctct ccctgtctcc gggtaaagtc 1500
gacaattaa 1509

<210> SEQ ID NO 4
<211> LENGTH: 17610
<212> TYPE: DNA
<213> ORGANISM: Artificial
<220> FEATURE:
<223> OTHER INFORMATION: recombinant MV genome MeVac_P-FmIL-12

<400> SEQUENCE: 4
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtgaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcgg gaacaaggaa atctcagata ttgaagtgca agaccctgag ggattcaaca 600
tgattctggg taccatccta gcccaaattt gggtcttgct cgcaaaggcg gttacggccc 660
cagacacggc agctgattcg gagctaagaa ggtggataaa gtacacccaa caaagaaggg 720
tagttggtga atttagattg gagagaaaat ggttggatgt ggtgaggaac aggattgccg 780
aggacctctc cttacgccga ttcatggtcg ctctaatcct ggatatcaag agaacacccg 840
gaaacaaacc caggattgct gaaatgatat gtgacattga tacatatatc gtagaggcag 900
gattagccag ttttatcctg actattaagt ttgggataga aactatgtat cctgctcttg 960
gactgcatga atttgctggt gagttatcca cacttgagtc cttgatgaac ctttaccagc 1020
aaatggggga aactgcaccc tacatggtaa tcctggagaa ctcaattcag aacaagttca 1080
gtgcaggatc ataccctctg ctctggagct atgccatggg agtaggagtg gaacttgaaa 1140
actccatggg aggtttgaac tttggccgat cttactttga tccagcatat tttagattag 1200
ggcaagagat ggtaaggagg tcagctggaa aggtcagttc cacattggca tctgaactcg 1260
gtatcactgc cgaggatgca aggcttgttt cagagattgc aatgcatact actgaggaca 1320
agatcagtag agcggttgga cccagacaag cccaagtatc atttctacac ggtgatcaaa 1380
gtgagaatga gctaccgaga ttgggggggca aggaagatag gagggtcaaa cagagtcgag 1440
gagaagccag ggagagctac agagaaaccg ggcccagcag agcaagtgat gcgagagctg 1500
cccatcttcc aaccggcaca cccctagaca ttgacactgc aacggagtcc agccaagatc 1560
cgcaggacag tcgaaggtca gctgacgccc tgcttaggct gcaagccatg gcaggaatct 1620
cggaagaaca aggctcagac acggacaccc ctatagtgta caatgacaga aatcttctag 1680
actaggtgcg agaggccgag ggccagaaca acatccgcct accatccatc attgttataa 1740

-continued

```
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagcaa cctaaatcca ttataaaaaa cttaggaacc aggtccacac   3420
agctcgagtc gcgcgtggcc accatgtgtc ctcagaagct aaccatctcc tggtttgcca   3480
tcgttttgct ggtgtcccca ctcatggcca tgtgggagct ggagaaagac gtttatgttg   3540
tagaggtgga ctggactccc gatgcccctg gagaaacagt gaacctcacc tgtgacacgc   3600
ctgaagaaga tgacatcacc tggacctcag accagagaca tggagtcata ggctctggaa   3660
agaccctgac catcactgtc aaagagtttc tagatgctgg ccagtacacc tgccacaaag   3720
gaggcgagac tctgagccac tcacatctgc tgctccacaa gaaggaaaat ggaatttggt   3780
ccactgaaat tttaaaaaat ttcaaaaaca agactttcct gaagtgtgaa gcaccaaatt   3840
actccggacg gttcacgtgc tcatggctgg tgcaaagaaa catggacttg aagttcaaca   3900
tcaagagcag tagcagttcc cctgactctc gggcagtgac atgtggaatg gcgtctctgt   3960
ctgcagagaa ggtcacactg gaccaaaggg actatgagaa gtattcagtg tcctgccagg   4020
aggatgtcac ctgcccaact gccgaggaga ccctgcccat tgaactggcg ttggaagcac   4080
ggcagcagaa taaatatgag aactacagca ccagcttctt catcagggac atcatcaaac   4140
```

-continued

```
cagacccgcc caagaacttg cagatgaagc ctttgaagaa ctcacaggtg gaggtcagct   4200
gggagtaccc tgactcctgg agcactcccc attcctactt ctccctcaag ttctttgttc   4260
gaatccagcg caagaaagaa aagatgaagg agacagagga ggggtgtaac cagaaaggtg   4320
cgttcctcgt agagaagaca tctaccgaag tccaatgcaa aggcgggaat gtctgcgtgc   4380
aagctcagga tcgctattac aattcctcgt gcagcaagtg ggcatgtgtt ccctgcaggg   4440
tccgatccgg tggcggtggc tcgggcggtg gtgggtcggg tggcggcgga tctagggtca   4500
ttccagtctc tggacctgcc aggtgtctta gccagtcccg aaacctgctg aagaccacag   4560
atgacatggt gaagacggcc agagaaaaac tgaaacatta ttcctgcact gctgaagaca   4620
tcgatcatga agacatcaca cgggaccaaa ccagcacatt gaagacctgt ttaccactgg   4680
aactacacaa gaacgagagt tgcctggcta ctagagagac ttcttccaca acaagaggga   4740
gctgcctgcc cccacagaag acgtctttga tgatgaccct gtgccttggt agcatctatg   4800
aggacttgaa gatgtaccag acagagttcc aggccatcaa cgcagcactt cagaatcaca   4860
accatcagca gatcattcta gacaagggca tgctggtggc catcgatgag ctgatgcagt   4920
ctctgaatca taatggcgag actctgcgcc agaaacctcc tgtgggagaa gcagaccctt   4980
acagagtgaa aatgaagctc tgcatcctgc ttcacgcctt cagcacccgc gtcgtgacca   5040
tcaacagggt gatgggctat ctgagctccg cctgataatc gcgcgcgtgc tagtacaacc   5100
taaatccatt ataaaaaact taggagcaaa gtgattgcct cccaaggtcc acaatgacag   5160
agacctacga cttcgacaag tcggcatggg acatcaaagg gtcgatcgct ccgatacaac   5220
ccaccaccta cagtgatggc aggctggtgc cccaggtcag agtcatagat cctggtctag   5280
gcgacaggaa ggatgaatgc tttatgtaca tgtttctgct gggggttgtt gaggacagcg   5340
attccctagg gcctccaatc gggcgagcat ttgggttcct gcccttaggt gttggcagat   5400
ccacagcaaa gcccgaaaaa ctcctcaaag aggccactga gcttgacata gttgttagac   5460
gtacagcagg gctcaatgaa aaactggtgt tctacaacaa caccccacta actctcctca   5520
caccttggag aaaggtccta acaacaggga gtgtcttcaa cgcaaaccaa gtgtgcaatg   5580
cggttaatct gataccgctc gataccccgc agaggttccg tgttgtttat atgagcatca   5640
cccgtctttc ggataacggg tattacaccg ttcctagaag aatgctggaa ttcagatcgg   5700
tcaatgcagt ggccttcaac ctgctggtga cccttaggat tgacaaggcg ataggccctg   5760
ggaagatcat cgacaataca gagcaacttc ctgaggcaac atttatggtc cacatcggga   5820
acttcaggag aaagaagagt gaagtctact ctgccgatta ttgcaaaatg aaaatcgaaa   5880
agatgggcct ggtttttgca cttggtggga tagggggcac cagtcttcac attagaagca   5940
caggcaaaat gagcaagact ctccatgcac aactcgggtt caagaagacc ttatgttacc   6000
cgctgatgga tatcaatgaa gaccttaatc gattactctg gaggagcaga tgcaagatag   6060
taagaatcca ggcagttttg cagccatcag ttcctcaaga attccgcatt tacgacgacg   6120
tgatcataaa tgatgaccaa ggactattca aagttctgta gaccgtagtg cccagcaatg   6180
cccgaaaacg acccccctca caatgacagc cagaaggccc ggacaaaaaa gccccctccg   6240
aaagactcca cggaccaagc gagaggccag ccagcagccg acggcaagcg cgaacaccag   6300
gcggccccag cacagaacag ccctgacaca aggccaccac cagccacccc aatctgcatc   6360
ctcctcgtgg gacccccgag gaccaacccc caaggctgcc cccgatccaa accaccaacc   6420
gcatccccac cacccccggg aaagaaaccc ccagcaattg gaaggcccct ccccctcttc   6480
```

-continued

```
ctcaacacaa gaactccaca accgaaccgc acaagcgacc gaggtgaccc aaccgcaggc   6540
atccgactcc ctagacagat cctctctccc cggcaaacta aacaaaactt agggccaagg   6600
aacatacaca cccaacagaa cccagacccc ggcccacggc gccgcgcccc caaccccga    6660
caaccagagg gagcccccaa ccaatcccgc cggctccccc ggtgcccaca ggcagggaca   6720
ccaaccccg aacagaccca gcacccaacc atcgacaatc caagacgggg gggcccccc     6780
aaaaaaaggc ccccaggggc cgacagccag caccgcgagg aagcccaccc accccacaca   6840
cgaccacggc aaccaaacca gaacccagac caccctgggc caccagctcc cagactcggc   6900
catcaccccg cagaaaggaa aggccacaac ccgcgcaccc cagccccgat ccggcgggga   6960
gccacccaac ccgaaccagc acccaagagc gatccccgaa ggacccccga accgcaaagg   7020
acatcagtat cccacagcct ctccaagtcc cccggtctcc tcctcttctc gaagggacca   7080
aaagatcaat ccaccacacc cgacgacact caactcccca cccctaaagg agacaccggg   7140
aatcccagaa tcaagactca tccaatgtcc atcatgggtc tcaaggtgaa cgtctctgcc   7200
atattcatgg cagtactgtt aactctccaa acacccaccg gtcaaatcca ttggggcaat   7260
ctctctaaga taggggtggt aggaatagga agtgcaagct acaaagttat gactcgttcc   7320
agccatcaat cattagtcat aaaattaatg cccaatataa ctctcctcaa taactgcacg   7380
agggtagaga ttgcagaata caggagacta ctgagaacag ttttggaacc aattagagat   7440
gcacttaatg caatgaccca gaatataaga ccggttcaga gtgtagcttc aagtaggaga   7500
cacaagagat ttgcgggagt agtcctggca ggtgcggccc taggcgttgc cacagctgct   7560
cagataacag ccggcattgc acttcaccag tccatgctga actctcaagc catcgacaat   7620
ctgagagcga gcctggaaac tactaatcag gcaattgaga caatcagaca agcagggcag   7680
gagatgatat tggctgttca gggtgtccaa gactacatca ataatgagct gataccgtct   7740
atgaaccaac tatcttgtga tttaatcggc cagaagctcg ggctcaaatt gctcagatac   7800
tatacagaaa tcctgtcatt atttggcccc agtttacggg accccatatc tgcggagata   7860
tctatccagg ctttgagcta tgcgcttgga ggagacatca ataaggtgtt agaaaagctc   7920
ggatacagtg gaggtgattt actgggcatc ttagagagcg gaggaataaa ggcccggata   7980
actcacgtcg acacagagtc ctacttcatt gtcctcagta tagcctatcc gacgctgtcc   8040
gagattaagg gggtgattgt ccaccggcta gagggggtct cgtacaacat aggctctcaa   8100
gagtggtata ccactgtgcc caagtatgtt gcaacccaag ggtaccttat ctcgaatttt   8160
gatgagtcat cgtgtacttt catgccagag ggggactgtgt gcagccaaaa tgccttgtac  8220
ccgatgagtc ctctgctcca agaatgcctc cgggggtaca ccaagtcctg tgctcgtaca   8280
ctcgtatccg ggtcttttgg gaaccggttc attttatcac aagggaacct aatagccaat   8340
tgtgcatcaa tcctttgcaa gtgttacaca acaggaacga tcattaatca agaccctgac   8400
aagatcctaa catacattgc tgccgatcac tgcccggtag tcgaggtgaa cggcgtgacc   8460
atccaagtcg ggagcaggag gtatccagac gctgtgtact tgcacagaat tgacctcggt   8520
cctcccatat cattggagag gttggacgta gggacaaatc tggggaatgc aattgctaag   8580
ttggaggatg ccaaggaatt gttggagtca tcggaccaga tattgaggag tatgaaaggt   8640
ttatcgagca ctagcatagt ctacatcctg attgcagtgt gtcttggagg gttgataggg   8700
atccccgctt taatatgttg ctgcaggggg cgttgtaaca aaaagggaga acaagttggt   8760
atgtcaagac caggcctaaa gcctgatctt acgggaacat caaaatccta tgtaaggtcg   8820
ctctgatcct ctacaactct tgaaacacaa atgtcccaca agtctcctct tcgtcatcaa   8880
```

-continued

```
gcaaccaccg cacccagcat caagcccacc tgaaattatc tccggcttcc ctctggccga   8940
acaatatcgg tagttaatca aaacttaggg tgcaagatca tccacaatgt caccacaacg   9000
agaccggata aatgccttct acaaagataa cccccatccc aagggaagta ggatagtcat   9060
taacagagaa catcttatga ttgatagacc ttatgttttg ctggctgttc tgtttgtcat   9120
gtttctgagc ttgatcgggt tgctagccat tgcaggcatt agacttcatc gggcagccat   9180
ctacaccgca gagatccata aaagcctcag caccaatcta gatgtaacta actcaatcga   9240
gcatcaggtc aaggacgtgc tgacaccact cttcaaaatc atcggtgatg aagtgggcct   9300
gaggacacct cagagattca ctgacctagt gaaattaatc tctgacaaga ttaaattcct   9360
taatccggat agggagtacg acttcagaga tctcacttgg tgtatcaacc cgccagagag   9420
aatcaaattg gattatgatc aatactgtgc agatgtggct gctgaagagc tcatgaatgc   9480
attggtgaac tcaactctac tggagaccag aacaaccaat cagttcctag ctgtctcaaa   9540
gggaaactgc tcagggccca ctacaatcag aggtcaattc tcaaacatgt cgctgtccct   9600
gttagacttg tatttaggtc gaggttacaa tgtgtcatct atagtcacta tgacatccca   9660
gggaatgtat gggggaactt acctagtgga aaagcctaat ctgagcagca aaaggtcaga   9720
gttgtcacaa ctgagcatgt accgagtgtt tgaagtaggt gttatcagaa atccgggttt   9780
gggggctccg gtgttccata tgacaaacta tcttgagcaa ccagtcagta atgatctcag   9840
caactgtatg gtggctttgg gggagctcaa actcgcagcc ctttgtcacg gggaagattc   9900
tatcacaatt ccctatcagg gatcagggaa aggtgtcagc ttccagctcg tcaagctagg   9960
tgtctggaaa tccccaaccg acatgcaatc ctgggtcccc ttatcaacgg atgatccagt  10020
gatagacagg ctttacctct catctcacag aggtgttatc gctgacaatc aagcaaaatg  10080
ggctgtcccg acaacacgaa cagatgacaa gttgcgaatg gagacatgct tccaacaggc  10140
gtgtaagggt aaaatccaag cactctgcga gaatcccgag tgggcaccat tgaaggataa  10200
caggattcct tcatacgggg tcttgtctgt tgatctgagt ctgacagttg agcttaaaat  10260
caaaattgct tcgggattcg ggccattgat cacacacggt tcagggatgg acctatacaa  10320
atccaaccac aacaatgtgt attggctgac tatcccgcca atgaagaacc tagccttagg  10380
tgtaatcaac acattggagt ggataccgag attcaaggtt agtccctacc tcttcactgt  10440
cccaattaag gaagcaggcg aagactgcca tgccccaaca tacctacctg cggaggtgga  10500
tggtgatgtc aaactcagtt ccaatctggt gattctacct ggtcaagatc tccaatatgt  10560
tttggcaacc tacgatactt ccagggttga acatgctgtg gtttattacg tttacagccc  10620
aagccgctca ttttcttact tttatccttt taggttgcct ataaaggggg tccccatcga  10680
attacaagtg gaatgcttca catgggacca aaaactctgg tgccgtcact tctgtgtgct  10740
tgcggactca gaatctggtg gacatatcac tcactctggg atggtgggca tgggagtcag  10800
ctgcacagtc acccgggaag atggaaccaa tcgcagatag ggctgctagt gaaccaatca  10860
catgatgtca cccagacatc aggcataccc actagtgtga aatagacatc agaattaaga  10920
aaaacgtagg gtccaagtgg ttccccgtta tggactcgct atctgtcaac cagatcttat  10980
accctgaagt tcacctagat agcccgatag ttaccaataa gatagtagcc atcctggagt  11040
atgctcgagt ccctcacgct tacagcctgg aggaccctac actgtgtcag aacatcaagc  11100
accgcctaaa aaacggattt tccaaccaaa tgattataaa caatgtggaa gttgggaatg  11160
tcatcaagtc caagcttagg agttatccgg cccactctca tattccatat ccaaattgta  11220
```

-continued atcaggattt atttaacata gaagacaaag agtcaacgag gaagatccgt gaactcctca 11280
aaaaggggaa ttcgctgtac tccaaagtca gtgataaggt tttccaatgc ttaagggaca 11340
ctaactcacg gcttggccta ggctccgaat tgagggagga catcaaggag aaagttatta 11400
acttgggagt ttacatgcac agctcccagt ggtttgagcc ctttctgttt tggtttacag 11460
tcaagactga gatgaggtca gtgattaaat cacaaaccca tacttgccat aggaggagac 11520
acacacctgt attcttcact ggtagttcag ttgagttgct aatctctcgt gaccttgttg 11580
ctataatcag taaagagtct caacatgtat attacctgac atttgaactg gttttgatgt 11640
attgtgatgt catagagggg aggttaatga cagagaccgc tatgactatt gatgctaggt 11700
atacagagct tctaggaaga gtcagataca tgtggaaact gatagatggt ttcttccctg 11760
cactcgggaa tccaacttat caaattgtag ccatgctgga gcctctttca cttgcttacc 11820
tgcagctgag ggatataaca gtagaactca gaggtgcttt ccttaaccac tgctttactg 11880
aaatacatga tgttcttgac caaaacgggt tttctgatga aggtacttat catgagttaa 11940
ctgaagctct agattacatt ttcataactg atgacataca tctgacaggg gagattttct 12000
catttttcag aagtttcggc caccccagac ttgaagcagt aacggctgct gaaaatgtta 12060
ggaaatacat gaatcagcct aaagtcattg tgtatgagac tctgatgaaa ggtcatgcca 12120
tattttgtgg aatcataatc aacggctatc gtgacaggca cggaggcagt tggccaccgc 12180
tgaccctccc cctgcatgct gcagacacaa tccggaatgc tcaagcttca ggtgaagggt 12240
taacacatga gcagtgcgtt gataactgga aatcttttgc tggagtgaaa tttggctgct 12300
ttatgcctct tagcctggat agtgatctga caatgtacct aaaggacaag gcacttgctg 12360
ctctccaaag ggaatgggat tcagtttacc cgaaagagtt cctgcgttac gaccctccca 12420
agggaaccgg gtcacggagg cttgtagatg ttttccttaa tgattcgagc tttgacccat 12480
atgatgtgat aatgtatgtt gtaagtggag cttacctcca tgaccctgag ttcaacctgt 12540
cttacagcct gaaagaaaag gagatcaagg aaacaggtag actttttgct aaaatgactt 12600
acaaaatgag ggcatgccaa gtgattgctg aaaatctaat ctcaaacggg attggcaaat 12660
attttaagga caatgggatg gccaaggatg agcacgattt gactaaggca ctccacactc 12720
tagctgtctc aggagtcccc aaagatctca aagaaagtca caggggggg ccagtcttaa 12780 aaacctactc ccgaagccca gtccacacaa gtaccaggaa cgtgagagca gcaaaagggt 12840
ttatagggtt ccctcaagta attcggcagg accaagacac tgatcatccg gagaatatgg 12900
aagcttacga gacagtcagt gcatttatca cgactgatct caagaagtac tgccttaatt 12960
ggagatatga gaccatcagc ttgtttgcac agaggctaaa tgagatttac ggattgccct 13020
catttttcca gtggctgcat aagaggcttg agacctctgt cctgtatgta agtgaccctc 13080
attgcccccc cgaccttgac gcccatatcc cgttatataa agtccccaat gatcaaatct 13140
tcattaagta ccctatggga ggtatagaag ggtattgtca gaagctgtgg accatcagca 13200
ccattcccta tctatacctg gctgcttatg agagcggagt aaggattgct tcgttagtgc 13260
aaggggacaa tcagaccata gccgtaacaa aaagggtacc cagcacatgg ccctacaacc 13320
ttaagaaacg ggaagctgct agagtaacta gagattactt tgtaattctt aggcaaaggc 13380
tacatgatat tggccatcac ctcaaggcaa atgagacaat tgtttcatca catttttttg 13440
tctattcaaa aggaatatat tatgatgggc tacttgtgtc ccaatcactc aagagcatcg 13500
caagatgtgt attctggtca gagactatag ttgatgaaac aagggcagca tgcagtaata 13560
ttgctacaac aatggctaaa agcatcgaga gaggttatga ccgttacctt gcatattccc 13620

```
tgaacgtcct aaaagtgata cagcaaattc tgatctctct tggcttcaca atcaattcaa  13680
ccatgacccg ggatgtagtc atacccctcc tcacaaacaa cgacctctta ataaggatgg  13740
cactgttgcc cgctcctatt ggggggatga attatctgaa tatgagcagg ctgtttgtca  13800
gaaacatcgg tgatccagta acatcatcaa ttgctgatct caagagaatg attctcgcct  13860
cactaatgcc tgaagagacc ctccatcaag taatgacaca acaaccgggg gactcttcat  13920
tcctagactg ggctagcgac ccttactcag caaatcttgt atgtgtccag agcatcacta  13980
gactcctcaa gaacataact gcaaggtttg tcctgatcca tagtccaaac ccaatgttaa  14040
aaggattatt ccatgatgac agtaaagaag aggacgaggg actggcggca ttcctcatgg  14100
acaggcatat tatagtacct agggcagctc atgaaatcct ggatcatagt gtcacagggg  14160
caagagagtc tattgcaggc atgctggata ccacaaaagg cttgattcga gccagcatga  14220
ggaagggggg gttaacctct cgagtgataa ccagattgtc caattatgac tatgaacaat  14280
tcagagcagg gatggtgcta ttgacaggaa gaaagagaaa tgtcctcatt gacaaagagt  14340
catgttcagt gcagctggcg agagctctaa gaagccatat gtgggcgagg ctagctcgag  14400
gacggcctat ttacggcctt gaggtccctg atgtactaga atctatgcga ggccacctta  14460
ttcggcgtca tgagacatgt gtcatctgcg agtgtggatc agtcaactac ggatggtttt  14520
ttgtcccctc gggttgccaa ctggatgata ttgacaagga aacatcatcc ttgagagtcc  14580
catatattgg ttctaccact gatgagagaa cagacatgaa gcttgccttc gtaagagccc  14640
caagtcgatc cttgcgatct gctgttagaa tagcaacagt gtactcatgg gcttacggtg  14700
atgatgatag ctcttggaac gaagcctggt tgttggctag gcaaagggcc aatgtgagcc  14760
tggaggagct aagggtgatc actcccatct caacttcgac taatttagcg cataggttga  14820
gggatcgtag cactcaagtg aaatactcag gtacatccct tgtccgagtg gcgaggtata  14880
ccacaatctc caacgacaat ctctcatttg tcatatcaga taagaaggtt gatactaact  14940
ttatatacca acaaggaatg cttctagggt tgggtgtttt agaaacattg tttcgactcg  15000
agaaagatac cggatcatct aacacggtat tacatcttca cgtcgaaaca gattgttgcg  15060
tgatcccgat gatagatcat cccaggatac ccagctcccg caagctagag ctgagggcag  15120
agctatgtac caacccattg atatatgata atgcaccttt aattgacaga gatgcaacaa  15180
ggctatacac ccagagccat aggaggcacc ttgtggaatt tgttacatgg tccacacccc  15240
aactatatca cattttagct aagtccacag cactatctat gattgacctg gtaacaaaat  15300
ttgagaagga ccatatgaat gaaatttcag ctctcatagg ggatgacgat atcaatagtt  15360
tcataactga gtttctgctc atagagccaa gattattcac tatctacttg ggccagtgtg  15420
cggccatcaa ttgggcattt gatgtacatt atcatagacc atcagggaaa tatcagatgg  15480
gtgagctgtt gtcatcgttc ctttctagaa tgagcaaagg agtgtttaag gtgcttgtca  15540
atgctctaag ccacccaaag atctacaaga aattctggca ttgtggtatt atagagccta  15600
tccatggtcc ttcacttgat gctcaaaact tgcacacaac tgtgtgcaac atggtttaca  15660
catgctatat gacctacctc gacctgttgt tgaatgaaga gttagaagag ttcacatttc  15720
tcttgtgtga aagcgacgag gatgtagtac cggacagatt cgacaacatc caggcaaaac  15780
acttatgtgt tctggcagat ttgtactgtc aaccagggac ctgcccacca attcgaggtc  15840
taagaccggt agagaaatgt gcagttctaa ccgaccatat caaggcagag gctatgttat  15900
ctccagcagg atcttcgtgg aacataaatc caattattgt agaccattac tcatgctctc  15960
```

```
tgacttatct ccggcgagga tcgatcaaac agataagatt gagagttgat ccaggattca  16020

ttttcgacgc cctcgctgag gtaaatgtca gtcagccaaa gatcggcagc aacaacatct  16080

caaatatgag catcaaggct ttcagacccc cacacgatga tgttgcaaaa ttgctcaaag  16140

atatcaacac aagcaagcac aatcttccca tttcaggggg caatctcgcc aattatgaaa  16200

tccatgcttt ccgcagaatc gggttgaact catctgcttg ctacaaagct gttgagatat  16260

caacattaat taggagatgc cttgagccag gggaggacgg cttgttcttg ggtgagggat  16320

cgggttctat gttgatcact tataaagaga tacttaaact aaacaagtgc ttctataata  16380

gtggggtttc cgccaattct agatctggtc aaagggaatt agcaccctat ccctccgaag  16440

ttggccttgt cgaacacaga atgggagtag gtaatattgt caaagtgctc tttaacggga  16500

ggcccgaagt cacgtgggta ggcagtgtag attgcttcaa tttcatagtt agtaatatcc  16560

ctacctctag tgtggggttt atccattcag atatagagac cttgcctgac aaagatacta  16620

tagagaagct agaggaattg gcagccatct tatcgatggc tctgctcctg ggcaaaatag  16680

gatcaatact ggtgattaag cttatgcctt tcagcgggga ttttgttcag ggatttataa  16740

gttatgtagg gtctcattat agagaagtga accttgtata ccctagatac agcaacttca  16800

tctctactga atcttatttg gttatgacag atctcaaggc taaccggcta atgaatcctg  16860

aaaagattaa gcagcagata attgaatcat ctgtgaggac ttcacctgga cttataggtc  16920

acatcctatc cattaagcaa ctaagctgca tacaagcaat tgtgggagac gcagttagta  16980

gaggtgatat caatcctact ctgaaaaaac ttacacctat agagcaggtg ctgatcaatt  17040

gcgggttggc aattaacgga cctaagctgt gcaaagaatt gatccaccat gatgttgcct  17100

cagggcaaga tggattgctt aattctatac tcatcctcta cagggagttg gcaagattca  17160

aagacaacca aagaagtcaa caagggatgt tccacgctta ccccgtattg gtaagtagca  17220

ggcaacgaga acttatatct aggatcaccc gcaaattctg gggcacatt cttctttact  17280

ccgggaacaa aaagttgata aataagttta tccagaatct caagtccggc tatctgatac  17340

tagacttaca ccagaatatc ttcgttaaga atctatccaa gtcagagaaa cagattatta  17400

tgacgggggg tttgaaacgt gagtgggttt ttaaggtaac agtcaaggag accaaagaat  17460

ggtataagtt agtcggatac agtgccctga ttaaggacta attggttgaa ctccggaacc  17520

ctaatcctgc cctaggtggt taggcattat ttgcaatata ttaaagaaaa ctttgaaaat  17580

acgaagtttc tattcccagc tttgtctggt                                   17610
```

<210> SEQ ID NO 5
<211> LENGTH: 17570
<212> TYPE: DNA
<213> ORGANISM: Artificial
<220> FEATURE:
<223> OTHER INFORMATION: artificial MV genome MeVac_P-FhIL-12

<400> SEQUENCE: 5

```
accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtgaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420
```

-continued

```
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
gactgcatga atttgctggt gagttatcca cacttgagtc cttgatgaac ctttaccagc   1020
aaatggggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttgggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
```

-continued

```
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagcaa cctaaatcca ttataaaaaa cttaggaacc aggtccacac   3420
agctcgagtc gcgcgtgcca ccatgtgtca ccagcagttg gtcatctctt ggttttccct   3480
ggtttttctg gcatctcccc tcgtggccat atgggaactg aagaaagatg tttatgtcgt   3540
agaattggat tggtatccgg atgcccctgg agaaatggtg gtcctcacct gtgacacccc   3600
tgaagaagat ggtatcacct ggaccttgga ccagagcagt gaggtcttag gctctggcaa   3660
aaccctgacc atccaagtca aagagtttgg agatgctggc cagtacacct gtcacaaagg   3720
aggcgaggtt ctaagccatt cgctcctgct gcttcacaaa aaggaagatg gaatttggtc   3780
cactgatatt ttaaaggacc agaaagaacc caaaaataag acctttctaa gatgcgaggc   3840
caagaattat tctggacgtt tcacctgctg gtggctgacg acaatcagta ctgatttgac   3900
attcagtgtc aaaagcagca gaggctcttc tgacccccaa ggggtgacgt gcggagctgc   3960
tacactctct gcagagagag tcagagggga caacaaggag tatgagtact cagtggagtg   4020
ccaggaggac agtgcctgcc cagctgctga ggagagtctg cccattgagg tcatggtgga   4080
tgccgttcac aagctcaagt atgaaaacta caccagcagc ttcttcatca gggacatcat   4140
caaacctgac ccacccaaga acttgcagct gaagccatta aagaattctc ggcaggtgga   4200
ggtcagctgg gagtaccctg acacctggag tactccacat tcctacttct ccctgacatt   4260
ctgcgttcag gtccagggca agagcaagag agaaaagaaa gatagagtct tcaccgacaa   4320
gacctcagcc acggtcatct gccgcaaaaa tgccagcatt agcgtgcggg cccaggaccg   4380
ctactatagc tcatcttgga gcgaatgggc atctgtgccc tgcagtggtg gcggtggcgg   4440
cggatctaga aacctccccg tggccactcc agacccagga atgttcccat gccttcacca   4500
ctcccaaaac ctgctgaggg ccgtcagcaa catgctccag aaggccagac aaactctaga   4560
attttaccct tgcacttctg aagagattga tcatgaagat atcacaaaag ataaaaccag   4620
cacagtggag gcctgtttac cattggaatt aaccaagaat gagagttgcc taaattccag   4680
agagacctct ttcataacta atgggagttg cctggcctcc agaaagacct cttttatgat   4740
ggccctgtgc cttagtagta tttatgaaga cttgaagatg taccaggtgg agttcaagac   4800
catgaatgca aagcttctga tggatcctaa gaggcagatc tttctagatc aaaacatgct   4860
ggcagttatt gatgagctga tgcaggccct gaatttcaac agtgagactg tgccacaaaa   4920
atcctccctt gaagaaccgg atttttataa aactaaaatc aagctctgca tacttcttca   4980
tgctttcaga attcgggcag tgactattga tagagtgatg agctatctga atgcttccta   5040
ggcgcgcgtg ctagtacaac ctaaatccat tataaaaaac ttaggagcaa agtgattgcc   5100
tcccaaggtc cacaatgaca gagacctacg acttcgacaa gtcggcatgg gacatcaaag   5160
```

-continued

```
ggtcgatcgc tccgatacaa cccaccacct acagtgatgg caggctggtg ccccaggtca   5220

gagtcataga tcctggtcta ggcgacagga aggatgaatg ctttatgtac atgtttctgc   5280

tgggggttgt tgaggacagc gattccctag ggcctccaat cgggcgagca tttgggttcc   5340

tgcccttagg tgttggcaga tccacagcaa agcccgaaaa actcctcaaa gaggccactg   5400

agcttgacat agttgttaga cgtacagcag ggctcaatga aaaactggtg ttctacaaca   5460

acaccccact aactctcctc acaccttgga gaaaggtcct aacaacaggg agtgtcttca   5520

acgcaaacca agtgtgcaat gcggttaatc tgataccgct cgataccccg cagaggttcc   5580

gtgttgttta tatgagcatc acccgtcttt cggataacgg gtattacacc gttcctagaa   5640

gaatgctgga attcagatcg gtcaatgcag tggccttcaa cctgctggtg acccttagga   5700

ttgacaaggc gataggccct gggaagatca tcgacaatac agagcaactt cctgaggcaa   5760

catttatggt ccacatcggg aacttcagga gaaagaagag tgaagtctac tctgccgatt   5820

attgcaaaat gaaaatcgaa aagatgggcc tggtttttgc acttggtggg atagggggca   5880

ccagtcttca cattagaagc acaggcaaaa tgagcaagac tctccatgca caactcgggt   5940

tcaagaagac cttatgttac ccgctgatgg atatcaatga agaccttaat cgattactct   6000

ggaggagcag atgcaagata gtaagaatcc aggcagtttt gcagccatca gttcctcaag   6060

aattccgcat ttacgacgac gtgatcataa atgatgacca aggactattc aaagttctgt   6120

agaccgtagt gcccagcaat gcccgaaaac gacccccctc acaatgacag ccagaaggcc   6180

cggacaaaaa agcccccctcc gaaagactcc acggaccaag cgagaggcca gccagcagcc   6240

gacggcaagc gcgaacacca ggcggcccca gcacagaaca gccctgacac aaggccacca   6300

ccagccaccc caatctgcat cctcctcgtg ggacccccga ggaccaaccc ccaaggctgc   6360

ccccgatcca aaccaccaac cgcatcccca ccacccccgg gaaagaaacc cccagcaatt   6420

ggaaggcccc tccccctctt cctcaacaca agaactccac aaccgaaccg cacaagcgac   6480

cgaggtgacc caaccgcagg catccgactc cctagacaga tcctctctcc ccggcaaact   6540

aaacaaaact tagggccaag gaacatacac acccaacaga acccagaccc cggcccacgg   6600

cgccgcgccc ccaacccccg acaaccagag ggagccccca accaatcccg ccggctcccc   6660

cggtgcccac aggcagggac accaaccccc gaacagaccc agcacccaac catcgacaat   6720

ccaagacggg ggggcccccc caaaaaaagg cccccagggg ccgacagcca gcaccgcgag   6780

gaagcccacc cacccccacac acgaccacgg caaccaaacc agaacccaga ccaccctggg   6840

ccaccagctc ccagactcgg ccatcacccc gcagaaagga aaggccacaa cccgcgcacc   6900

ccagccccga tccggcgggg agccacccaa cccgaaccag cacccaagag cgatccccga   6960

aggacccccg aaccgcaaag gacatcagta tcccacagcc tctccaagtc ccccggtctc   7020

ctcctcttct cgaagggacc aaaagatcaa tccaccacac ccgacgacac tcaactcccc   7080

acccctaaag gagacaccgg gaatcccaga atcaagactc atccaatgtc catcatgggt   7140

ctcaaggtga acgtctctgc catattcatg gcagtactgt taactctcca aacacccacc   7200

ggtcaaatcc attggggcaa tctctctaag ataggggtgg taggaatagg aagtgcaagc   7260

tacaaagtta tgactcgttc cagccatcaa tcattagtca taaaattaat gcccaatata   7320

actctcctca ataactgcac gagggtagag attgcagaat acaggagact actgagaaca   7380

gttttggaac caattagaga tgcacttaat gcaatgaccc agaatataag accggttcag   7440

agtgtagctt caagtaggag acacaagaga tttgcgggag tagtcctggc aggtgcggcc   7500
```

-continued

```
ctaggcgttg ccacagctgc tcagataaca gccggcattg cacttcacca gtccatgctg   7560
aactctcaag ccatcgacaa tctgagagcg agcctggaaa ctactaatca ggcaattgag   7620
acaatcagac aagcagggca ggagatgata ttggctgttc agggtgtcca agactacatc   7680
aataatgagc tgataccgtc tatgaaccaa ctatcttgtg atttaatcgg ccagaagctc   7740
gggctcaaat tgctcagata ctatacagaa atcctgtcat tatttggccc cagtttacgg   7800
gaccccatat ctgcggagat atctatccag gctttgagct atgcgcttgg aggagacatc   7860
aataaggtgt tagaaaagct cggatacagt ggaggtgatt tactgggcat cttagagagc   7920
ggaggaataa aggcccggat aactcacgtc gacacagagt cctacttcat tgtcctcagt   7980
atagcctatc cgacgctgtc cgagattaag ggggtgattg tccaccggct agagggggtc   8040
tcgtacaaca taggctctca agagtggtat accactgtgc ccaagtatgt tgcaacccaa   8100
gggtacctta tctcgaattt tgatgagtca tcgtgtactt tcatgccaga ggggactgtg   8160
tgcagccaaa atgccttgta cccgatgagt cctctgctcc aagaatgcct ccgggggtac   8220
accaagtcct gtgctcgtac actcgtatcc gggtcttttg ggaaccggtt cattttatca   8280
caagggaacc taatagccaa ttgtgcatca atcctttgca agtgttacac aacaggaacg   8340
atcattaatc aagaccctga caagatccta acatacattg ctgccgatca ctgcccggta   8400
gtcgaggtga acggcgtgac catccaagtc gggagcagga ggtatccaga cgctgtgtac   8460
ttgcacagaa ttgacctcgg tcctcccata tcattggaga ggttggacgt agggacaaat   8520
ctggggaatg caattgctaa gttggaggat gccaaggaat tgttggagtc atcggaccag   8580
atattgagga gtatgaaagg tttatcgagc actagcatag tctacatcct gattgcagtg   8640
tgtcttggag ggttgatagg gatccccgct ttaatatgtt gctgcagggg gcgttgtaac   8700
aaaaagggag aacaagttgg tatgtcaaga ccaggcctaa agcctgatct tacgggaaca   8760
tcaaaatcct atgtaaggtc gctctgatcc tctacaactc ttgaaacaca aatgtcccac   8820
aagtctcctc ttcgtcatca agcaaccacc gcacccagca tcaagcccac ctgaaattat   8880
ctccggcttc cctctggccg aacaatatcg gtagttaatc aaaacttagg gtgcaagatc   8940
atccacaatg tcaccacaac gagaccggat aaatgccttc tacaaagata acccccatcc   9000
caagggaagt aggatagtca ttaacagaga acatcttatg attgatagac cttatgtttt   9060
gctggctgtt ctgtttgtca tgtttctgag cttgatcggg ttgctagcca ttgcaggcat   9120
tagacttcat cgggcagcca tctacaccgc agagatccat aaaagcctca gcaccaatct   9180
agatgtaact aactcaatcg agcatcaggt caaggacgtg ctgacaccac tcttcaaaat   9240
catcggtgat gaagtgggcc tgaggacacc tcagagattc actgacctag tgaaattaat   9300
ctctgacaag attaaattcc ttaatccgga tagggagtac gacttcagag atctcacttg   9360
gtgtatcaac ccgccagaga gaatcaaatt ggattatgat caatactgtg cagatgtggc   9420
tgctgaagag ctcatgaatg cattggtgaa ctcaactcta ctggagacca gaacaaccaa   9480
tcagttccta gctgtctcaa agggaaactg ctcagggccc actacaatca gaggtcaatt   9540
ctcaaacatg tcgctgtccc tgttagactt gtatttaggt cgaggttaca atgtgtcatc   9600
tatagtcact atgacatccc agggaatgta tgggggaact tacctagtgg aaaagcctaa   9660
tctgagcagc aaaaggtcag agttgtcaca actgagcatg taccgagtgt ttgaagtagg   9720
tgttatcaga aatccgggtt tgggggctcc ggtgttccat atgacaaact atcttgagca   9780
accagtcagt aatgatctca gcaactgtat ggtggctttg ggggagctca aactcgcagc   9840
cctttgtcac ggggaagatt ctatcacaat tccctatcag ggatcaggga aaggtgtcag   9900
```

```
cttccagctc gtcaagctag gtgtctggaa atccccaacc gacatgcaat cctgggtccc   9960
cttatcaacg gatgatccag tgatagacag gctttacctc tcatctcaca gaggtgttat  10020
cgctgacaat caagcaaaat gggctgtccc gacaacacga acagatgaca agttgcgaat  10080
ggagacatgc ttccaacagg cgtgtaaggg taaaatccaa gcactctgcg agaatcccga  10140
gtgggcacca ttgaaggata acaggattcc ttcatacggg gtcttgtctg ttgatctgag  10200
tctgacagtt gagcttaaaa tcaaaattgc ttcgggattc gggccattga tcacacacgg  10260
ttcagggatg gacctataca aatccaacca caacaatgtg tattggctga ctatcccgcc  10320
aatgaagaac ctagccttag gtgtaatcaa cacattggag tggataccga gattcaaggt  10380
tagtccctac ctcttcactg tcccaattaa ggaagcaggc gaagactgcc atgccccaac  10440
atacctacct gcggaggtgg atggtgatgt caaactcagt tccaatctgg tgattctacc  10500
tggtcaagat ctccaatatg ttttggcaac ctacgatact tccagggttg aacatgctgt  10560
ggtttattac gtttacagcc caagccgctc attttcttac ttttatcctt ttaggttgcc  10620
tataaagggg gtccccatcg aattacaagt ggaatgcttc acatgggacc aaaaactctg  10680
gtgccgtcac ttctgtgtgc ttgcggactc agaatctggt ggacatatca ctcactctgg  10740
gatggtgggc atgggagtca gctgcacagt cacccgggaa gatggaacca atcgcagata  10800
gggctgctag tgaaccaatc acatgatgtc acccagacat caggcatacc cactagtgtg  10860
aaatagacat cagaattaag aaaaacgtag ggtccaagtg gttccccgtt atggactcgc  10920
tatctgtcaa ccagatctta taccctgaag ttcacctaga tagcccgata gttaccaata  10980
agatagtagc catcctggag tatgctcgag tccctcacgc ttacagcctg gaggacccta  11040
cactgtgtca gaacatcaag caccgcctaa aaaacggatt ttccaaccaa atgattataa  11100
acaatgtgga agttgggaat gtcatcaagt ccaagcttag gagttatccg gcccactctc  11160
atattccata tccaaattgt aatcaggatt tatttaacat agaagacaaa gagtcaacga  11220
ggaagatccg tgaactcctc aaaaagggga attcgctgta ctccaaagtc agtgataagg  11280
ttttccaatg cttaagggac actaactcac ggcttggcct aggctccgaa ttgagggagg  11340
acatcaagga gaaagttatt aacttgggag tttacatgca cagctcccag tggtttgagc  11400
cctttctgtt ttggtttaca gtcaagactg agatgaggtc agtgattaaa tcacaaaccc  11460
atacttgcca taggaggaga cacacacctg tattcttcac tggtagttca gttgagttgc  11520
taatctctcg tgaccttgtt gctataatca gtaaagagtc tcaacatgta tattacctga  11580
catttgaact ggttttgatg tattgtgatg tcatagaggg gaggttaatg acagagaccg  11640
ctatgactat tgatgctagg tatacagagc ttctaggaag agtcagatac atgtggaaac  11700
tgatagatgg tttcttccct gcactcggga atccaactta tcaaattgta gccatgctgg  11760
agcctctttc acttgcttac ctgcagctga gggatataac agtagaactc agaggtgctt  11820
tccttaacca ctgctttact gaaatacatg atgttcttga ccaaaacggg ttttctgatg  11880
aaggtactta tcatgagtta actgaagctc tagattacat tttcataact gatgacatac  11940
atctgacagg ggagattttc tcatttttca gaagtttcgg ccaccccaga cttgaagcag  12000
taacggctgc tgaaaatgtt aggaaataca tgaatcagcc taaagtcatt gtgtatgaga  12060
ctctgatgaa aggtcatgcc atattttgtg gaatcataat caacggctat cgtgacaggc  12120
acggaggcag ttggccaccg ctgaccctcc ccctgcatgc tgcagacaca atccggaatg  12180
ctcaagcttc aggtgaaggg ttaacacatg agcagtgcgt tgataactgg aaatcttttg  12240
```

-continued

```
ctggagtgaa atttggctgc tttatgcctc ttagcctgga tagtgatctg acaatgtacc  12300
taaaggacaa ggcacttgct gctctccaaa gggaatggga ttcagtttac ccgaaagagt  12360
tcctgcgtta cgaccctccc aagggaaccg ggtcacggag gcttgtagat gttttcctta  12420
atgattcgag ctttgaccca tatgatgtga taatgtatgt tgtaagtgga gcttacctcc  12480
atgaccctga gttcaacctg tcttacagcc tgaaagaaaa ggagatcaag gaaacaggta  12540
gactttttgc taaaatgact tacaaaatga gggcatgcca agtgattgct gaaaatctaa  12600
tctcaaacgg gattggcaaa tattttaagg acaatgggat ggccaaggat gagcacgatt  12660
tgactaaggc actccacact ctagctgtct caggagtccc caaagatctc aaagaaagtc  12720
acaggggggg gccagtctta aaaacctact cccgaagccc agtccacaca agtaccagga  12780
acgtgagagc agcaaaaggg tttatagggt tccctcaagt aattcggcag gaccaagaca  12840
ctgatcatcc ggagaatatg gaagcttacg agacagtcag tgcatttatc acgactgatc  12900
tcaagaagta ctgccttaat tggagatatg agaccatcag cttgtttgca cagaggctaa  12960
atgagattta cggattgccc tcatttttcc agtggctgca taagaggctt gagacctctg  13020
tcctgtatgt aagtgaccct cattgccccc ccgaccttga cgcccatatc ccgttatata  13080
aagtccccaa tgatcaaatc ttcattaagt accctatggg aggtatagaa gggtattgtc  13140
agaagctgtg gaccatcagc accattccct atctatacct ggctgcttat gagagcggag  13200
taaggattgc ttcgttagtg caaggggaca atcagaccat agccgtaaca aaaagggtac  13260
ccagcacatg gccctacaac cttaagaaac gggaagctgc tagagtaact agagattact  13320
ttgtaattct taggcaaagg ctacatgata ttggccatca cctcaaggca aatgagacaa  13380
ttgtttcatc acattttttt gtctattcaa aaggaatata ttatgatggg ctacttgtgt  13440
cccaatcact caagagcatc gcaagatgtg tattctggtc agagactata gttgatgaaa  13500
caagggcagc atgcagtaat attgctacaa caatggctaa aagcatcgag agaggttatg  13560
accgttacct tgcatattcc ctgaacgtcc taaaagtgat acagcaaatt ctgatctctc  13620
ttggcttcac aatcaattca accatgaccc gggatgtagt catacccctc ctcacaaaca  13680
acgacctctt aataaggatg gcactgttgc ccgctcctat tggggggatg aattatctga  13740
atatgagcag gctgtttgtc agaaacatcg gtgatccagt aacatcatca attgctgatc  13800
tcaagagaat gattctcgcc tcactaatgc ctgaagagac cctccatcaa gtaatgacac  13860
aacaaccggg ggactcttca ttcctagact gggctagcga cccttactca gcaaatcttg  13920
tatgtgtcca gagcatcact agactcctca agaacataac tgcaaggttt gtcctgatcc  13980
atagtccaaa cccaatgtta aaaggattat tccatgatga cagtaaagaa gaggacgagg  14040
gactggcggc attcctcatg gacaggcata ttatagtacc tagggcagct catgaaatcc  14100
tggatcatag tgtcacaggg gcaagagagt ctattgcagg catgctggat accacaaaag  14160
gcttgattcg agccagcatg aggaaggggg ggttaacctc tcgagtgata accagattgt  14220
ccaattatga ctatgaacaa ttcagagcag ggatggtgct attgacagga agaaagagaa  14280
atgtcctcat tgacaaagag tcatgttcag tgcagctggc gagagctcta agaagccata  14340
tgtgggcgag gctagctcga ggacggccta tttacggcct tgaggtccct gatgtactag  14400
aatctatgcg aggccacctt attcggcgtc atgagacatg tgtcatctgc gagtgtggat  14460
cagtcaacta cggatggttt tttgtcccct cgggttgcca actggatgat attgacaagg  14520
aaacatcatc cttgagagtc ccatatattg gttctaccac tgatgagaga acagacatga  14580
agcttgcctt cgtaagagcc ccaagtcgat ccttgcgatc tgctgttaga atagcaacag  14640
```

-continued tgtactcatg ggcttacggt gatgatgata gctcttggaa cgaagcctgg ttgttggcta 14700
ggcaaagggc caatgtgagc ctggaggagc taagggtgat cactcccatc tcaacttcga 14760
ctaatttagc gcataggttg agggatcgta gcactcaagt gaaatactca ggtacatccc 14820
ttgtccgagt ggcgaggtat accacaatct ccaacgacaa tctctcattt gtcatatcag 14880
ataagaaggt tgatactaac tttatatacc aacaaggaat gcttctaggg ttgggtgttt 14940
tagaaacatt gtttcgactc gagaaagata ccggatcatc taacacggta ttacatcttc 15000
acgtcgaaac agattgttgc gtgatcccga tgatagatca tcccaggata cccagctccc 15060
gcaagctaga gctgagggca gagctatgta ccaacccatt gatatatgat aatgcacctt 15120
taattgacag agatgcaaca aggctataca cccagagcca taggaggcac cttgtggaat 15180
ttgttacatg gtccacaccc caactatatc acattttagc taagtccaca gcactatcta 15240
tgattgacct ggtaacaaaa tttgagaagg accatatgaa tgaaatttca gctctcatag 15300
gggatgacga tatcaatagt ttcataactg agtttctgct catagagcca agattattca 15360
ctatctactt gggccagtgt gcggccatca attgggcatt tgatgtacat tatcatagac 15420
catcagggaa atatcagatg ggtgagctgt tgtcatcgtt cctttctaga atgagcaaag 15480
gagtgtttaa ggtgcttgtc aatgctctaa gccacccaaa gatctacaag aaattctggc 15540
attgtggtat tatagagcct atccatggtc cttcacttga tgctcaaaac ttgcacacaa 15600
ctgtgtgcaa catggtttac acatgctata tgacctacct cgacctgttg ttgaatgaag 15660
agttagaaga gttcacattt ctcttgtgtg aaagcgacga ggatgtagta ccggacagat 15720
tcgacaacat ccaggcaaaa cacttatgtg ttctggcaga tttgtactgt caaccaggga 15780
cctgcccacc aattcgaggt ctaagaccgg tagagaaatg tgcagttcta accgaccata 15840
tcaaggcaga ggctatgtta tctccagcag gatcttcgtg gaacataaat ccaattattg 15900
tagaccatta ctcatgctct ctgacttatc tccggcgagg atcgatcaaa cagataagat 15960
tgagagttga tccaggattc attttcgacg ccctcgctga ggtaaatgtc agtcagccaa 16020
agatcggcag caacaacatc tcaaatatga gcatcaaggc tttcagaccc ccacacgatg 16080
atgttgcaaa attgctcaaa gatatcaaca caagcaagca caatcttccc atttcagggg 16140
gcaatctcgc caattatgaa atccatgctt tccgcagaat cgggttgaac tcatctgctt 16200
gctacaaagc tgttgagata tcaacattaa ttaggagatg ccttgagcca ggggaggacg 16260
gcttgttctt gggtgaggga tcgggttcta tgttgatcac ttataaagag atacttaaac 16320
taaacaagtg cttctataat agtggggttt ccgccaattc tagatctggt caaagggaat 16380
tagcacccta tccctccgaa gttggccttg tcgaacacag aatgggagta ggtaatattg 16440
tcaaagtgct ctttaacggg aggcccgaag tcacgtgggt aggcagtgta gattgcttca 16500
atttcatagt tagtaatatc cctacctcta gtgtggggtt tatccattca gatatagaga 16560
ccttgcctga caaagatact atagagaagc tagaggaatt ggcagccatc ttatcgatgg 16620
ctctgctcct gggcaaaata ggatcaatac tggtgattaa gcttatgcct ttcagcgggg 16680
attttgttca gggatttata agttatgtag ggtctcatta tagagaagtg aaccttgtat 16740
accctagata cagcaacttc atctctactg aatcttattt ggttatgaca gatctcaagg 16800
ctaaccggct aatgaatcct gaaaagatta agcagcagat aattgaatca tctgtgagga 16860
cttcacctgg acttataggt cacatcctat ccattaagca actaagctgc atacaagcaa 16920
ttgtgggaga cgcagttagt agaggtgata tcaatcctac tctgaaaaaa cttacaccta 16980

-continued

```
tagagcaggt gctgatcaat tgcgggttgg caattaacgg acctaagctg tgcaaagaat  17040

tgatccacca tgatgttgcc tcagggcaag atggattgct taattctata ctcatcctct  17100

acagggagtt ggcaagattc aaagacaacc aaagaagtca acaagggatg ttccacgctt  17160

accccgtatt ggtaagtagc aggcaacgag aacttatatc taggatcacc cgcaaattct  17220

gggggcacat tcttctttac tccgggaaca aaaagttgat aaataagttt atccagaatc  17280

tcaagtccgg ctatctgata ctagacttac accagaatat cttcgttaag aatctatcca  17340

agtcagagaa acagattatt atgacggggg gtttgaaacg tgagtgggtt tttaaggtaa  17400

cagtcaagga gaccaaagaa tggtataagt tagtcggata cagtgccctg attaaggact  17460

aattggttga actccggaac cctaatcctg ccctaggtgg ttaggcatta tttgcaatat  17520

attaaagaaa actttgaaaa tacgaagttt ctattcccag ctttgtctgg            17570


<210> SEQ ID NO 6
<211> LENGTH: 18400
<212> TYPE: DNA
<213> ORGANISM: Artificial
<220> FEATURE:
<223> OTHER INFORMATION: recombinant measles virus expressing fused
      mouse IL-12  with MV H protein specifically targeting human CEA
      antigen (MeVac P-FmIL-12 Hbl-antiCEA)

<400> SEQUENCE: 6

accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtgaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcgg gaacaaggaa atctcagata ttgaagtgca agaccctgag ggattcaaca    600

tgattctggg taccatccta gcccaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggatatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200

ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggggca aggaagatag gagggtcaaa cagagtcgag   1440
```

gagaagccag ggagagctac agagaaaccg ggcccagcag agcaagtgat gcgagagctg 1500
cccatcttcc aaccggcaca cccctagaca ttgacactgc aacggagtcc agccaagatc 1560
cgcaggacag tcgaaggtca gctgacgccc tgcttaggct gcaagccatg gcaggaatct 1620
cggaagaaca aggctcagac acggacaccc ctatagtgta caatgacaga aatcttctag 1680
actaggtgcg agaggccgag ggccagaaca acatccgcct accatccatc attgttataa 1740
aaaacttagg aaccaggtcc acacagccgc cagcccatca accatccact cccacgattg 1800
gagccaatgg cagaagagca ggcacgccat gtcaaaaacg gactggaatg catccgggct 1860
ctcaaggccg agcccatcgg ctcactggcc atcgaggaag ctatggcagc atggtcagaa 1920
atatcagaca acccaggaca ggagcgagcc acctgcaggg aagagaaggc aggcagttcg 1980
ggtctcagca aaccatgcct ctcagcaatt ggatcaactg aaggcggtgc acctcgcatc 2040
cgcggtcagg gacctggaga gagcgatgac gacgctgaaa ctttgggaat ccccccaaga 2100
aatctccagg catcaagcac tgggttacag tgttattacg tttatgatca cagcggtgaa 2160
gcggttaagg gaatccaaga tgctgactct atcatggttc aatcaggcct tgatggtgat 2220
agcaccctct caggaggaga caatgaatct gaaaacagcg atgtggatat tggcgaacct 2280
gataccgagg gatatgctat cactgaccgg ggatctgctc ccatctctat ggggttcagg 2340
gcttctgatg ttgaaactgc agaaggaggg gagatccacg agctcctgag actccaatcc 2400
agaggcaaca actttccgaa gcttgggaaa actctcaatg ttcctccgcc cccggacccc 2460
ggtagggcca gcacttccgg gacacccatt aaaaagggca cagacgcgag attagcctca 2520
tttggaacgg agatcgcgtc tttattgaca ggtggtgcaa cccaatgtgc tcgaaagtca 2580
ccctcggaac catcagggcc aggtgcacct gcggggaatg tccccgagtg tgtgagcaat 2640
gccgcactga tacaggagtg gacacccgaa tctggtacca caatctcccc gagatcccag 2700
aataatgaag aagggggaga ctattatgat gatgagctgt tctctgatgt ccaagatatt 2760
aaaacagcct tggccaaaat acacgaggat aatcagaaga taatctccaa gctagaatca 2820
ctgctgttat tgaagggaga agttgagtca attaagaagc agatcaacag gcaaaatatc 2880
agcatatcca ccctggaagg acacctctca agcatcatga tcgccattcc tggacttggg 2940
aaggatccca acgaccccac tgcagatgtc gaaatcaatc ccgacttgaa acccatcata 3000
ggcagagatt caggccgagc actggccgaa gttctcaaga aacccgttgc cagccgacaa 3060
ctccaaggaa tgacaaatgg acggaccagt tccagaggac agctgctgaa ggaatttcag 3120
ctaaagccga tcgggaaaaa gatgagctca gccgtcgggt ttgttcctga caccggccct 3180
gcatcacgca gtgtaatccg ctccattata aaatccagcc ggctagagga ggatcggaag 3240
cgttacctga tgactctcct tgatgatatc aaaggagcca atgatcttgc caagttccac 3300
cagatgctga tgaagataat aatgaagtag ctacagctca acttacctgc caaccccatg 3360
ccagtcgacc caactagcaa cctaaatcca ttataaaaaa cttaggaacc aggtccacac 3420
agctcgagtc gcgcgtggcc accatgtgtc ctcagaagct aaccatctcc tggtttgcca 3480
tcgttttgct ggtgtcccca ctcatggcca tgtgggagct ggagaaagac gtttatgttg 3540
tagaggtgga ctggactccc gatgcccctg gagaaacagt gaacctcacc tgtgacacgc 3600
ctgaagaaga tgacatcacc tggacctcag accagagaca tggagtcata ggctctggaa 3660
agaccctgac catcactgtc aaagagtttc tagatgctgg ccagtacacc tgccacaaag 3720
gaggcgagac tctgagccac tcacatctgc tgctccacaa gaaggaaaat ggaatttggt 3780

```
ccactgaaat tttaaaaaat ttcaaaaaca agactttcct gaagtgtgaa gcaccaaatt   3840
actccggacg gttcacgtgc tcatggctgg tgcaaagaaa catggacttg aagttcaaca   3900
tcaagagcag tagcagttcc cctgactctc gggcagtgac atgtggaatg gcgtctctgt   3960
ctgcagagaa ggtcacactg gaccaaaggg actatgagaa gtattcagtg tcctgccagg   4020
aggatgtcac ctgcccaact gccgaggaga ccctgcccat tgaactggcg ttggaagcac   4080
ggcagcagaa taaatatgag aactacagca ccagcttctt catcagggac atcatcaaac   4140
cagacccgcc caagaacttg cagatgaagc ctttgaagaa ctcacaggtg gaggtcagct   4200
gggagtaccc tgactcctgg agcactcccc attcctactt ctccctcaag ttctttgttc   4260
gaatccagcg caagaaagaa aagatgaagg agacagagga ggggtgtaac cagaaaggtg   4320
cgttcctcgt agagaagaca tctaccgaag tccaatgcaa aggcgggaat gtctgcgtgc   4380
aagctcagga tcgctattac aattcctcgt gcagcaagtg ggcatgtgtt ccctgcaggg   4440
tccgatccgg tggcggtggc tcgggcggtg gtgggtcggg tggcggcgga tctagggtca   4500
ttccagtctc tggacctgcc aggtgtctta gccagtcccg aaacctgctg aagaccacag   4560
atgacatggt gaagacggcc agagaaaaac tgaaacatta ttcctgcact gctgaagaca   4620
tcgatcatga agacatcaca cgggaccaaa ccagcacatt gaagacctgt ttaccactgg   4680
aactacacaa gaacgagagt tgcctggcta ctagagagac ttcttccaca acaagaggga   4740
gctgcctgcc cccacagaag acgtctttga tgatgaccct gtgccttggt agcatctatg   4800
aggacttgaa gatgtaccag acagagttcc aggccatcaa cgcagcactt cagaatcaca   4860
accatcagca gatcattcta gacaagggca tgctggtggc catcgatgag ctgatgcagt   4920
ctctgaatca taatggcgag actctgcgcc agaaacctcc tgtgggagaa gcagaccctt   4980
acagagtgaa aatgaagctc tgcatcctgc ttcacgcctt cagcacccgc gtcgtgacca   5040
tcaacagggt gatgggctat ctgagctccg cctgataatc gcgcgcgtgc tagtacaacc   5100
taaatccatt ataaaaaact taggagcaaa gtgattgcct cccaaggtcc acaatgacag   5160
agacctacga cttcgacaag tcggcatggg acatcaaagg gtcgatcgct ccgatacaac   5220
ccaccaccta cagtgatggc aggctggtgc cccaggtcag agtcatagat cctggtctag   5280
gcgacaggaa ggatgaatgc tttatgtaca tgtttctgct ggggggttgtt gaggacagcg   5340
attccctagg gcctccaatc gggcgagcat ttgggttcct gcccttaggt gttggcagat   5400
ccacagcaaa gcccgaaaaa ctcctcaaag aggccactga gcttgacata gttgttagac   5460
gtacagcagg gctcaatgaa aaactggtgt tctacaacaa caccccacta actctcctca   5520
caccttggag aaaggtccta acaacaggga gtgtcttcaa cgcaaaccaa gtgtgcaatg   5580
cggttaatct gataccgctc gataccccgc agaggttccg tgttgtttat atgagcatca   5640
cccgtctttc ggataacggg tattacaccg ttcctagaag aatgctggaa ttcagatcgg   5700
tcaatgcagt ggccttcaac ctgctggtga cccttaggat tgacaaggcg ataggccctg   5760
ggaagatcat cgacaataca gagcaacttc ctgaggcaac atttatggtc cacatcggga   5820
acttcaggag aaagaagagt gaagtctact ctgccgatta ttgcaaaatg aaaatcgaaa   5880
agatgggcct ggtttttgca cttggtggga tagggggcac cagtcttcac attagaagca   5940
caggcaaaat gagcaagact ctccatgcac aactcgggtt caagaagacc ttatgttacc   6000
cgctgatgga tatcaatgaa gaccttaatc gattactctg gaggagcaga tgcaagatag   6060
taagaatcca ggcagttttg cagccatcag ttcctcaaga attccgcatt tacgacgacg   6120
tgatcataaa tgatgaccaa ggactattca aagttctgta gaccgtagtg cccagcaatg   6180
```

-continued

```
cccgaaaacg accccccctca caatgacagc cagaaggccc ggacaaaaaa gccccctccg   6240
aaagactcca cggaccaagc gagaggccag ccagcagccg acggcaagcg cgaacaccag   6300
gcggccccag cacagaacag ccctgacaca aggccaccac cagccacccc aatctgcatc   6360
ctcctcgtgg gacccccgag gaccaacccc caaggctgcc cccgatccaa accaccaacc   6420
gcatccccac caccccccggg aaagaaaccc ccagcaattg gaaggcccct ccccctcttc   6480
ctcaacacaa gaactccaca accgaaccgc acaagcgacc gaggtgaccc aaccgcaggc   6540
atccgactcc ctagacagat cctctctccc cggcaaacta aacaaaactt agggccaagg   6600
aacatacaca cccaacagaa cccagacccc ggcccacggc gccgcgcccc caaccccccga   6660
caaccagagg gagcccccaa ccaatcccgc cggctccccc ggtgcccaca ggcagggaca   6720
ccaacccccg aacagaccca gcacccaacc atcgacaatc caagacgggg gggccccccc   6780
aaaaaaaggc ccccaggggc cgacagccag caccgcgagg aagcccaccc accccacaca   6840
cgaccacggc aaccaaacca gaacccagac caccctgggc caccagctcc cagactcggc   6900
catcaccccg cagaaaggaa aggccacaac ccgcgcaccc cagccccgat ccggcgggga   6960
gccacccaac ccgaaccagc acccaagagc gatccccgaa ggacccccga accgcaaagg   7020
acatcagtat cccacagcct ctccaagtcc cccggtctcc tcctcttctc gaagggacca   7080
aaagatcaat ccaccacacc cgacgacact caactcccca cccctaaagg agacaccggg   7140
aatcccagaa tcaagactca tccaatgtcc atcatgggtc tcaaggtgaa cgtctctgcc   7200
atattcatgg cagtactgtt aactctccaa acacccaccg gtcaaatcca ttggggcaat   7260
ctctctaaga taggggtggt aggaatagga agtgcaagct acaaagttat gactcgttcc   7320
agccatcaat cattagtcat aaaattaatg cccaatataa ctctcctcaa taactgcacg   7380
agggtagaga ttgcagaata caggagacta ctgagaacag ttttggaacc aattagagat   7440
gcacttaatg caatgaccca gaatataaga ccggttcaga gtgtagcttc aagtaggaga   7500
cacaagagat ttgcgggagt agtcctggca ggtgcggccc taggcgttgc cacagctgct   7560
cagataacag ccggcattgc acttcaccag tccatgctga actctcaagc catcgacaat   7620
ctgagagcga gcctggaaac tactaatcag gcaattgaga caatcagaca agcagggcag   7680
gagatgatat tggctgttca gggtgtccaa gactacatca ataatgagct gataccgtct   7740
atgaaccaac tatcttgtga tttaatcggc cagaagctcg ggctcaaatt gctcagatac   7800
tatacagaaa tcctgtcatt atttggcccc agtttacggg accccatatc tgcggagata   7860
tctatccagg ctttgagcta tgcgcttgga ggagacatca ataaggtgtt agaaaagctc   7920
ggatacagtg gaggtgattt actgggcatc ttagagagcg gaggaataaa ggcccggata   7980
actcacgtcg acacagagtc ctacttcatt gtcctcagta tagcctatcc gacgctgtcc   8040
gagattaagg gggtgattgt ccaccggcta gagggggtct cgtacaacat aggctctcaa   8100
gagtggtata ccactgtgcc caagtatgtt gcaacccaag ggtaccttat ctcgaatttt   8160
gatgagtcat cgtgtacttt catgccagag gggactgtgt gcagccaaaa tgccttgtac   8220
ccgatgagtc ctctgctcca agaatgcctc cgggggtaca ccaagtcctg tgctcgtaca   8280
ctcgtatccg ggtcttttgg gaaccggttc attttatcac aagggaacct aatagccaat   8340
tgtgcatcaa tcctttgcaa gtgttacaca acaggaacga tcattaatca agaccctgac   8400
aagatcctaa catacattgc tgccgatcac tgcccggtag tcgaggtgaa cggcgtgacc   8460
atccaagtcg ggagcaggag gtatccagac gctgtgtact tgcacagaat tgacctcggt   8520
```

-continued

```
cctcccatat cattggagag gttggacgta gggacaaatc tggggaatgc aattgctaag   8580
ttggaggatg ccaaggaatt gttggagtca tcggaccaga tattgaggag tatgaaaggt   8640
ttatcgagca ctagcatagt ctacatcctg attgcagtgt gtcttggagg gttgataggg   8700
atccccgctt taatatgttg ctgcaggggg cgttgtaaca aaaagggaga acaagttggt   8760
atgtcaagac caggcctaaa gcctgatctt acgggaacat caaaatccta tgtaaggtcg   8820
ctctgatcct ctacaactct tgaaacacaa atgtcccaca agtctcctct tcgtcatcaa   8880
gcaaccaccg cacccagcat caagcccacc tgaaattatc tccggcttcc ctctggccga   8940
acaatatcgg tagttaatca aaacttaggg tgcaagatca tccacaatgt caccacaacg   9000
agaccggata aatgccttct acaaagataa cccccatccc aagggaagta ggatagtcat   9060
taacagagaa catcttatga ttgatagacc ttatgttttg ctggctgttc tgtttgtcat   9120
gtttctgagc ttgatcgggt tgctagccat tgcaggcatt agacttcatc gggcagccat   9180
ctacaccgca gagatccata aaagcctcag caccaatcta gatgtaacta actcaatcga   9240
gcatcaggtc aaggacgtgc tgacaccact cttcaaaatc atcggtgatg aagtgggcct   9300
gaggacacct cagagattca ctgacctagt gaaattaatc tctgacaaga ttaaattcct   9360
taatccggat agggagtacg acttcagaga tctcacttgg tgtatcaacc cgccagagag   9420
aatcaaattg gattatgatc aatactgtgc agatgtggct gctgaagagc tcatgaatgc   9480
attggtgaac tcaactctac tggagaccag aacaaccaat cagttcctag ctgtctcaaa   9540
gggaaactgc tcagggccca ctacaatcag aggtcaattc tcaaacatgt cgctgtccct   9600
gttagacttg tatttaggtc gaggttacaa tgtgtcatct atagtcacta tgacatccca   9660
gggaatgtat gggggaactt acctagtgga aaagcctaat ctgagcagca aaaggtcaga   9720
gttgtcacaa ctgagcatgt accgagtgtt tgaagtaggt gttatcagaa atccgggttt   9780
gggggctccg gtgttccata tgacaaacta tcttgagcaa ccagtcagta atgatctcag   9840
caactgtatg gtggctttgg gggagctcaa actcgcagcc ctttgtcacg gggaagattc   9900
tatcacaatt ccctatcagg gatcagggaa aggtgtcagc ttccagctcg tcaagctagg   9960
tgtctggaaa tccccaaccg acatgcaatc ctgggtcccc ttatcaacgg atgatccagt  10020
gatagacagg ctttacctct catctcacag aggtgttatc gctgacaatc aagcaaaatg  10080
ggctgtcccg acaacacgaa cagatgacaa gttgcgaatg gagacatgct tccaacaggc  10140
gtgtaagggt aaaatccaag cactctgcga gaatcccgag tgggcaccat tgaaggataa  10200
caggattcct tcatacgggg tcttgtctgt tgatctgagt ctgacagttg agcttaaaat  10260
caaaattgct tcgggattcg ggccattgat cacacacggt tcagggatgg acctatacaa  10320
atccaaccac aacaatgtgt attggctgac tatcccgcca atgaagaacc tagccttagg  10380
tgtaatcaac acattggagt ggataccgag attcaaggtt agtcccgcac tcttcactgt  10440
cccaattaag gaagcaggcg aagactgcca tgccccaaca tacctacctg cggaggtgga  10500
tggtgatgtc aaactcagtt ccaatctggt gattctacct ggtcaagatc tccaatatgt  10560
tttggcaacc tacgatactt ccgcggttga acatgctgtg gtttattacg tttacagccc  10620
aagccgccta tcgtcttact tttatccttt taggttgcct ataaaggggg tccccatcga  10680
attacaagtg gaatgcttca catgggacca aaaactctgg tgccgtcact tctgtgtgct  10740
tgcggactca gaatctggtg gacatatcac tcactctggg atggtgggca tgggagtcag  10800
ctgcacagtc acccgggaag atggaaccaa tgcggcccag ccggccatcg agggaaggat  10860
ggctcaggtg aaactgcagc agtctggggc agaacttgtg aggtcaggga cctcagtcaa  10920
```

gttgtcctgc acagcttctg gcttcaacat taaagactcc tatatgcact ggttgaggca 10980
ggggcctgaa cagtgcctcg agtggattgg atggattgat cctgagaatg gtgatactga 11040
atatgccccg aagttccagg gcaaggccac ttttactaca gacacatcct ccaacacagc 11100
ctacctgcag ctcagcagcc tgacatctga ggacactgcc gtctattatt gtaatgaggg 11160
gactccgact gggccgtact actttgacta ctggggccaa gggaccacgg tcaccgtctc 11220
ctcaggtgga ggcggttcag gcggaggtgg ctctggcggt ggcggatcag aaaatgtgct 11280
cacccagtct ccagcaatca tgtctgcatc tccaggggag aaggtcacca taacctgcag 11340
tgccagctca agtgtaagtt acatgcactg gttccagcag aagccaggca cttctcccaa 11400
actctggatt tatagcacat ccaacctggc ttctggagtc cctgctcgct tcagtggcag 11460
tggatctggg acctcttact ctctcacaat cagccgaatg gaggctgaag atgctgccac 11520
ttattactgc cagcaaagga gtagttaccc actcacgttc ggttgtggca ccaagctcga 11580
gctgaaacgg gcggccgcaa gaggttctca tcaccatcac catcactaat agggctgcta 11640
gtgaaccaat cacatgatgt cacccagaca tcaggcatac ccactagtgt gaaatagaca 11700
tcagaattaa gaaaaacgta gggtccaagt ggttccccgt tatggactcg ctatctgtca 11760
accagatctt ataccctgaa gttcacctag atagcccgat agttaccaat aagatagtag 11820
ccatcctgga gtatgctcga gtccctcacg cttacagcct ggaggaccct acactgtgtc 11880
agaacatcaa gcaccgccta aaaaacggat tttccaacca aatgattata aacaatgtgg 11940
aagttgggaa tgtcatcaag tccaagctta ggagttatcc ggcccactct catattccat 12000
atccaaattg taatcaggat ttatttaaca tagaagacaa agagtcaacg aggaagatcc 12060
gtgaactcct caaaaagggg aattcgctgt actccaaagt cagtgataag gttttccaat 12120
gcttaaggga cactaactca cggcttggcc taggctccga attgagggag gacatcaagg 12180
agaaagttat taacttggga gtttacatgc acagctccca gtggtttgag ccctttctgt 12240
tttggtttac agtcaagact gagatgaggt cagtgattaa atcacaaacc catacttgcc 12300
ataggaggag acacacacct gtattcttca ctggtagttc agttgagttg ctaatctctc 12360
gtgaccttgt tgctataatc agtaaagagt ctcaacatgt atattacctg acatttgaac 12420
tggttttgat gtattgtgat gtcatagagg ggaggttaat gacagagacc gctatgacta 12480
ttgatgctag gtatacagag cttctaggaa gagtcagata catgtggaaa ctgatagatg 12540
gtttcttccc tgcactcggg aatccaactt atcaaattgt agccatgctg gagcctcttt 12600
cacttgctta cctgcagctg agggatataa cagtagaact cagaggtgct ttccttaacc 12660
actgctttac tgaaatacat gatgttcttg accaaaacgg gttttctgat gaaggtactt 12720
atcatgagtt aactgaagct ctagattaca ttttcataac tgatgacata catctgacag 12780
gggagatttt ctcatttttc agaagtttcg gccaccccag acttgaagca gtaacggctg 12840
ctgaaaatgt taggaaatac atgaatcagc ctaaagtcat tgtgtatgag actctgatga 12900
aaggtcatgc catattttgt ggaatcataa tcaacggcta tcgtgacagg cacggaggca 12960
gttggccacc gctgaccctc cccctgcatg ctgcagacac aatccggaat gctcaagctt 13020
caggtgaagg gttaacacat gagcagtgcg ttgataactg gaaatctttt gctggagtga 13080
aatttggctg ctttatgcct cttagcctgg atagtgatct gacaatgtac ctaaaggaca 13140
aggcacttgc tgctctccaa agggaatggg attcagttta cccgaaagag ttcctgcgtt 13200
acgaccctcc caagggaacc gggtcacgga ggcttgtaga tgttttcctt aatgattcga 13260

-continued

```
gctttgaccc atatgatgtg ataatgtatg ttgtaagtgg agcttacctc catgaccctg  13320
agttcaacct gtcttacagc ctgaaagaaa aggagatcaa ggaaacaggt agactttttg  13380
ctaaaatgac ttacaaaatg agggcatgcc aagtgattgc tgaaaatcta atctcaaacg  13440
ggattggcaa atattttaag gacaatggga tggccaagga tgagcacgat ttgactaagg  13500
cactccacac tctagctgtc tcaggagtcc ccaaagatct caaagaaagt cacagggggg  13560
ggccagtctt aaaaacctac tcccgaagcc cagtccacac aagtaccagg aacgtgagag  13620
cagcaaaagg gtttataggg ttccctcaag taattcggca ggaccaagac actgatcatc  13680
cggagaatat ggaagcttac gagacagtca gtgcatttat cacgactgat ctcaagaagt  13740
actgccttaa ttggagatat gagaccatca gcttgtttgc acagaggcta aatgagattt  13800
acggattgcc ctcatttttc cagtggctgc ataagaggct tgagacctct gtcctgtatg  13860
taagtgaccc tcattgcccc cccgaccttg acgcccatat cccgttatat aaagtcccca  13920
atgatcaaat cttcattaag taccctatgg gaggtataga agggtattgt cagaagctgt  13980
ggaccatcag caccattccc tatctatacc tggctgctta tgagagcgga gtaaggattg  14040
cttcgttagt gcaaggggac aatcagacca tagccgtaac aaaaagggta cccagcacat  14100
ggccctacaa ccttaagaaa cgggaagctg ctagagtaac tagagattac tttgtaattc  14160
ttaggcaaag gctacatgat attggccatc acctcaaggc aaatgagaca attgtttcat  14220
cacatttttt tgtctattca aaaggaatat attatgatgg gctacttgtg tcccaatcac  14280
tcaagagcat cgcaagatgt gtattctggt cagagactat agttgatgaa acaagggcag  14340
catgcagtaa tattgctaca acaatggcta aaagcatcga gagaggttat gaccgttacc  14400
ttgcatattc cctgaacgtc ctaaaagtga tacagcaaat tctgatctct cttggcttca  14460
caatcaattc aaccatgacc cgggatgtag tcatacccct cctcacaaac aacgacctct  14520
taataaggat ggcactgttg cccgctccta ttgggggggat gaattatctg aatatgagca  14580
ggctgtttgt cagaaacatc ggtgatccag taacatcatc aattgctgat ctcaagagaa  14640
tgattctcgc ctcactaatg cctgaagaga ccctccatca agtaatgaca caacaaccgg  14700
gggactcttc attcctagac tgggctagcg acccttactc agcaaatctt gtatgtgtcc  14760
agagcatcac tagactcctc aagaacataa ctgcaaggtt tgtcctgatc catagtccaa  14820
acccaatgtt aaaaggatta ttccatgatg acagtaaaga agaggacgag ggactggcgg  14880
cattcctcat ggacaggcat attatagtac ctagggcagc tcatgaaatc ctggatcata  14940
gtgtcacagg ggcaagagag tctattgcag gcatgctgga taccacaaaa ggcttgattc  15000
gagccagcat gaggaagggg gggttaacct ctcgagtgat aaccagattg tccaattatg  15060
actatgaaca attcagagca gggatggtgc tattgacagg aagaaagaga aatgtcctca  15120
ttgacaaaga gtcatgttca gtgcagctgg cgagagctct aagaagccat atgtgggcga  15180
ggctagctcg aggacggcct atttacggcc ttgaggtccc tgatgtacta gaatctatgc  15240
gaggccacct tattcggcgt catgagacat gtgtcatctg cgagtgtgga tcagtcaact  15300
acggatggtt ttttgtcccc tcgggttgcc aactggatga tattgacaag gaaacatcat  15360
ccttgagagt cccatatatt ggttctacca ctgatgagag aacagacatg aagcttgcct  15420
tcgtaagagc ccccaagtcga tccttgcgat ctgctgttag aatagcaaca gtgtactcat  15480
gggcttacgg tgatgatgat agctcttgga acgaagcctg gttgttggct aggcaaaggg  15540
ccaatgtgag cctggaggag ctaagggtga tcactcccat ctcaacttcg actaatttag  15600
cgcataggtt gagggatcgt agcactcaag tgaaatactc aggtacatcc cttgtccgag  15660
```

-continued

```
tggcgaggta taccacaatc tccaacgaca atctctcatt tgtcatatca gataagaagg  15720
ttgatactaa ctttatatac caacaaggaa tgcttctagg gttgggtgtt ttagaaacat  15780
tgtttcgact cgagaaagat accggatcat ctaacacggt attacatctt cacgtcgaaa  15840
cagattgttg cgtgatcccg atgatagatc atcccaggat acccagctcc cgcaagctag  15900
agctgagggc agagctatgt accaacccat tgatatatga taatgcacct ttaattgaca  15960
gagatgcaac aaggctatac acccagagcc ataggaggca ccttgtggaa tttgttacat  16020
ggtccacacc ccaactatat cacattttag ctaagtccac agcactatct atgattgacc  16080
tggtaacaaa atttgagaag gaccatatga atgaaatttc agctctcata ggggatgacg  16140
atatcaatag tttcataact gagtttctgc tcatagagcc aagattattc actatctact  16200
tgggccagtg tgcggccatc aattgggcat ttgatgtaca ttatcataga ccatcaggga  16260
aatatcagat gggtgagctg ttgtcatcgt tcctttctag aatgagcaaa ggagtgttta  16320
aggtgcttgt caatgctcta agccacccaa agatctacaa gaaattctgg cattgtggta  16380
ttatagagcc tatccatggt ccttcacttg atgctcaaaa cttgcacaca actgtgtgca  16440
acatggttta cacatgctat atgacctacc tcgacctgtt gttgaatgaa gagttagaag  16500
agttcacatt tctcttgtgt gaaagcgacg aggatgtagt accggacaga ttcgacaaca  16560
tccaggcaaa acacttatgt gttctggcag atttgtactg tcaaccaggg acctgcccac  16620
caattcgagg tctaagaccg gtagagaaat gtgcagttct aaccgaccat atcaaggcag  16680
aggctatgtt atctccagca ggatcttcgt ggaacataaa tccaattatt gtagaccatt  16740
actcatgctc tctgacttat ctccggcgag gatcgatcaa acagataaga ttgagagttg  16800
atccaggatt cattttcgac gccctcgctg aggtaaatgt cagtcagcca aagatcggca  16860
gcaacaacat ctcaaatatg agcatcaagg ctttcagacc cccacacgat gatgttgcaa  16920
aattgctcaa agatatcaac acaagcaagc acaatcttcc catttcaggg ggcaatctcg  16980
ccaattatga aatccatgct ttccgcagaa tcgggttgaa ctcatctgct tgctacaaag  17040
ctgttgagat atcaacatta attaggagat gccttgagcc aggggaggac ggcttgttct  17100
tgggtgaggg atcgggttct atgttgatca cttataaaga gatacttaaa ctaaacaagt  17160
gcttctataa tagtggggtt tccgccaatt ctagatctgg tcaaagggaa ttagcaccct  17220
atccctccga agttggcctt gtcgaacaca gaatgggagt aggtaatatt gtcaaagtgc  17280
tctttaacgg gaggcccgaa gtcacgtggg taggcagtgt agattgcttc aatttcatag  17340
ttagtaatat ccctacctct agtgtggggt ttatccattc agatatagag accttgcctg  17400
acaaagatac tatagagaag ctagaggaat tggcagccat cttatcgatg gctctgctcc  17460
tgggcaaaat aggatcaata ctggtgatta agcttatgcc tttcagcggg gattttgttc  17520
agggatttat aagttatgta gggtctcatt atagagaagt gaaccttgta taccctagat  17580
acagcaactt catctctact gaatcttatt tggttatgac agatctcaag gctaaccggc  17640
taatgaatcc tgaaaagatt aagcagcaga taattgaatc atctgtgagg acttcacctg  17700
gacttatagg tcacatccta tccattaagc aactaagctg catacaagca attgtgggag  17760
acgcagttag tagaggtgat atcaatccta ctctgaaaaa acttacacct atagagcagg  17820
tgctgatcaa ttgcgggttg gcaattaacg gacctaagct gtgcaaagaa ttgatccacc  17880
atgatgttgc ctcagggcaa gatggattgc ttaattctat actcatcctc tacagggagt  17940
tggcaagatt caaagacaac caaagaagtc aacaagggat gttccacgct taccccgtat  18000
```

-continued

```
tggtaagtag caggcaacga gaacttatat ctaggatcac ccgcaaattc tgggggcaca  18060

ttcttcttta ctccgggaac aaaaagttga taaataagtt tatccagaat ctcaagtccg  18120

gctatctgat actagactta caccagaata tcttcgttaa gaatctatcc aagtcagaga  18180

aacagattat tatgacgggg ggtttgaaac gtgagtgggt ttttaaggta acagtcaagg  18240

agaccaaaga atggtataag ttagtcggat acagtgccct gattaaggac taattggttg  18300

aactccggaa ccctaatcct gccctaggtg gttaggcatt atttgcaata tattaaagaa  18360

aactttgaaa atacgaagtt tctattccca gctttgtctg                        18400
```

<210> SEQ ID NO 7
<211> LENGTH: 18420
<212> TYPE: DNA
<213> ORGANISM: Artificial
<220> FEATURE:
<223> OTHER INFORMATION: artificial MV genome
      MeVac_P_FmIL-12_Hbl_anti_CD20

<400> SEQUENCE: 7

```
accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtgaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcgg gaacaaggaa atctcagata ttgaagtgca agaccctgag ggattcaaca    600

tgattctggg taccatccta gcccaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggatatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200

ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggggca aggaagatag gagggtcaaa cagagtcgag   1440

gagaagccag ggagagctac agagaaaccg ggcccagcag agcaagtgat gcgagagctg   1500

cccatcttcc aaccggcaca cccctagaca ttgacactgc aacggagtcc agccaagatc   1560

cgcaggacag tcgaaggtca gctgacgccc tgcttaggct gcaagccatg gcaggaatct   1620
```

```
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
ccagtcgacc caactagcaa cctaaatcca ttataaaaaa cttaggaacc aggtccacac   3420
agctcgagtc gcgcgtggcc accatgtgtc ctcagaagct aaccatctcc tggtttgcca   3480
tcgttttgct ggtgtcccca ctcatggcca tgtgggagct ggagaaagac gtttatgttg   3540
tagaggtgga ctggactccc gatgcccctg gagaaacagt gaacctcacc tgtgacacgc   3600
ctgaagaaga tgacatcacc tggacctcag accagagaca tggagtcata ggctctggaa   3660
agaccctgac catcactgtc aaagagtttc tagatgctgg ccagtacacc tgccacaaag   3720
gaggcgagac tctgagccac tcacatctgc tgctccacaa gaaggaaaat ggaatttggt   3780
ccactgaaat tttaaaaaat ttcaaaaaca agactttcct gaagtgtgaa gcaccaaatt   3840
actccggacg gttcacgtgc tcatggctgg tgcaaagaaa catggacttg aagttcaaca   3900
tcaagagcag tagcagttcc cctgactctc gggcagtgac atgtggaatg gcgtctctgt   3960
ctgcagagaa ggtcacactg gaccaaaggg actatgagaa gtattcagtg tcctgccagg   4020
```

-continued

```
aggatgtcac ctgcccaact gccgaggaga ccctgcccat tgaactggcg ttggaagcac   4080
ggcagcagaa taaatatgag aactacagca ccagcttctt catcagggac atcatcaaac   4140
cagacccgcc caagaacttg cagatgaagc ctttgaagaa ctcacaggtg gaggtcagct   4200
gggagtaccc tgactcctgg agcactcccc attcctactt ctccctcaag ttctttgttc   4260
gaatccagcg caagaaagaa aagatgaagg agacagagga ggggtgtaac cagaaaggtg   4320
cgttcctcgt agagaagaca tctaccgaag tccaatgcaa aggcgggaat gtctgcgtgc   4380
aagctcagga tcgctattac aattcctcgt gcagcaagtg ggcatgtgtt ccctgcaggg   4440
tccgatccgg tggcggtggc tcgggcggtg gtgggtcggg tggcggcgga tctagggtca   4500
ttccagtctc tggacctgcc aggtgtctta gccagtcccg aaacctgctg aagaccacag   4560
atgacatggt gaagacggcc agagaaaaac tgaaacatta ttcctgcact gctgaagaca   4620
tcgatcatga agacatcaca cgggaccaaa ccagcacatt gaagacctgt ttaccactgg   4680
aactacacaa gaacgagagt tgcctggcta ctagagagac ttcttccaca acaagaggga   4740
gctgcctgcc cccacagaag acgtctttga tgatgaccct gtgccttggt agcatctatg   4800
aggacttgaa gatgtaccag acagagttcc aggccatcaa cgcagcactt cagaatcaca   4860
accatcagca gatcattcta gacaagggca tgctggtggc catcgatgag ctgatgcagt   4920
ctctgaatca taatggcgag actctgcgcc agaaacctcc tgtgggagaa gcagaccctt   4980
acagagtgaa aatgaagctc tgcatcctgc ttcacgcctt cagcacccgc gtcgtgacca   5040
tcaacagggt gatgggctat ctgagctccg cctgataatc gcgcgcgtgc tagtacaacc   5100
taaatccatt ataaaaaact taggagcaaa gtgattgcct cccaaggtcc acaatgacag   5160
agacctacga cttcgacaag tcggcatggg acatcaaagg gtcgatcgct ccgatacaac   5220
ccaccaccta cagtgatggc aggctggtgc cccaggtcag agtcatagat cctggtctag   5280
gcgacaggaa ggatgaatgc tttatgtaca tgtttctgct gggggttgtt gaggacagcg   5340
attccctagg gcctccaatc gggcgagcat ttgggttcct gcccttaggt gttggcagat   5400
ccacagcaaa gcccgaaaaa ctcctcaaag aggccactga gcttgacata gttgttagac   5460
gtacagcagg gctcaatgaa aaactggtgt tctacaacaa caccccacta actctcctca   5520
caccttggag aaaggtccta acaacaggga gtgtcttcaa cgcaaaccaa gtgtgcaatg   5580
cggttaatct gataccgctc gataccccgc agaggttccg tgttgtttat atgagcatca   5640
cccgtctttc ggataacggg tattacaccg ttcctagaag aatgctggaa ttcagatcgg   5700
tcaatgcagt ggccttcaac ctgctggtga cccttaggat tgacaaggcg ataggccctg   5760
ggaagatcat cgacaataca gagcaacttc ctgaggcaac atttatggtc cacatcggga   5820
acttcaggag aaagaagagt gaagtctact ctgccgatta ttgcaaaatg aaaatcgaaa   5880
agatgggcct ggtttttgca cttggtggga tagggggcac cagtcttcac attagaagca   5940
caggcaaaat gagcaagact ctccatgcac aactcgggtt caagaagacc ttatgttacc   6000
cgctgatgga tatcaatgaa gaccttaatc gattactctg gaggagcaga tgcaagatag   6060
taagaatcca ggcagttttg cagccatcag ttcctcaaga attccgcatt tacgacgacg   6120
tgatcataaa tgatgaccaa ggactattca aagttctgta gaccgtagtg cccagcaatg   6180
cccgaaaacg acccccctca caatgacagc cagaaggccc ggacaaaaaa gcccccctccg   6240
aaagactcca cggaccaagc gagaggccag ccagcagccg acggcaagcg cgaacaccag   6300
gcggccccag cacagaacag ccctgacaca aggccaccac cagccacccc aatctgcatc   6360
```

-continued

```
ctcctcgtgg gacccccgag gaccaacccc caaggctgcc cccgatccaa accaccaacc   6420
gcatccccac cacccccggg aaagaaaccc ccagcaattg gaaggcccct ccccctcttc   6480
ctcaacacaa gaactccaca accgaaccgc acaagcgacc gaggtgaccc aaccgcaggc   6540
atccgactcc ctagacagat cctctctccc cggcaaacta aacaaaactt agggccaagg   6600
aacatacaca cccaacagaa cccagacccc ggcccacggc gccgcgcccc caacccccga   6660
caaccagagg gagcccccaa ccaatcccgc cggctccccc ggtgcccaca ggcagggaca   6720
ccaacccccg aacagaccca gcacccaacc atcgacaatc caagacgggg gggccccccc   6780
aaaaaaaggc ccccaggggc cgacagccag caccgcgagg aagcccaccc accccacaca   6840
cgaccacggc aaccaaacca gaacccagac caccctgggc caccagctcc cagactcggc   6900
catcaccccg cagaaaggaa aggccacaac ccgcgcaccc cagccccgat ccggcgggga   6960
gccacccaac ccgaaccagc acccaagagc gatccccgaa ggacccccga accgcaaagg   7020
acatcagtat cccacagcct ctccaagtcc cccggtctcc tcctcttctc gaagggacca   7080
aaagatcaat ccaccacacc cgacgacact caactcccca cccctaaagg agacaccggg   7140
aatcccagaa tcaagactca tccaatgtcc atcatgggtc tcaaggtgaa cgtctctgcc   7200
atattcatgg cagtactgtt aactctccaa acacccaccg gtcaaatcca ttggggcaat   7260
ctctctaaga taggggtggt aggaatagga agtgcaagct acaaagttat gactcgttcc   7320
agccatcaat cattagtcat aaaattaatg cccaatataa ctctcctcaa taactgcacg   7380
agggtagaga ttgcagaata caggagacta ctgagaacag ttttggaacc aattagagat   7440
gcacttaatg caatgaccca gaatataaga ccggttcaga gtgtagcttc aagtaggaga   7500
cacaagagat ttgcgggagt agtcctggca ggtgcggccc taggcgttgc cacagctgct   7560
cagataacag ccggcattgc acttcaccag tccatgctga actctcaagc catcgacaat   7620
ctgagagcga gcctggaaac tactaatcag gcaattgaga caatcagaca agcagggcag   7680
gagatgatat tggctgttca gggtgtccaa gactacatca ataatgagct gataccgtct   7740
atgaaccaac tatcttgtga tttaatcggc cagaagctcg ggctcaaatt gctcagatac   7800
tatacagaaa tcctgtcatt atttggcccc agtttacggg accccatatc tgcggagata   7860
tctatccagg ctttgagcta tgcgcttgga ggagacatca ataaggtgtt agaaaagctc   7920
ggatacagtg gaggtgattt actgggcatc ttagagagcg gaggaataaa ggcccggata   7980
actcacgtcg acacagagtc ctacttcatt gtcctcagta tagcctatcc gacgctgtcc   8040
gagattaagg gggtgattgt ccaccggcta gagggggtct cgtacaacat aggctctcaa   8100
gagtggtata ccactgtgcc caagtatgtt gcaacccaag ggtaccttat ctcgaatttt   8160
gatgagtcat cgtgtacttt catgccagag gggactgtgt gcagccaaaa tgccttgtac   8220
ccgatgagtc ctctgctcca agaatgcctc cgggggtaca ccaagtcctg tgctcgtaca   8280
ctcgtatccg ggtcttttgg gaaccggttc attttatcac aagggaacct aatagccaat   8340
tgtgcatcaa tcctttgcaa gtgttacaca acaggaacga tcattaatca agaccctgac   8400
aagatcctaa catacattgc tgccgatcac tgcccggtag tcgaggtgaa cggcgtgacc   8460
atccaagtcg ggagcaggag gtatccagac gctgtgtact tgcacagaat tgacctcggt   8520
cctcccatat cattggagag gttggacgta gggacaaatc tggggaatgc aattgctaag   8580
ttggaggatg ccaaggaatt gttggagtca tcggaccaga tattgaggag tatgaaaggt   8640
ttatcgagca ctagcatagt ctacatcctg attgcagtgt gtcttggagg gttgataggg   8700
atccccgctt taatatgttg ctgcaggggg cgttgtaaca aaaagggaga acaagttggt   8760
```

atgtcaagac caggcctaaa gcctgatctt acgggaacat caaaatccta tgtaaggtcg 8820
ctctgatcct ctacaactct tgaaacacaa atgtcccaca agtctcctct tcgtcatcaa 8880
gcaaccaccg cacccagcat caagcccacc tgaaattatc tccggcttcc ctctggccga 8940
acaatatcgg tagttaatca aaacttaggg tgcaagatca tccacaatgt caccacaacg 9000
agaccggata aatgccttct acaaagataa cccccatccc aagggaagta ggatagtcat 9060
taacagagaa catcttatga ttgatagacc ttatgttttg ctggctgttc tgtttgtcat 9120
gtttctgagc ttgatcgggt tgctagccat tgcaggcatt agacttcatc gggcagccat 9180
ctacaccgca gagatccata aaagcctcag caccaatcta gatgtaacta actcaatcga 9240
gcatcaggtc aaggacgtgc tgacaccact cttcaaaatc atcggtgatg aagtgggcct 9300
gaggacacct cagagattca ctgacctagt gaaattaatc tctgacaaga ttaaattcct 9360
taatccggat agggagtacg acttcagaga tctcacttgg tgtatcaacc cgccagagag 9420
aatcaaattg gattatgatc aatactgtgc agatgtggct gctgaagagc tcatgaatgc 9480
attggtgaac tcaactctac tggagaccag aacaaccaat cagttcctag ctgtctcaaa 9540
gggaaactgc tcagggccca ctacaatcag aggtcaattc tcaaacatgt cgctgtccct 9600
gttagacttg tatttaggtc gaggttacaa tgtgtcatct atagtcacta tgacatccca 9660
gggaatgtat gggggaactt acctagtgga aaagcctaat ctgagcagca aaaggtcaga 9720
gttgtcacaa ctgagcatgt accgagtgtt tgaagtaggt gttatcagaa atccgggttt 9780
gggggctccg gtgttccata tgacaaacta tcttgagcaa ccagtcagta atgatctcag 9840
caactgtatg gtggctttgg gggagctcaa actcgcagcc ctttgtcacg gggaagattc 9900
tatcacaatt ccctatcagg gatcagggaa aggtgtcagc ttccagctcg tcaagctagg 9960
tgtctggaaa tccccaaccg acatgcaatc ctgggtcccc ttatcaacgg atgatccagt 10020
gatagacagg ctttacctct catctcacag aggtgttatc gctgacaatc aagcaaaatg 10080
ggctgtcccg acaacacgaa cagatgacaa gttgcgaatg gagacatgct tccaacaggc 10140
gtgtaagggt aaaatccaag cactctgcga gaatcccgag tgggcaccat tgaaggataa 10200
caggattcct tcatacgggg tcttgtctgt tgatctgagt ctgacagttg agcttaaaat 10260
caaaattgct tcgggattcg ggccattgat cacacacggt tcagggatgg acctatacaa 10320
atccaaccac aacaatgtgt attggctgac tatcccgcca atgaagaacc tagccttagg 10380
tgtaatcaac acattggagt ggataccgag attcaaggtt agtcccgcac tcttcactgt 10440
cccaattaag gaagcaggcg aagactgcca tgccccaaca tacctacctg cggaggtgga 10500
tggtgatgtc aaactcagtt ccaatctggt gattctacct ggtcaagatc tccaatatgt 10560
tttggcaacc tacgatactt ccgcggttga acatgctgtg gtttattacg tttacagccc 10620
aagccgccta tcgtcttact tttatccttt taggttgcct ataaaggggg tccccatcga 10680
attacaagtg gaatgcttca catgggacca aaaactctgg tgccgtcact tctgtgtgct 10740
tgcggactca gaatctggtg gacatatcac tcactctggg atggtgggca tgggagtcag 10800
ctgcacagtc acccgggaag atggaaccaa tgcggcccag ccggccatcg agggaaggat 10860
ggctcaggtt cagctggtcc agtcaggggc tgagctggtg aagcctgggg cctcagtgaa 10920
gatgtcctgc aaggcttctg gctacacatt taccagttac aatatgcact gggtaaagca 10980
gacacctgga cagggcctgg aatggattgg agctatttat ccaggaaatg gtgatacttc 11040
ctacaatcag aagttcaaag gcaaggccac attgactgca gacaaatcct ccagcacagc 11100

-continued

```
ctacatgcag ctcagcagcc tgacatctga ggactctgcg gtctattact gtgcaagagc  11160
gcaattacga cctaactact ggtacttcga tgtctggggc gcagggacca cggtcaccgt  11220
gagcaagatc tctggtggcg gtggctcggg cggtggtggg tcgggtggcg gaggctcggg  11280
tggctcgagc gacatcgtgc tgtcgcagtc tccagcaatc ctgtctgcat ctccagggga  11340
gaaggtcaca atgacttgca gggccagctc aagtgtaagt tacatgcact ggtaccagca  11400
gaagccagga tcctccccca aaccctggat ttatgccaca tccaacctgg cttctggagt  11460
ccctgctcgc ttcagtggca gtgggtctgg gacctcttac tctctcacaa tcagcagagt  11520
ggaggctgaa gatgctgcca cttattactg ccagcagtgg attagtaacc cacccacgtt  11580
cggtgctggg accaagctgg agctgaaggc ggccgcaaga ggttctcatc accatcacca  11640
tcactaatag ggctgctagt gaaccaatca catgatgtca cccagacatc aggcataccc  11700
actagtgtga aatagacatc agaattaaga aaaacgtagg gtccaagtgg ttccccgtta  11760
tggactcgct atctgtcaac cagatcttat accctgaagt tcacctagat agcccgatag  11820
ttaccaataa gatagtagcc atcctggagt atgctcgagt ccctcacgct tacagcctgg  11880
aggaccctac actgtgtcag aacatcaagc accgcctaaa aaacggattt tccaaccaaa  11940
tgattataaa caatgtggaa gttgggaatg tcatcaagtc caagcttagg agttatccgg  12000
cccactctca tattccatat ccaaattgta atcaggattt atttaacata gaagacaaag  12060
agtcaacgag gaagatccgt gaactcctca aaaaggggaa ttcgctgtac tccaaagtca  12120
gtgataaggt tttccaatgc ttaagggaca ctaactcacg gcttggccta ggctccgaat  12180
tgagggagga catcaaggag aaagttatta acttgggagt ttacatgcac agctcccagt  12240
ggtttgagcc ctttctgttt tggtttacag tcaagactga gatgaggtca gtgattaaat  12300
cacaaaccca tacttgccat aggaggagac acacacctgt attcttcact ggtagttcag  12360
ttgagttgct aatctctcgt gaccttgttg ctataatcag taaagagtct caacatgtat  12420
attacctgac atttgaactg gttttgatgt attgtgatgt catagagggg aggttaatga  12480
cagagaccgc tatgactatt gatgctaggt atacagagct tctaggaaga gtcagataca  12540
tgtggaaact gatagatggt ttcttccctg cactcgggaa tccaacttat caaattgtag  12600
ccatgctgga gcctctttca cttgcttacc tgcagctgag ggatataaca gtagaactca  12660
gaggtgcttt ccttaaccac tgctttactg aaatacatga tgttcttgac caaaacgggt  12720
tttctgatga aggtacttat catgagttaa ctgaagctct agattacatt ttcataactg  12780
atgacataca tctgacaggg gagattttct catttttcag aagtttcggc caccccagac  12840
ttgaagcagt aacggctgct gaaaatgtta ggaaatacat gaatcagcct aaagtcattg  12900
tgtatgagac tctgatgaaa ggtcatgcca tattttgtgg aatcataatc aacggctatc  12960
gtgacaggca cggaggcagt tggccaccgc tgaccctccc cctgcatgct gcagacacaa  13020
tccggaatgc tcaagcttca ggtgaagggt taacacatga gcagtgcgtt gataactgga  13080
aatcttttgc tggagtgaaa tttggctgct ttatgcctct tagcctggat agtgatctga  13140
caatgtacct aaaggacaag gcacttgctg ctctccaaag ggaatgggat tcagtttacc  13200
cgaaagagtt cctgcgttac gaccctccca agggaaccgg gtcacggagg cttgtagatg  13260
ttttccttaa tgattcgagc tttgacccat atgatgtgat aatgtatgtt gtaagtggag  13320
cttacctcca tgaccctgag ttcaacctgt cttacagcct gaaagaaaag gagatcaagg  13380
aaacaggtag actttttgct aaaatgactt acaaaatgag ggcatgccaa gtgattgctg  13440
aaaatctaat ctcaaacggg attggcaaat attttaagga caatgggatg gccaaggatg  13500
```

-continued

```
agcacgattt gactaaggca ctccacactc tagctgtctc aggagtcccc aaagatctca  13560
aagaaagtca caggggggggg ccagtcttaa aaacctactc ccgaagccca gtccacacaa  13620
gtaccaggaa cgtgagagca gcaaaagggt ttatagggtt ccctcaagta attcggcagg  13680
accaagacac tgatcatccg gagaatatgg aagcttacga gacagtcagt gcatttatca  13740
cgactgatct caagaagtac tgccttaatt ggagatatga gaccatcagc ttgtttgcac  13800
agaggctaaa tgagatttac ggattgccct catttttcca gtggctgcat aagaggcttg  13860
agacctctgt cctgtatgta agtgaccctc attgcccccc cgaccttgac gcccatatcc  13920
cgttatataa agtccccaat gatcaaatct tcattaagta ccctatggga ggtatagaag  13980
ggtattgtca gaagctgtgg accatcagca ccattcccta tctatacctg gctgcttatg  14040
agagcggagt aaggattgct tcgttagtgc aaggggacaa tcagaccata gccgtaacaa  14100
aaagggtacc cagcacatgg ccctacaacc ttaagaaacg ggaagctgct agagtaacta  14160
gagattactt tgtaattctt aggcaaaggc tacatgatat tggccatcac ctcaaggcaa  14220
atgagacaat tgtttcatca cattttttg tctattcaaa aggaatatat tatgatgggc  14280
tacttgtgtc ccaatcactc aagagcatcg caagatgtgt attctggtca gagactatag  14340
ttgatgaaac aagggcagca tgcagtaata ttgctacaac aatggctaaa agcatcgaga  14400
gaggttatga ccgttacctt gcatattccc tgaacgtcct aaaagtgata cagcaaattc  14460
tgatctctct tggcttcaca atcaattcaa ccatgacccg ggatgtagtc atacccctcc  14520
tcacaaacaa cgacctctta ataaggatgg cactgttgcc cgctcctatt ggggggatga  14580
attatctgaa tatgagcagg ctgtttgtca gaaacatcgg tgatccagta acatcatcaa  14640
ttgctgatct caagagaatg attctcgcct cactaatgcc tgaagagacc ctccatcaag  14700
taatgacaca acaaccgggg gactcttcat tcctagactg ggctagcgac ccttactcag  14760
caaatcttgt atgtgtccag agcatcacta gactcctcaa gaacataact gcaaggtttg  14820
tcctgatcca tagtccaaac ccaatgttaa aaggattatt ccatgatgac agtaaagaag  14880
aggacgaggg actggcggca ttcctcatgg acaggcatat tatagtacct agggcagctc  14940
atgaaatcct ggatcatagt gtcacagggg caagagagtc tattgcaggc atgctggata  15000
ccacaaaagg cttgattcga gccagcatga ggaagggggg gttaacctct cgagtgataa  15060
ccagattgtc caattatgac tatgaacaat tcagagcagg gatggtgcta ttgacaggaa  15120
gaaagagaaa tgtcctcatt gacaaagagt catgttcagt gcagctggcg agagctctaa  15180
gaagccatat gtgggcgagg ctagctcgag gacggcctat ttacggcctt gaggtccctg  15240
atgtactaga atctatgcga ggccacctta ttcggcgtca tgagacatgt gtcatctgcg  15300
agtgtggatc agtcaactac ggatggtttt ttgtcccctc gggttgccaa ctggatgata  15360
ttgacaagga aacatcatcc ttgagagtcc catatattgg ttctaccact gatgagagaa  15420
cagacatgaa gcttgccttc gtaagagccc caagtcgatc cttgcgatct gctgttagaa  15480
tagcaacagt gtactcatgg gcttacggtg atgatgatag ctcttggaac gaagcctggt  15540
tgttggctag gcaaagggcc aatgtgagcc tggaggagct aagggtgatc actcccatct  15600
caacttcgac taatttagcg cataggttga gggatcgtag cactcaagtg aaatactcag  15660
gtacatccct tgtccgagtg gcgaggtata ccacaatctc caacgacaat ctctcatttg  15720
tcatatcaga taagaaggtt gatactaact ttatatacca acaaggaatg cttctagggt  15780
tgggtgtttt agaaacattg tttcgactcg agaaagatac cggatcatct aacacggtat  15840
```

tacatcttca cgtcgaaaca gattgttgcg tgatcccgat gatagatcat cccaggatac 15900
ccagctcccg caagctagag ctgagggcag agctatgtac caacccattg atatatgata 15960
atgcaccttt aattgacaga gatgcaacaa ggctatacac ccagagccat aggaggcacc 16020
ttgtggaatt tgttacatgg tccacacccc aactatatca cattttagct aagtccacag 16080
cactatctat gattgacctg gtaacaaaat ttgagaagga ccatatgaat gaaatttcag 16140
ctctcatagg ggatgacgat atcaatagtt tcataactga gtttctgctc atagagccaa 16200
gattattcac tatctacttg ggccagtgtg cggccatcaa ttgggcattt gatgtacatt 16260
atcatagacc atcagggaaa tatcagatgg gtgagctgtt gtcatcgttc ctttctagaa 16320
tgagcaaagg agtgtttaag gtgcttgtca atgctctaag ccacccaaag atctacaaga 16380
aattctggca ttgtggtatt atagagccta tccatggtcc ttcacttgat gctcaaaact 16440
tgcacacaac tgtgtgcaac atggtttaca catgctatat gacctacctc gacctgttgt 16500
tgaatgaaga gttagaagag ttcacatttc tcttgtgtga aagcgacgag gatgtagtac 16560
cggacagatt cgacaacatc caggcaaaac acttatgtgt tctggcagat ttgtactgtc 16620
aaccagggac ctgcccacca attcgaggtc taagaccggt agagaaatgt gcagttctaa 16680
ccgaccatat caaggcagag gctatgttat ctccagcagg atcttcgtgg aacataaatc 16740
caattattgt agaccattac tcatgctctc tgacttatct ccggcgagga tcgatcaaac 16800
agataagatt gagagttgat ccaggattca ttttcgacgc cctcgctgag gtaaatgtca 16860
gtcagccaaa gatcggcagc aacaacatct caaatatgag catcaaggct ttcagacccc 16920
cacacgatga tgttgcaaaa ttgctcaaag atatcaacac aagcaagcac aatcttccca 16980
tttcaggggg caatctcgcc aattatgaaa tccatgcttt ccgcagaatc gggttgaact 17040
catctgcttg ctacaaagct gttgagatat caacattaat taggagatgc cttgagccag 17100
gggaggacgg cttgttcttg ggtgagggat cgggttctat gttgatcact tataaagaga 17160
tacttaaact aaacaagtgc ttctataata gtggggtttc cgccaattct agatctggtc 17220
aaagggaatt agcaccctat ccctccgaag ttggccttgt cgaacacaga atgggagtag 17280
gtaatattgt caaagtgctc tttaacggga ggcccgaagt cacgtgggta ggcagtgtag 17340
attgcttcaa tttcatagtt agtaatatcc ctacctctag tgtggggttt atccattcag 17400
atatagagac cttgcctgac aaagatacta tagagaagct agaggaattg gcagccatct 17460
tatcgatggc tctgctcctg ggcaaaatag gatcaatact ggtgattaag cttatgcctt 17520
tcagcgggga ttttgttcag ggatttataa gttatgtagg gtctcattat agagaagtga 17580
accttgtata ccctagatac agcaacttca tctctactga atcttatttg gttatgacag 17640
atctcaaggc taaccggcta atgaatcctg aaaagattaa gcagcagata attgaatcat 17700
ctgtgaggac ttcacctgga cttataggtc acatcctatc cattaagcaa ctaagctgca 17760
tacaagcaat tgtgggagac gcagttagta gaggtgatat caatcctact ctgaaaaaac 17820
ttacacctat agagcaggtg ctgatcaatt gcgggttggc aattaacgga cctaagctgt 17880
gcaaagaatt gatccaccat gatgttgcct cagggcaaga tggattgctt aattctatac 17940
tcatcctcta cagggagttg gcaagattca aagacaacca aagaagtcaa caagggatgt 18000
tccacgctta ccccgtattg gtaagtagca ggcaacgaga acttatatct aggatcaccc 18060
gcaaattctg ggggcacatt cttctttact ccgggaacaa aaagttgata aataagttta 18120
tccagaatct caagtccggc tatctgatac tagacttaca ccagaatatc ttcgttaaga 18180
atctatccaa gtcagagaaa cagattatta tgacgggggg tttgaaacgt gagtgggttt 18240
ttaaggtaac agtcaaggag accaaagaat ggtataagtt agtcggatac agtgccctga 18300
ttaaggacta attggttgaa ctccggaacc ctaatcctgc cctaggtggt taggcattat 18360
ttgcaatata ttaaagaaaa ctttgaaaat acgaagtttc tattcccagc tttgtctggt 18420

<210> SEQ ID NO 8
<211> LENGTH: 15
<212> TYPE: DNA
<213> ORGANISM: Artificial
<220> FEATURE:
<223> OTHER INFORMATION: linker sequence

<400> SEQUENCE: 8
ggggsggggs ggggs 15

<210> SEQ ID NO 9
<211> LENGTH: 7
<212> TYPE: DNA
<213> ORGANISM: Artificial
<220> FEATURE:
<223> OTHER INFORMATION: artificial linker sequence

<400> SEQUENCE: 9 gggggs 7

<210> SEQ ID NO 10
<211> LENGTH: 543
<212> TYPE: PRT
<213> ORGANISM: Artificial
<220> FEATURE:
<223> OTHER INFORMATION: FmIL-12 fusion polypeptide

<400> SEQUENCE: 10

Met Cys Pro Gln Lys Leu Thr Ile Ser Trp Phe Ala Ile Val Leu Leu
1 5 10 15

Val Ser Pro Leu Met Ala Met Trp Glu Leu Glu Lys Asp Val Tyr Val
20 25 30

Val Glu Val Asp Trp Thr Pro Asp Ala Pro Gly Glu Thr Val Asn Leu
35 40 45

Thr Cys Asp Thr Pro Glu Glu Asp Asp Ile Thr Trp Thr Ser Asp Gln
50 55 60

Arg His Gly Val Ile Gly Ser Gly Lys Thr Leu Thr Ile Thr Val Lys
65 70 75 80

Glu Phe Leu Asp Ala Gly Gln Tyr Thr Cys His Lys Gly Gly Glu Thr
85 90 95

Leu Ser His Ser His Leu Leu Leu His Lys Lys Glu Asn Gly Ile Trp
100 105 110

Ser Thr Glu Ile Leu Lys Asn Phe Lys Asn Lys Thr Phe Leu Lys Cys
115 120 125

Glu Ala Pro Asn Tyr Ser Gly Arg Phe Thr Cys Ser Trp Leu Val Gln
130 135 140

Arg Asn Met Asp Leu Lys Phe Asn Ile Lys Ser Ser Ser Ser Ser Pro
145 150 155 160

Asp Ser Arg Ala Val Thr Cys Gly Met Ala Ser Leu Ser Ala Glu Lys
165 170 175

Val Thr Leu Asp Gln Arg Asp Tyr Glu Lys Tyr Ser Val Ser Cys Gln
180 185 190

Glu Asp Val Thr Cys Pro Thr Ala Glu Glu Thr Leu Pro Ile Glu Leu
195 200 205

-continued

```
Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                325                 330                 335

Gly Gly Gly Ser Gly Gly Gly Gly Ser Gly Gly Gly Gly Ser Arg Val
            340                 345                 350

Ile Pro Val Ser Gly Pro Ala Arg Cys Leu Ser Gln Ser Arg Asn Leu
        355                 360                 365

Leu Lys Thr Thr Asp Asp Met Val Lys Thr Ala Arg Glu Lys Leu Lys
    370                 375                 380

His Tyr Ser Cys Thr Ala Glu Asp Ile Asp His Glu Asp Ile Thr Arg
385                 390                 395                 400

Asp Gln Thr Ser Thr Leu Lys Thr Cys Leu Pro Leu Glu Leu His Lys
                405                 410                 415

Asn Glu Ser Cys Leu Ala Thr Arg Glu Thr Ser Ser Thr Thr Arg Gly
            420                 425                 430

Ser Cys Leu Pro Pro Gln Lys Thr Ser Leu Met Met Thr Leu Cys Leu
        435                 440                 445

Gly Ser Ile Tyr Glu Asp Leu Lys Met Tyr Gln Thr Glu Phe Gln Ala
    450                 455                 460

Ile Asn Ala Ala Leu Gln Asn His Asn His Gln Gln Ile Ile Leu Asp
465                 470                 475                 480

Lys Gly Met Leu Val Ala Ile Asp Glu Leu Met Gln Ser Leu Asn His
                485                 490                 495

Asn Gly Glu Thr Leu Arg Gln Lys Pro Pro Val Gly Glu Ala Asp Pro
            500                 505                 510

Tyr Arg Val Lys Met Lys Leu Cys Ile Leu Leu His Ala Phe Ser Thr
        515                 520                 525

Arg Val Val Thr Ile Asn Arg Val Met Gly Tyr Leu Ser Ser Ala
    530                 535                 540
```

<210> SEQ ID NO 11
<211> LENGTH: 1632
<212> TYPE: DNA
<213> ORGANISM: Artificial
<220> FEATURE:
<223> OTHER INFORMATION: FmIL-12 fusion polypeptide coding sequence

<400> SEQUENCE: 11

```
atgtgtcctc agaagctaac catctcctgg tttgccatcg ttttgctggt gtccccactc      60

atggccatgt gggagctgga gaaagacgtt tatgttgtag aggtggactg gactcccgat     120

gcccctggag aaacagtgaa cctcacctgt gacacgcctg aagaagatga catcacctgg     180
```

acctcagacc agagacatgg agtcataggc tctggaaaga ccctgaccat cactgtcaaa 240
gagtttctag atgctggcca gtacacctgc cacaaaggag gcgagactct gagccactca 300
catctgctgc tccacaagaa ggaaaatgga atttggtcca ctgaaatttt aaaaaatttc 360
aaaaacaaga ctttcctgaa gtgtgaagca ccaaattact ccggacggtt cacgtgctca 420
tggctggtgc aaagaaacat ggacttgaag ttcaacatca agagcagtag cagttcccct 480
gactctcggg cagtgacatg tggaatggcg tctctgtctg cagagaaggt cacactggac 540
caaagggact atgagaagta ttcagtgtcc tgccaggagg atgtcacctg cccaactgcc 600
gaggagaccc tgcccattga actggcgttg gaagcacggc agcagaataa atatgagaac 660
tacagcacca gcttcttcat cagggacatc atcaaaccag acccgcccaa gaacttgcag 720
atgaagcctt tgaagaactc acaggtggag gtcagctggg agtaccctga ctcctggagc 780
actccccatt cctacttctc cctcaagttc tttgttcgaa tccagcgcaa gaaagaaaag 840
atgaaggaga cagaggaggg gtgtaaccag aaaggtgcgt tcctcgtaga gaagacatct 900
accgaagtcc aatgcaaagg cgggaatgtc tgcgtgcaag ctcaggatcg ctattacaat 960
tcctcgtgca gcaagtgggc atgtgttccc tgcagggtcc gatccggtgg cggtggctcg 1020
ggcggtggtg ggtcgggtgg cggcggatcc agggtcattc cagtctctgg acctgccagg 1080
tgtcttagcc agtcccgaaa cctgctgaag accacagatg acatggtgaa gacggccaga 1140
gaaaaactga aacattattc ctgcactgct gaagacatcg atcatgaaga catcacacgg 1200
gaccaaacca gcacattgaa gacctgttta ccactggaac tacacaagaa cgagagttgc 1260
ctggctacta gagagacttc ttccacaaca agagggagct gcctgccccc acagaagacg 1320
tctttgatga tgaccctgtg ccttggtagc atctatgagg acttgaagat gtaccagaca 1380
gagttccagg ccatcaacgc agcacttcag aatcacaacc atcagcagat cattctagac 1440
aagggcatgc tggtggccat cgatgagctg atgcagtctc tgaatcataa tggcgagact 1500
ctgcgccaga aacctcctgt gggagaagca gacccttaca gagtgaaaat gaagctctgc 1560
atcctgcttc acgccttcag cacccgcgtc gtgaccatca acagggtgat gggctatctg 1620
agctccgcct ga 1632

<210> SEQ ID NO 12
<211> LENGTH: 532
<212> TYPE: PRT
<213> ORGANISM: Artificial
<220> FEATURE:
<223> OTHER INFORMATION: FhIL-12 fusion polypeptide

<400> SEQUENCE: 12

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

-continued

```
Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Asn Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Gly Gly Ser Arg
                325                 330                 335

Asn Leu Pro Val Ala Thr Pro Asp Pro Gly Met Phe Pro Cys Leu His
            340                 345                 350

His Ser Gln Asn Leu Leu Arg Ala Val Ser Asn Met Leu Gln Lys Ala
        355                 360                 365

Arg Gln Thr Leu Glu Phe Tyr Pro Cys Thr Ser Glu Glu Ile Asp His
    370                 375                 380

Glu Asp Ile Thr Lys Asp Lys Thr Ser Thr Val Glu Ala Cys Leu Pro
385                 390                 395                 400

Leu Glu Leu Thr Lys Asn Glu Ser Cys Leu Asn Ser Arg Glu Thr Ser
                405                 410                 415

Phe Ile Thr Asn Gly Ser Cys Leu Ala Ser Arg Lys Thr Ser Phe Met
            420                 425                 430

Met Ala Leu Cys Leu Ser Ser Ile Tyr Glu Asp Leu Lys Met Tyr Gln
        435                 440                 445

Val Glu Phe Lys Thr Met Asn Ala Lys Leu Leu Met Asp Pro Lys Arg
    450                 455                 460

Gln Ile Phe Leu Asp Gln Asn Met Leu Ala Val Ile Asp Glu Leu Met
465                 470                 475                 480

Gln Ala Leu Asn Phe Asn Ser Glu Thr Val Pro Gln Lys Ser Ser Leu
                485                 490                 495

Glu Glu Pro Asp Phe Tyr Lys Thr Lys Ile Lys Leu Cys Ile Leu Leu
            500                 505                 510

His Ala Phe Arg Ile Arg Ala Val Thr Ile Asp Arg Val Met Ser Tyr
```

515 520 525

Leu Asn Ala Ser
530

<210> SEQ ID NO 13
<211> LENGTH: 1599
<212> TYPE: DNA
<213> ORGANISM: Artificial
<220> FEATURE:
<223> OTHER INFORMATION: FhIL-12 fusion polypeptide encoding sequence

<400> SEQUENCE: 13
atgtgtcacc agcagttggt catctcttgg ttttccctgg tttttctggc atctcccctc 60
gtggccatat gggaactgaa gaaagatgtt tatgtcgtag aattggattg gtatccggat 120
gcccctggag aaatggtggt cctcacctgt gacacccctg aagaagatgg tatcacctgg 180
accttggacc agagcagtga ggtcttaggc tctggcaaaa ccctgaccat ccaagtcaaa 240
gagtttggag atgctggcca gtacacctgt cacaaaggag gcgaggttct aagccattcg 300
ctcctgctgc ttcacaaaaa ggaagatgga atttggtcca ctgatatttt aaaggaccag 360
aaagaaccca aaaataagac ctttctaaga tgcgaggcca agaattattc tggacgtttc 420
acctgctggt ggctgacgac aatcagtact gatttgacat tcagtgtcaa aagcagcaga 480
ggctcttctg acccccaagg ggtgacgtgc ggagctgcta cactctctgc agagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gaaaactaca ccagcagctt cttcatcagg gacatcatca aacctgaccc acccaacaac 720
ttgcagctga agccattaaa gaattctcgg caggtggagg tcagctggga gtaccctgac 780
acctggagta ctccacattc ctacttctcc ctgacattct gcgttcaggt ccagggcaag 840
agcaagagag aaaagaaaga tagagtcttc accgacaaga cctcagccac ggtcatctgc 900
cgcaaaaatg ccagcattag cgtgcgggcc caggaccgct actatagctc atcttggagc 960
gaatgggcat ctgtgccctg cagtggtggc ggtggcggcg gatctagaaa cctccccgtg 1020
gccactccag acccaggaat gttcccatgc cttcaccact cccaaaacct gctgagggcc 1080
gtcagcaaca tgctccagaa ggccagacaa actctagaat tttacccttg cacttctgaa 1140
gagattgatc atgaagatat cacaaaagat aaaaccagca cagtggaggc ctgtttacca 1200
ttggaattaa ccaagaatga gagttgccta aattccagag agacctcttt cataactaat 1260
gggagttgcc tggcctccag aaagacctct tttatgatgg ccctgtgcct tagtagtatt 1320
tatgaagact tgaagatgta ccaggtggag ttcaagacca tgaatgcaaa gcttctgatg 1380
gatcctaaga ggcagatctt tctagatcaa aacatgctgg cagttattga tgagctgatg 1440
caggccctga atttcaacag tgagactgtg ccacaaaaat cctcccttga agaaccggat 1500
ttttataaaa ctaaaatcaa gctctgcata cttcttcatg ctttcagaat tcgggcagtg 1560
actattgata gagtgatgag ctatctgaat gcttcctag 1599

<210> SEQ ID NO 14
<211> LENGTH: 17628
<212> TYPE: DNA
<213> ORGANISM: Artificial
<220> FEATURE:
<223> OTHER INFORMATION: artificial polynucleotide encoding Edmonston B
MV encoding a murine IL12 fusion protein

<400> SEQUENCE: 14

-continued

```
accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcga gaacaaggaa atctcagata ttgaagtgca agaccctgag ggattcaaca    600

tgattctggg taccatccta gcccaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggacatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatgggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200

ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggggca aggaagatag gagggtcaaa cagagtcgag   1440

gagaagccag ggagagctac agagaaaccg ggcccagcag agcaagtgat gcgagagctg   1500

cccatcttcc aaccggcaca cccctagaca ttgacactgc atcggagtcc agccaagatc   1560

cgcaggacag tcgaaggtca gctgacgccc tgcttaggct gcaagccatg gcaggaatct   1620

cggaagaaca aggctcagac acggacaccc ctatagtgta caatgacaga aatcttctag   1680

actaggtgcg agaggccgag gaccagaaca acatccgcct accctccatc attgttataa   1740

aaaacttagg aaccaggtcc acacagccgc cagcccatca accatccact cccacgattg   1800

gagcagatgg cagaagagca ggcacgccat gtcaaaaacg gactggaatg catccgggct   1860

ctcaaggccg agcccatcgg ctcactggcc atcgaggaag ctatggcagc atggtcagaa   1920

atatcagaca acccaggaca ggagcgagcc acctgcaggg aagagaaggc aggcagttcg   1980

ggtctcagca aaccatgcct ctcagcaatt ggatcaactg aaggcggtgc acctcgcatc   2040

cgcggtcagg gacctggaga gagcgatgac gacgctgaaa ctttgggaat ccccccaaga   2100

aatctccagg catcaagcac tgggctacag tgtcattatg tttatgatca cagcggtgaa   2160

gcggttaagg gaatccaaga tgctgactct atcatggttc aatcaggcct tgatggtgat   2220

agcaccctct caggaggaga caatgaatct gaaaacagcg atgtggatat tggcgaacct   2280

gataccgagg gatatgctat cactgaccgg ggatctgctc ccatctctat ggggttcagg   2340
```

-continued

```
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc ttcattgaca ggtggtgcaa cccaatgtgc tcgaaagtca   2580
ccctcggaac catcagggcc aggtgcacct gcggggaacg tccccgagtg tgtgagcaat   2640
gccgcactga tacaggagtg gacacccgaa tctggcacca caatctcccc gagatcccag   2700
aataatgaag aagggggaga ccattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctgg tgaagataat aatgaagtag ctacagctca acttacctgc caaccccatg   3360
ccagtcgacc caactagcgt acacaaccta aatccattat aaaaaactta ggaaccaggt   3420
ccacacactc gagtcgcgcg tggccaccat gtgtcctcag aagctaacca tctcctggtt   3480
tgccatcgtt ttgctggtgt ccccactcat ggccatgtgg gagctggaga aagacgttta   3540
tgttgtagag gtggactgga ctcccgatgc ccctggagaa acagtgaacc tcacctgtga   3600
cacgcctgaa gaagatgaca tcacctggac ctcagaccag agacatggag tcataggctc   3660
tggaaagacc ctgaccatca ctgtcaaaga gtttctagat gctggccagt acacctgcca   3720
caaaggaggc gagactctga gccactcaca tctgctgctc cacaagaagg aaaatggaat   3780
ttggtccact gaaattttaa aaaatttcaa aaacaagact ttcctgaagt gtgaagcacc   3840
aaattactcc ggacggttca cgtgctcatg gctggtgcaa agaaacatgg acttgaagtt   3900
caacatcaag agcagtagca gttcccctga ctctcgggca gtgacatgtg gaatggcgtc   3960
tctgtctgca gagaaggtca cactggacca aagggactat gagaagtatt cagtgtcctg   4020
ccaggaggat gtcacctgcc caactgccga ggagaccctg cccattgaac tggcgttgga   4080
agcacggcag cagaataaat atgagaacta cagcaccagc ttcttcatca gggacatcat   4140
caaaccagac ccgcccaaga acttgcagat gaagcctttg aagaactcac aggtggaggt   4200
cagctgggag taccctgact cctggagcac tccccattcc tacttctccc tcaagttctt   4260
tgttcgaatc cagcgcaaga aagaaaagat gaaggagaca gaggaggggt gtaaccagaa   4320
aggtgcgttc ctcgtagaga agacatctac cgaagtccaa tgcaaaggcg ggaatgtctg   4380
cgtgcaagct caggatcgct attacaattc ctcgtgcagc aagtgggcat gtgttccctg   4440
cagggtccga tccggtggcg gtggctcggg cggtggtggg tcgggtggcg gcggatccag   4500
ggtcattcca gtctctggac ctgccaggtg tcttagccag tcccgaaacc tgctgaagac   4560
cacagatgac atggtgaaga cggccagaga aaaactgaaa cattattcct gcactgctga   4620
agacatcgat catgaagaca tcacacggga ccaaaccagc acattgaaga cctgtttacc   4680
actggaacta cacaagaacg agagttgcct ggctactaga gagacttctt ccacaacaag   4740
```

```
agggagctgc ctgcccccac agaagacgtc tttgatgatg accctgtgcc ttggtagcat   4800
ctatgaggac ttgaagatgt accagacaga gttccaggcc atcaacgcag cacttcagaa   4860
tcacaaccat cagcagatca ttctagacaa gggcatgctg gtggccatcg atgagctgat   4920
gcagtctctg aatcataatg gcgagactct gcgccagaaa cctcctgtgg gagaagcaga   4980
cccttacaga gtgaaaatga agctctgcat cctgcttcac gccttcagca cccgcgtcgt   5040
gaccatcaac agggtgatgg gctatctgag ctccgcctga taatagcgcg cgtcgtacga   5100
tgacgtccta gtacaaccta aatccattat aaaaaactta ggagcaaagt gattgcctcc   5160
caagttccac aatgacagag atctacgact tcgacaagtc ggcatgggac atcaaagggt   5220
cgatcgctcc gatacaaccc accacctaca gtgatggcag gctggtgccc caggtcagag   5280
tcatagatcc tggtctaggc gacaggaagg atgaatgctt tatgtacatg tttctgctgg   5340
gggttgttga ggacagcgat tccctagggc ctccaatcgg gcgagcattt gggtccctgc   5400
ccttaggtgt tggcagatcc acagcaaagc ccgaaaaact cctcaaagag gccactgagc   5460
ttgacatagt tgttagacgt acagcagggc tcaatgaaaa actggtgttc tacaacaaca   5520
ccccactaac tctcctcaca ccttggagaa aggtcctaac aacagggagt gtcttcaacg   5580
caaaccaagt gtgcaatgcg gttaatctga taccgctcga taccccgcag aggttccgtg   5640
ttgtttatat gagcatcacc cgtctttcgg ataacgggta ttacaccgtt cctggaagaa   5700
tgctggaatt cagatcggtc aatgcagtgg ccttcaacct gctggtgacc cttaggattg   5760
acaaggcgat aggccctggg aagatcatcg acaatacaga gcaacttcct gaggcaacat   5820
ttatggtcca catcgggaac ttcaggagaa agaagagtga agtctactct gccgattatt   5880
gcaaaatgaa aatcgaaaag atgggcctgg tttttgcact tggtgggata gggggcacca   5940
gtcttcacat tagaagcaca ggcaaaatga gcaagactct ccatgcacaa ctcgggttca   6000
agaagacctt atgttacccg ctgatggata tcaatgaaga ccttaatcga ttactctgga   6060
ggagcagatg caagatagta agaatccagg cagttttgca gccatcagtt cctcaagaat   6120
tccgcattta cgacgacgtg atcataaatg atgaccaagg actattcaaa gttctgtaga   6180
ccgtagtgcc cagcaatgcc cgaaaacgac ccccctcaca atgacagcca gaaggcccgg   6240
acaaaaaagc cccctccgaa agactccacg gaccaagcga gaggccagcc agcagccgac   6300
ggcaagcgcg aacaccaggc ggccccagca cagaacagcc ctgacacaag gccaccacca   6360
gccaccccaa tctgcatcct cctcgtggga cccccgagga ccaaccccca aggctgcccc   6420
cgatccaaac caccaaccgc atccccacca cccccgggaa agaaaccccc agcaattgga   6480
aggcccctcc ccctcttcct caacacaaga actccacaac cgaaccgcac aagcgaccga   6540
ggtgacccaa ccgcaggcat ccgactccct agacagatcc tctctccccg gcaaactaaa   6600
caaaacttag ggccaaggaa catacacacc caacagaacc cagaccccgg cccacggcgc   6660
cgcgccccca acccccgaca accagaggga gcccccaacc aatcccgccg gctcccccgg   6720
tgcccacagg cagggacacc aacccccgaa cagacccagc acccaaccat cgacaatcca   6780
agacgggggg gcccccccaa aaaaaggccc ccaggggccg acagccagca ccgcgaggaa   6840
gcccacccac cccacacacg accacggcaa ccaaaccaga acccagacca ccctgggcca   6900
ccagctccca gactcggcca tcaccccgca gaaaggaaag gccacaaccc gcgcaccccca  6960
gccccgatcc ggcggggagc cacccaaccc gaaccagcac ccaagagcga tccccgaagg   7020
acccccgaac cgcaaaggac atcagtatcc cacagcctct ccaagtcccc cggtctcctc   7080
```

-continued

```
ctcttctcga agggaccaaa agatcaatcc accacacccg acgacactca actccccacc   7140
cctaaaggag acaccgggaa tcccagaatc aagactcatc caatgtccat catgggtctc   7200
aaggtgaacg tctctgccat attcatggca gtactgttaa ctctccaaac acccaccggt   7260
caaatccatt ggggcaatct ctctaagata ggggtggtag gaataggaag tgcaagctac   7320
aaagttatga ctcgttccag ccatcaatca ttagtcataa aattaatgcc caatataact   7380
ctcctcaata actgcacgag ggtagagatt gcagaataca ggagactact gagaacagtt   7440
ttggaaccaa ttagagatgc acttaatgca gtgacccaga atataagacc ggttcagagt   7500
gtagcttcaa gtaggagaca caagagattt gcgggagtag tcctggcagg tgcggcccta   7560
ggcgttgcca cagctgctca gataacagcc ggcattgcac ttcaccagtc catgctgaac   7620
tctcaagcca tcgacaatct gagagcgagc ctggaaacta ctaatcaggc aattgaggca   7680
atcagacaag cagggcagga gatgatattg gctgttcagg gtgtccaaga ctacatcaat   7740
aatgagctga taccgtctat gaaccaacta tcttgtgatt taatcggcca gaagctcggg   7800
ctcaaattgc tcagatacta tacagaaatc ctgtcattat ttggccccag cttacgggac   7860
cccatatctg cggagatatc tatccaggct ttgagctatg cgcttggagg agacatcaat   7920
aaggtgttag aaaagctcgg atacagtgga ggtgatttac tgggcatctt agagagcaga   7980
ggaataaagg cccggataac tcacgtcgac acagagtcct acttcattgt cctcagtata   8040
gcctatccga cgctgtccga gattaagggg gtgattgtcc accggctaga gggggtctcg   8100
tacaacatag gctctcaaga gtggtatacc actgtgccca agtatgttgc aacccaaggg   8160
taccttatct cgaattttga tgagtcatcg tgtactttca tgccagaggg gactgtgtgc   8220
agccaaaatg ccttgtaccc gatgagtcct ctgctccaag aatgcctccg gggtccacc    8280
aagtcctgtg ctcgtacact cgtatccggg tcttttggga accggttcat tttatcacaa   8340
gggaacctaa tagccaattg tgcatcaatc ctttgcaagt gttacacaac aggaacgatc   8400
attaatcaag accctgacaa gatcctaaca tacattgctg ccgatcactg cccggtagtc   8460
gaggtgaacg gcgtgaccat ccaagtcggg agcaggaggt atccagacgc tgtgtacttg   8520
cacagaattg acctcggtcc tcccatatca ttggagaggt tggacgtagg gacaaatctg   8580
gggaatgcaa ttgctaagtt ggaggatgcc aaggaattgt tggagtcatc ggaccagata   8640
ttgaggagta tgaaaggttt atcgagcact agcatagtct acatcctgat tgcagtgtgt   8700
cttggagggt tgatagggat ccccgcttta atatgttgct gcagggggcg ttgtaacaaa   8760
aagggagaac aagttggtat gtcaagacca ggcctaaagc ctgatcttac gggaacatca   8820
aaatcctatg taaggtcgct ctgatcctct acaactcttg aaacacaaat gtcccacaag   8880
tctcctcttc gtcatcaagc aaccaccgca cccagcatca agcccacctg aaattatctc   8940
cggtttccct ctggccgaac aatatcggta gttaattaaa acttagggtg caagatcatc   9000
cacaatgtca ccacaacgag accggataaa tgccttctac aaagataacc cccatcccaa   9060
gggaagtagg atagtcatta acagagaaca tcttatgatt gatagacctt atgttttgct   9120
ggctgttctg tttgtcatgt ttctgagctt gatcgggttg ctagccattg caggcattag   9180
acttcatcgg gcagccatct acaccgcaga gatccataaa agcctcagca ccaatctaga   9240
tgtaactaac tcaatcgagc atcaggtcaa ggacgtgctg acaccactct tcaaaatcat   9300
cggtgatgaa gtgggcctga ggacacctca gagattcact gacctagtga aattcatctc   9360
tgacaagatt aaattcctta atccggatag ggagtacgac ttcagagatc tcacttggtg   9420
tatcaacccg ccagagagaa tcaaattgga ttatgatcaa tactgtgcag atgtggctgc   9480
```

tgaagagctc atgaatgcat tggtgaactc aactctactg gagaccagaa caaccaatca 9540
gttcctagct gtctcaaagg gaaactgctc agggcccact acaatcagag gtcaattctc 9600
aaacatgtcg ctgtccctgt tagacttgta tttaggtcga ggttacaatg tgtcatctat 9660
agtcactatg acatcccagg gaatgtatgg gggaacttac ctagtggaaa agcctaatct 9720
gagcagcaaa aggtcagagt tgtcacaact gagcatgtac cgagtgtttg aagtaggtgt 9780
tatcagaaat ccgggtttgg gggctccggt gttccatatg acaaactatc ttgagcaacc 9840
agtcagtaat gatctcagca actgtatggt ggctttgggg gagctcaaac tcgcagccct 9900
ttgtcacggg gaagattcta tcacaattcc ctatcaggga tcagggaaag gtgtcagctt 9960
ccagctcgtc aagctaggtg tctggaaatc cccaaccgac atgcaatcct gggtcccctt 10020
atcaacggat gatccagtga tagacaggct ttacctctca tctcacagag gtgttatcgc 10080
tgacaaccaa gcaaaatggg ctgtcccgac aacacgaaca gatgacaagt tgcgaatgga 10140
gacatgcttc caacaggcgt gtaagggtaa aatccaagca ctctgcgaga atcccgagtg 10200
ggcaccattg aaggataaca ggattccttc atacggggtc ttgtctgttg atctgagtct 10260
gacagttgag cttaaaatca aaattgcttc gggattcggg ccattgatca cacacggttc 10320
agggatggac ctatacaaat ccaaccacaa caatgtgtat tggctgacta tcccgccaat 10380
gaagaaccta gccttaggtg taatcaacac attggagtgg ataccgagat tcaaggttag 10440
tccctacctc ttcactgtcc caattaagga agcaggcgga gactgccatg ccccaacata 10500
cctacctgcg gaggtggatg gtgatgtcaa actcagttcc aatctggtga ttctacctgg 10560
tcaagatctc caatatgttt tggcaaccta cgatacttcc agggttgaac atgctgtggt 10620
ttattacgtt tacagcccaa gccgctcatt ttcttacttt tatcctttta ggttgcctat 10680
aaagggggtc cccatcgaat tacaagtgga atgcttcaca tgggaccaaa aactctggtg 10740
ccgtcacttc tgtgtgcttg cggactcaga atctggtgga catatcactc actctgggat 10800
ggtgggcatg ggagtcagct gcacagtcac ccgggaagat ggaaccaatc gcagataggg 10860
ctgctagtga accaatcaca tgatgtcacc cagacatcag gcatacccac tagtgtgaaa 10920
tagacatcag aattaagaaa aacgtagggt ccaagtggtt ccccgttatg gactcgctat 10980
ctgtcaacca gatcttatac cctgaagttc acctagatag cccgatagtt accaataaga 11040
tagtagccat cctggagtat gctcgagtcc ctcacgctta cagcctggag gaccctacac 11100
tgtgtcagaa catcaagcac cgcctaaaaa acggattttc caaccaaatg attataaaca 11160
atgtggaagt tgggaatgtc atcaagtcca agcttaggag ttatccggcc cactctcata 11220
ttccatatcc aaattgtaat caggatttat ttaacataga agacaaagag tcaacgagga 11280
agatccgtga actcctcaaa aaggggaatt cgctgtactc caaagtcagt gataaggttt 11340
tccaatgctt aagggacact aactcacggc ttggcctagg ctccgaattg agggaggaca 11400
tcaaggagaa agttattaac ttgggagttt acatgcacag ctcccagtgg tttgagccct 11460
ttctgttttg gtttacagtc aagactgaga tgaggtcagt gattaaatca caaacccata 11520
cttgccatag gaggagacac acacctgtat tcttcactgg tagttcagtt gagttgctaa 11580
tctctcgtga ccttgttgct ataatcagta aagagtctca acatgtatat tacctgacat 11640
ttgaactggt tttgatgtat tgtgatgtca tagaggggag gttaatgaca gagaccgcta 11700
tgactattga tgctaggtat acagagcttc taggaagagt cagatacatg tggaaactga 11760
tagatggttt cttccctgca ctcgggaatc caacttatca aattgtagcc atgctggagc 11820

-continued

```
ctctttcact tgcttacctg cagctgaggg atataacagt agaactcaga ggtgctttcc  11880
ttaaccactg ctttactgaa atacatgatg ttcttgacca aaacgggttt tctgatgaag  11940
gtacttatca tgagttaatt gaagctctag attacatttt cataactgat gacatacatc  12000
tgacagggga gattttctca tttttcagaa gtttcggcca ccccagactt gaagcagtaa  12060
cggctgctga aaatgttagg aaatacatga atcagcctaa agtcattgtg tatgagactc  12120
tgatgaaagg tcatgccata ttttgtggaa tcataatcaa cggctatcgt gacaggcacg  12180
gaggcagttg gccaccgctg accctccccc tgcatgctgc agacacaatc cggaatgctc  12240
aagcttcagg tgatgggtta acacatgagc agtgcgttga taactggaaa tcttttgctg  12300
gagtgaaatt tggctgcttt atgcctctta gcctggatag tgatctgaca atgtacctaa  12360
aggacaaggc acttgctgct ctccaaaggg aatgggattc agtttacccg aaagagttcc  12420
tgcgttacga ccctcccaag ggaaccgggt cacggaggct tgtagatgtt ttccttaatg  12480
attcgagctt tgacccatat gatgtgataa tgtatgttgt aagtggagct tacctccatg  12540
accctgagtt caacctgtct tacagcctga aagaaaagga gatcaaggaa acaggtagac  12600
tttttgctaa aatgacttac aaaatgaggg catgccaagt gattgctgaa aatctaatct  12660
caaacgggat tggcaaatat tttaaggaca atgggatggc caaggatgag cacgatttga  12720
ctaaggcact ccacactcta gctgtctcag gagtccccaa agatctcaaa gaaagtcaca  12780
ggggggggcc agtcttaaaa acctactccc gaagcccagt ccacacaagt accaggaacg  12840
tgagagcagc aaaagggttt atagggttcc ctcaagtaat tcggcaggac caagacactg  12900
atcatccgga gaatatggaa gcttacgaga cagtcagtgc atttatcacg actgatctca  12960
agaagtactg ccttaattgg agatatgaga ccatcagctt gtttgcacag aggctaaatg  13020
agatttacgg attgccctca tttttccagt ggctgcataa gaggcttgag acctctgtcc  13080
tgtatgtaag tgaccctcat tgcccccccg accttgacgc ccatatcccg ttatataaag  13140
tccccaatga tcaaatcttc attaagtacc ctatgggagg tatagaaggg tattgtcaga  13200
agctgtggac catcagcacc attccctatc tatacctggc tgcttatgag agcggagtaa  13260
ggattgcttc gttagtgcaa ggggacaatc agaccatagc cgtaacaaaa agggtaccca  13320
gcacatggcc ctacaacctt aagaaacggg aagctgctag agtaactaga gattactttg  13380
taattcttag gcaaaggcta catgatattg gccatcacct caaggcaaat gagacaattg  13440
tttcatcaca ttttttttgtc tattcaaaag gaatatatta tgatgggcta cttgtgtccc  13500
aatcactcaa gagcatcgca agatgtgtat tctggtcaga gactatagtt gatgaaacaa  13560
gggcagcatg cagtaatatt gctacaacaa tggctaaaag catcgagaga ggttatgacc  13620
gttaccttgc atattccctg aacgtcctaa aagtgataca gcaaattctg atctctcttg  13680
gcttcacaat caattcaacc atgacccggg atgtagtcat acccctcctc acaaacaacg  13740
acctcttaat aaggatggca ctgttgcccg ctcctattgg ggggatgaat tatctgaata  13800
tgagcaggct gtttgtcaga aacatcggtg atccagtaac atcatcaatt gctgatctca  13860
agagaatgat tctcgcctca ctaatgcctg aagagaccct ccatcaggta atgacacaac  13920
aaccggggga ctcttcattc ctagactggg ctagcgaccc ttactcagca aatcttgtat  13980
gtgtccagag catcactaga ctcctcaaga acataactgc aaggtttgtc ctgatccata  14040
gtccaaaccc aatgttaaaa ggattattcc atgatgacag taaagaagag gacgagggac  14100
tggcggcatt cctcatggac aggcatatta tagtacctag ggcagctcat gaaatcctgg  14160
atcatagtgt cacaggggca agagagtcta ttgcaggcat gctggatacc acaaaaggct  14220
```

-continued tgattcgagc cagcatgagg aagggggggtt taacctctcg agtgataacc agattgtcca 14280
attatgacta tgaacaattc agagcaggga tggtgctatt gacaggaaga aagagaaatg 14340
tcctcattga caaagagtca tgttcagtgc agctggcgag agctctaaga agccatatgt 14400
gggcgaggct agctcgagga cggcctattt acggccttga ggtccctgat gtactagaat 14460
ctatgcgagg ccaccttatt cggcgtcatg agacatgtgt catctgcgag tgtggatcag 14520
tcaactacgg atggtttttt gtcccctcgg gttgccaact ggatgatatt gacaaggaaa 14580
catcatcctt gagagtccca tatattggtt ctaccactga tgagagaaca gacatgaagc 14640
ttgccttcgt aagagcccca agtcgatcct tgcgatctgc tgttagaata gcaacagtgt 14700
actcatgggc ttacggtgat gatgatagct cttggaacga agcctggttg ttggctaggc 14760
aaagggccaa tgtgagcctg gaggagctaa gggtgatcac tcccatctca acttcgacta 14820
atttagcgca taggttgagg gatcgtagca ctcaagtgaa atactcaggt acatcccttg 14880
tccgagtggc gaggtatacc acaatctcca acgacaatct ctcatttgtc atatcagata 14940
agaaggttga tactaacttt atataccaac aaggaatgct tctagggttg ggtgttttag 15000
aaacattgtt tcgactcgag aaagataccg gatcatctaa cacggtatta catcttcacg 15060
tcgaaacaga ttgttgcgtg atcccgatga tagatcatcc caggataccc agctcccgca 15120
agctagagct gagggcagag ctatgtacca acccattgat atatgataat gcacctttaa 15180
ttgacagaga tgcaacaagg ctatacaccc agagccatag gaggcacctt gtggaatttg 15240
ttacatggtc cacaccccaa ctatatcaca ttttagctaa gtccacagca ctatctatga 15300
ttgacctggt aacaaaattt gagaaggacc atatgaatga aatttcagct ctcatagggg 15360
atgacgatat caatagtttc ataactgagt ttctgctcat agagccaaga ttattcacta 15420
tctacttggg ccagtgtgcg gccatcaatt gggcatttga tgtacattat catagaccat 15480
cagggaaata tcagatgggt gagctgttgt catcgttcct ttctagaatg agcaaaggag 15540
tgtttaaggt gcttgtcaat gctctaagcc acccaaagat ctacaagaaa ttctggcatt 15600
gtggtattat agagcctatc catggtcctt cacttgatgc tcaaaacttg cacacaactg 15660
tgtgcaacat ggtttacaca tgctatatga cctacctcga cctgttgttg aatgaagagt 15720
tagaagagtt cacatttctc ttgtgtgaaa gcgacgagga tgtagtaccg gacagattcg 15780
acaacatcca ggcaaaacac ttatgtgttc tggcagattt gtactgtcaa ccagggacct 15840
gcccaccaat tcaaggtcta agaccggtag agaaatgtgc agttctaacc gaccatatca 15900
aggcagaggc tatgttatct ccagcaggat cttcgtggaa cataaatcca attattgtag 15960
accattactc atgctccctg acttatctcc ggcgaggatc gatcaaacag ataagattga 16020
gagttgatcc aggattcatt ttcgacgccc tcgctgaggt aaatgtcagt cagccaaaga 16080
tcggcagcaa caacatctca aatatgagca tcaaggcttt cagacccccca cacgatgatg 16140 ttgcaaaatt gctcaaagat atcaacacaa gcaagcacaa tcttcccatt tcagggggca 16200
atctcgccaa ttatgaaatc catgctttcc gcagaatcgg gttgaactca tctgcttgct 16260
acaaagctgt tgagatatca acattaatta ggagatgcct tgagccaggg gaggacggct 16320
tgttcttggg tgagggatcg ggttctatgt tgatcactta taaggagata cttaaactaa 16380
gcaagtgctt ctataatagt ggggtttccg ccaattctag atctggtcaa agggaattag 16440
caccctatcc ctccgaagtt ggccttgtcg aacacagaat gggagtaggt aatattgtca 16500
aagtgctctt taacgggagg cccgaagtca cgtgggtagg cagtgtagat tgcttcaatt 16560

```
tcatagttag taatatccct acctctagtg tggggtttat ccattcagat atagagacct  16620
tgcctgacaa agatactata gagaagctag aggaattggc agccatctta tcgatggctc  16680
tgctcctggg caaaatagga tcaatactgg tgattaagct tatgcctttc agcggggatt  16740
ttgttcaggg atttataagt tatgtagggt ctcattatag agaagtgaac cttgtatacc  16800
ctagatacag caacttcatc tctactgaat cttatttggt tatgacagat ctcaaggcta  16860
accggctaat gaatcctgaa aagattaagc agcagataat tgaatcatct gtgaggactt  16920
cacctggact tataggtcac atcctatcca ttaagcaact aagctgcata caagcaattg  16980
tgggagacgc agttagtaga ggtgatatca atcctactct gaaaaaactt acacctatag  17040
agcaggtgct gatcaattgc gggttggcaa ttaacggacc taagctgtgc aaagaattga  17100
tccaccatga tgttgcctca gggcaagatg gattgcttaa ttctatactc atcctctaca  17160
gggagttggc aagattcaaa gacaaccaaa gaagtcaaca agggatgttc cacgcttacc  17220
ccgtattggt aagtagcagg caacgagaac ttatatctag gatcacccgc aaattctggg  17280
ggcacattct tctttactcc gggaacaaaa agttgataaa taagtttatc cagaatctca  17340
agtccggcta tctgatacta gacttacacc agaatatctt cgttaagaat ctatccaagt  17400
cagagaaaca gattattatg acggggggtt tgaaacgtga gtgggttttt aaggtaacag  17460
tcaaggagac caaagaatgg tataagttag tcggatacag tgccctgatt aaggactaat  17520
tggttgaact ccggaaccct aatcctgccc taggtggtta ggcattattt gcaatatatt  17580
aaagaaaact ttgaaaatac gaagtttcta ttcccagctt tgtctggt              17628
```

<210> SEQ ID NO 15
<211> LENGTH: 17571
<212> TYPE: DNA
<213> ORGANISM: Artificial
<220> FEATURE:
<223> OTHER INFORMATION: artificial polynucleotide encoding MV MeVac_H_FhIL-12

<400> SEQUENCE: 15

```
accaaacaaa gttgggtaag gatagttcaa tcaatgatca tcttctagtg cacttaggat     60
tcaagatcct attatcaggg acaagagcag gattagggat atccgagatg gccacacttt    120
taaggagctt agcattgttc aaaagaaaca aggacaaacc acccattaca tcaggatccg    180
gtggagccat cagaggaatc aaacacatta ttatagtacc aatccctgga gattcctcaa    240
ttaccactcg atccagactt ctggaccggt tggtgaggtt aattggaaac ccggatgtga    300
gcgggcccaa actaacaggg gcactaatag gtatattatc cttatttgtg gagtctccag    360
gtcaattgat tcagaggatc accgatgacc ctgacgttag cataaggctg ttagaggttg    420
tccagagtga ccagtcacaa tctggcctta ccttcgcatc aagaggtacc aacatggagg    480
atgaggcgga ccaatacttt tcacatgatg atccaattag tagtgatcaa tccaggttcg    540
gatggttcgg gaacaaggaa atctcagata ttgaagtgca agaccctgag ggattcaaca    600
tgattctggg taccatccta gcccaaattt gggtcttgct cgcaaaggcg gttacggccc    660
cagacacggc agctgattcg gagctaagaa ggtggataaa gtacacccaa caaagaaggg    720
tagttggtga atttagattg gagagaaaat ggttggatgt ggtgaggaac aggattgccg    780
aggacctctc cttacgccga ttcatggtcg ctctaatcct ggatatcaag agaacacccg    840
gaaacaaacc caggattgct gaaatgatat gtgacattga tacatatatc gtagaggcag    900
gattagccag ttttatcctg actattaagt ttgggataga aactatgtat cctgctcttg    960
```

-continued

```
gactgcatga atttgctggt gagttatcca cacttgagtc cttgatgaac ctttaccagc   1020
aaatgggga aactgcaccc tacatggtaa tcctggagaa ctcaattcag aacaagttca   1080
gtgcaggatc ataccctctg ctctggagct atgccatggg agtaggagtg gaacttgaaa   1140
actccatggg aggtttgaac tttggccgat cttactttga tccagcatat tttagattag   1200
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc aacggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actaggtgcg agaggccgag ggccagaaca acatccgcct accatccatc attgttataa   1740
aaaacttagg aaccaggtcc acacagccgc cagcccatca accatccact cccacgattg   1800
gagccaatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggttacag tgttattacg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc tttattgaca ggtggtgcaa cccaatgtgc tcgaaagtca   2580
ccctcggaac catcagggcc aggtgcacct gcggggaatg tccccgagtg tgtgagcaat   2640
gccgcactga tacaggagtg gacacccgaa tctggtacca caatctcccc gagatcccag   2700
aataatgaag aagggggaga ctattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctga tgaagataat aatgaagtag ctacagctca acttacctgc caaccccatg   3360
```

-continued

```
ccagtcgacc caactagtac aacctaaatc cattataaaa aacttaggag caaagtgatt   3420
gcctcccaag gtccacaatg acagagacct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
tgctgggggt tgttgaggac agcgattccc tagggcctcc aatcgggcga gcatttgggt   3660
tcctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cgggtattac accgttccta   3960
gaagaatgct ggaattcaga tcggtcaatg cagtggcctt caacctgctg gtgaccctta   4020
ggattgacaa ggcgataggc cctgggaaga tcatcgacaa tacagagcaa cttcctgagg   4080
caacatttat ggtccacatc gggaacttca ggagaaagaa gagtgaagtc tactctgccg   4140
attattgcaa aatgaaaatc gaaaagatgg gcctggtttt tgcacttggt gggatagggg   4200
gcaccagtct tcacattaga agcacaggca aaatgagcaa gactctccat gcacaactcg   4260
ggttcaagaa gaccttatgt tacccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa aacgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680
tgcccccgat ccaaaccacc aaccgcatcc ccaccacccc cgggaaagaa acccccagca   4740
attggaaggc ccctccccct cttcctcaac acaagaactc cacaaccgaa ccgcacaagc   4800
gaccgaggtg acccaaccgc aggcatccga ctccctagac agatcctctc tccccggcaa   4860
actaaacaaa acttagggcc aaggaacata cacacccaac agaacccaga ccccggccca   4920
cggcgccgcg cccccaaccc ccgacaacca gagggagccc ccaaccaatc ccgccggctc   4980
ccccggtgcc cacaggcagg gacaccaacc cccgaacaga cccagcaccc aaccatcgac   5040
aatccaagac ggggggggccc ccccaaaaaa aggcccccag gggccgacag ccagcaccgc   5100
gaggaagccc acccacccca cacacgacca cggcaaccaa accagaaccc agaccaccct   5160
gggccaccag ctcccagact cggccatcac cccgcagaaa ggaaaggcca caacccgcgc   5220
accccagccc cgatccggcg gggagccacc caacccgaac cagcacccaa gagcgatccc   5280
cgaaggaccc ccgaaccgca aaggacatca gtatcccaca gcctctccaa gtcccccggt   5340
ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
```

-continued

```
acagttttgg aaccaattag agatgcactt aatgcaatga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
gagacaatca gacaagcagg gcaggagatg atattggctg ttcagggtgt ccaagactac   6000
atcaataatg agctgatacc gtctatgaac caactatctt gtgatttaat cggccagaag   6060
ctcgggctca aattgctcag atactataca gaaatcctgt cattatttgg ccccagttta   6120
cgggacccca tatctgcgga gatatctatc caggctttga gctatgcgct tggaggagac   6180
atcaataagg tgttagaaaa gctcggatac agtggaggtg atttactggg catcttagag   6240
agcggaggaa taaaggcccg gataactcac gtcgacacag agtcctactt cattgtcctc   6300
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tacaccaagt cctgtgctcg tacactcgta tccgggtctt ttgggaaccg gttcatttta   6600
tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag gggcgttgt    7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggc ttccctctgg ccgaacaata tcggtagtta atcaaaactt agggtgcaag   7260
atcatccaca atgtcaccac aacgagaccg gataaatgcc ttctacaaag ataaccccca   7320
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
aatctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatggggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
```

-continued

```
gcaaccagtc agtaatgatc tcagcaactg tatggtggct ttgggggagc tcaaactcgc   8160
agccctttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aatcaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcgaagact gccatgcccc   8760
aacataccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcattttct tacttttatc cttttaggtt   8940
gcctataaag ggggtcccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120
atagggctgc tagtgaacca atcacatgat gtcacccaga catcaggcat acccactagt   9180
catccatcat tgttataaaa aacttaggaa ccaggtccac acagctcgag tcgcgcgtgc   9240
caccatgtgt caccagcagt tggtcatctc ttggttttcc ctggtttttc tggcatctcc   9300
cctcgtggcc atatgggaac tgaagaaaga tgtttatgtc gtagaattgg attggtatcc   9360
ggatgcccct ggagaaatgg tggtcctcac ctgtgacacc cctgaagaag atggtatcac   9420
ctggaccttg gaccagagca gtgaggtctt aggctctggc aaaaccctga ccatccaagt   9480
caaagagttt ggagatgctg gccagtacac ctgtcacaaa ggaggcgagg ttctaagcca   9540
ttcgctcctg ctgcttcaca aaaaggaaga tggaatttgg tccactgata ttttaaagga   9600
ccagaaagaa cccaaaaata agacctttct aagatgcgag gccaagaatt attctggacg   9660
tttcacctgc tggtggctga cgacaatcag tactgatttg acattcagtg tcaaaagcag   9720
cagaggctct tctgaccccc aaggggtgac gtgcggagct gctacactct ctgcagagag   9780
agtcagaggg gacaacaagg agtatgagta ctcagtggag tgccaggagg acagtgcctg   9840
cccagctgct gaggagagtc tgcccattga ggtcatggtg gatgccgttc acaagctcaa   9900
gtatgaaaac tacaccagca gcttcttcat cagggacatc atcaaacctg acccacccaa   9960
caacttgcag ctgaagccat taaagaattc tcggcaggtg gaggtcagct gggagtaccc  10020
tgacacctgg agtactccac attcctactt ctccctgaca ttctgcgttc aggtccaggg  10080
caagagcaag agagaaaaga aagatagagt cttcaccgac aagacctcag ccacggtcat  10140
ctgccgcaaa aatgccagca ttagcgtgcg ggcccaggac cgctactata gctcatcttg  10200
gagcgaatgg gcatctgtgc cctgcagtgg tggcggtggc ggcggatcta gaaacctccc  10260
cgtggccact ccagacccag gaatgttccc atgccttcac cactcccaaa acctgctgag  10320
ggccgtcagc aacatgctcc agaaggccag acaaactcta gaattttacc cttgcacttc  10380
tgaagagatt gatcatgaag atatcacaaa agataaaacc agcacagtgg aggcctgttt  10440
```

-continued

```
accattggaa ttaaccaaga atgagagttg cctaaattcc agagagacct ctttcataac  10500
taatgggagt tgcctggcct ccagaaagac ctcttttatg atggccctgt gccttagtag  10560
tatttatgaa gacttgaaga tgtaccaggt ggagttcaag accatgaatg caaagcttct  10620
gatggatcct aagaggcaga tctttctaga tcaaaacatg ctggcagtta ttgatgagct  10680
gatgcaggcc ctgaatttca acagtgagac tgtgccacaa aaatcctccc ttgaagaacc  10740
ggatttttat aaaactaaaa tcaagctctg catacttctt catgctttca gaattcgggc  10800
agtgactatt gatagagtga tgagctatct gaatgcttcc taggcgcgcg ttctagtgtg  10860
aaatagacat cagaattaag aaaaacgtag ggtccaagtg gttccccgtt atggactcgc  10920
tatctgtcaa ccagatctta taccctgaag ttcacctaga tagcccgata gttaccaata  10980
agatagtagc catcctggag tatgctcgag tccctcacgc ttacagcctg gaggacccta  11040
cactgtgtca gaacatcaag caccgcctaa aaaacggatt ttccaaccaa atgattataa  11100
acaatgtgga agttgggaat gtcatcaagt ccaagcttag gagttatccg gcccactctc  11160
atattccata tccaaattgt aatcaggatt tatttaacat agaagacaaa gagtcaacga  11220
ggaagatccg tgaactcctc aaaaagggga attcgctgta ctccaaagtc agtgataagg  11280
ttttccaatg cttaagggac actaactcac ggcttggcct aggctccgaa ttgagggagg  11340
acatcaagga gaaagttatt aacttgggag tttacatgca cagctcccag tggtttgagc  11400
cctttctgtt ttggtttaca gtcaagactg agatgaggtc agtgattaaa tcacaaaccc  11460
atacttgcca taggaggaga cacacacctg tattcttcac tggtagttca gttgagttgc  11520
taatctctcg tgaccttgtt gctataatca gtaaagagtc tcaacatgta tattacctga  11580
catttgaact ggttttgatg tattgtgatg tcatagaggg gaggttaatg acagagaccg  11640
ctatgactat tgatgctagg tatacagagc ttctaggaag agtcagatac atgtggaaac  11700
tgatagatgg tttcttccct gcactcggga atccaactta tcaaattgta gccatgctgg  11760
agcctctttc acttgcttac ctgcagctga gggatataac agtagaactc agaggtgctt  11820
tccttaacca ctgctttact gaaatacatg atgttcttga ccaaaacggg ttttctgatg  11880
aaggtactta tcatgagtta actgaagctc tagattacat tttcataact gatgacatac  11940
atctgacagg ggagattttc tcatttttca gaagtttcgg ccaccccaga cttgaagcag  12000
taacggctgc tgaaaatgtt aggaaataca tgaatcagcc taaagtcatt gtgtatgaga  12060
ctctgatgaa aggtcatgcc atattttgtg gaatcataat caacggctat cgtgacaggc  12120
acggaggcag ttggccaccg ctgaccctcc ccctgcatgc tgcagacaca atccggaatg  12180
ctcaagcttc aggtgaaggg ttaacacatg agcagtgcgt tgataactgg aaatcttttg  12240
ctggagtgaa atttggctgc tttatgcctc ttagcctgga tagtgatctg acaatgtacc  12300
taaaggacaa ggcacttgct gctctccaaa gggaatggga ttcagtttac ccgaaagagt  12360
tcctgcgtta cgaccctccc aagggaaccg ggtcacggag gcttgtagat gttttcctta  12420
atgattcgag ctttgaccca tatgatgtga taatgtatgt tgtaagtgga gcttacctcc  12480
atgaccctga gttcaacctg tcttacagcc tgaaagaaaa ggagatcaag gaaacaggta  12540
gactttttgc taaaatgact tacaaaatga gggcatgcca agtgattgct gaaaatctaa  12600
tctcaaacgg gattggcaaa tattttaagg acaatgggat ggccaaggat gagcacgatt  12660
tgactaaggc actccacact ctagctgtct caggagtccc caaagatctc aaagaaagtc  12720
acaggggggg gccagtctta aaaacctact cccgaagccc agtccacaca agtaccagga  12780
acgtgagagc agcaaaaggg tttataggt tccctcaagt aattcggcag gaccaagaca  12840
```

```
ctgatcatcc ggagaatatg gaagcttacg agacagtcag tgcatttatc acgactgatc  12900
tcaagaagta ctgccttaat tggagatatg agaccatcag cttgtttgca cagaggctaa  12960
atgagattta cggattgccc tcatttttcc agtggctgca taagaggctt gagacctctg  13020
tcctgtatgt aagtgaccct cattgccccc ccgaccttga cgcccatatc ccgttatata  13080
aagtccccaa tgatcaaatc ttcattaagt accctatggg aggtatagaa gggtattgtc  13140
agaagctgtg gaccatcagc accattccct atctatacct ggctgcttat gagagcggag  13200
taaggattgc ttcgttagtg caaggggaca atcagaccat agccgtaaca aaaagggtac  13260
ccagcacatg gccctacaac cttaagaaac gggaagctgc tagagtaact agagattact  13320
ttgtaattct taggcaaagg ctacatgata ttggccatca cctcaaggca aatgagacaa  13380
ttgtttcatc acattttttt gtctattcaa aaggaatata ttatgatggg ctacttgtgt  13440
cccaatcact caagagcatc gcaagatgtg tattctggtc agagactata gttgatgaaa  13500
caagggcagc atgcagtaat attgctacaa caatggctaa aagcatcgag agaggttatg  13560
accgttacct tgcatattcc ctgaacgtcc taaaagtgat acagcaaatt ctgatctctc  13620
ttggcttcac aatcaattca accatgaccc gggatgtagt catacccctc ctcacaaaca  13680
acgacctctt aataaggatg gcactgttgc ccgctcctat tggggggatg aattatctga  13740
atatgagcag gctgtttgtc agaaacatcg gtgatccagt aacatcatca attgctgatc  13800
tcaagagaat gattctcgcc tcactaatgc ctgaagagac cctccatcaa gtaatgacac  13860
aacaaccggg ggactcttca ttcctagact gggctagcga cccttactca gcaaatcttg  13920
tatgtgtcca gagcatcact agactcctca agaacataac tgcaaggttt gtcctgatcc  13980
atagtccaaa cccaatgtta aaaggattat tccatgatga cagtaaagaa gaggacgagg  14040
gactggcggc attcctcatg gacaggcata ttatagtacc tagggcagct catgaaatcc  14100
tggatcatag tgtcacaggg gcaagagagt ctattgcagg catgctggat accacaaaag  14160
gcttgattcg agccagcatg aggaaggggg ggttaacctc tcgagtgata accagattgt  14220
ccaattatga ctatgaacaa ttcagagcag ggatggtgct attgacagga agaaagagaa  14280
atgtcctcat tgacaaagag tcatgttcag tgcagctggc gagagctcta agaagccata  14340
tgtgggcgag gctagctcga ggacggccta tttacggcct tgaggtccct gatgtactag  14400
aatctatgcg aggccacctt attcggcgtc atgagacatg tgtcatctgc gagtgtggat  14460
cagtcaacta cggatggttt tttgtcccct cgggttgcca actggatgat attgacaagg  14520
aaacatcatc cttgagagtc ccatatattg gttctaccac tgatgagaga acagacatga  14580
agcttgcctt cgtaagagcc ccaagtcgat ccttgcgatc tgctgttaga atagcaacag  14640
tgtactcatg ggcttacggt gatgatgata gctcttggaa cgaagcctgg ttgttggcta  14700
ggcaaagggc caatgtgagc ctggaggagc taagggtgat cactcccatc tcaacttcga  14760
ctaatttagc gcataggttg agggatcgta gcactcaagt gaaatactca ggtacatccc  14820
ttgtccgagt ggcgaggtat accacaatct ccaacgacaa tctctcattt gtcatatcag  14880
ataagaaggt tgatactaac tttatatacc aacaaggaat gcttctaggg ttgggtgttt  14940
tagaaacatt gtttcgactc gagaaagata ccggatcatc taacacggta ttacatcttc  15000
acgtcgaaac agattgttgc gtgatcccga tgatagatca tcccaggata cccagctccc  15060
gcaagctaga gctgagggca gagctatgta ccaacccatt gatatatgat aatgcacctt  15120
taattgacag agatgcaaca aggctataca cccagagcca taggaggcac cttgtggaat  15180
```

-continued

```
ttgttacatg gtccacaccc caactatatc acattttagc taagtccaca gcactatcta  15240
tgattgacct ggtaacaaaa tttgagaagg accatatgaa tgaaatttca gctctcatag  15300
gggatgacga tatcaatagt ttcataactg agtttctgct catagagcca agattattca  15360
ctatctactt gggccagtgt gcggccatca attgggcatt tgatgtacat tatcatagac  15420
catcagggaa atatcagatg ggtgagctgt tgtcatcgtt cctttctaga atgagcaaag  15480
gagtgtttaa ggtgcttgtc aatgctctaa gccacccaaa gatctacaag aaattctggc  15540
attgtggtat tatagagcct atccatggtc cttcacttga tgctcaaaac ttgcacacaa  15600
ctgtgtgcaa catggtttac acatgctata tgacctacct cgacctgttg ttgaatgaag  15660
agttagaaga gttcacattt ctcttgtgtg aaagcgacga ggatgtagta ccggacagat  15720
tcgacaacat ccaggcaaaa cacttatgtg ttctggcaga tttgtactgt caaccaggga  15780
cctgcccacc aattcgaggt ctaagaccgg tagagaaatg tgcagttcta accgaccata  15840
tcaaggcaga ggctatgtta tctccagcag gatcttcgtg gaacataaat ccaattattg  15900
tagaccatta ctcatgctct ctgacttatc tccggcgagg atcgatcaaa cagataagat  15960
tgagagttga tccaggattc attttcgacg ccctcgctga ggtaaatgtc agtcagccaa  16020
agatcggcag caacaacatc tcaaatatga gcatcaaggc tttcagaccc ccacacgatg  16080
atgttgcaaa attgctcaaa gatatcaaca caagcaagca caatcttccc atttcagggg  16140
gcaatctcgc caattatgaa atccatgctt tccgcagaat cgggttgaac tcatctgctt  16200
gctacaaagc tgttgagata tcaacattaa ttaggagatg ccttgagcca ggggaggacg  16260
gcttgttctt gggtgaggga tcgggttcta tgttgatcac ttataaagag atacttaaac  16320
taaacaagtg cttctataat agtggggttt ccgccaattc tagatctggt caaagggaat  16380
tagcacccta tccctccgaa gttggccttg tcgaacacag aatgggagta ggtaatattg  16440
tcaaagtgct ctttaacggg aggcccgaag tcacgtgggt aggcagtgta gattgcttca  16500
atttcatagt tagtaatatc cctacctcta gtgtggggtt tatccattca gatatagaga  16560
ccttgcctga caaagatact atagagaagc tagaggaatt ggcagccatc ttatcgatgg  16620
ctctgctcct gggcaaaata ggatcaatac tggtgattaa gcttatgcct ttcagcgggg  16680
attttgttca gggatttata agttatgtag ggtctcatta tagagaagtg aaccttgtat  16740
accctagata cagcaacttc atctctactg aatcttattt ggttatgaca gatctcaagg  16800
ctaaccggct aatgaatcct gaaaagatta agcagcagat aattgaatca tctgtgagga  16860
cttcacctgg acttataggt cacatcctat ccattaagca actaagctgc atacaagcaa  16920
ttgtgggaga cgcagttagt agaggtgata tcaatcctac tctgaaaaaa cttacaccta  16980
tagagcaggt gctgatcaat tgcgggttgg caattaacgg acctaagctg tgcaaagaat  17040
tgatccacca tgatgttgcc tcagggcaag atggattgct taattctata ctcatcctct  17100
acagggagtt ggcaagattc aaagacaacc aaagaagtca acaagggatg ttccacgctt  17160
accccgtatt ggtaagtagc aggcaacgag aacttatatc taggatcacc cgcaaattct  17220
gggggcacat tcttctttac tccgggaaca aaaagttgat aaataagttt atccagaatc  17280
tcaagtccgg ctatctgata ctagacttac accagaatat cttcgttaag aatctatcca  17340
agtcagagaa acagattatt atgacggggg gtttgaaacg tgagtgggtt tttaaggtaa  17400
cagtcaagga gaccaaagaa tggtataagt tagtcggata cagtgccctg attaaggact  17460
aattggttga actccggaac cctaatcctg ccctaggtgg ttaggcatta tttgcaatat  17520
attaaagaaa actttgaaaa tacgaagttt ctattcccag ctttgtctgg t           17571
```

<210> SEQ ID NO 16
<211> LENGTH: 282
<212> TYPE: PRT
<213> ORGANISM: Artificial
<220> FEATURE:
<223> OTHER INFORMATION: artificial subsequence of IgG1 (Fc)

<400> SEQUENCE: 16

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Val Asp Glu Ala Lys Ser Cys Asp Lys Thr His Thr Cys
        35                  40                  45

Pro Pro Cys Pro Ala Pro Glu Leu Leu Gly Gly Pro Ser Val Phe Leu
    50                  55                  60

Phe Pro Pro Lys Pro Lys Asp Thr Leu Met Ile Ser Arg Thr Pro Glu
65                  70                  75                  80

Val Thr Cys Val Val Val Asp Val Ser His Glu Asp Pro Glu Val Lys
                85                  90                  95

Phe Asn Trp Tyr Val Asp Gly Val Glu Val His Asn Ala Lys Thr Lys
            100                 105                 110

Pro Arg Glu Glu Gln Tyr Asn Ser Thr Tyr Arg Val Val Ser Val Leu
        115                 120                 125

Thr Val Leu His Gln Asp Trp Leu Asn Gly Lys Glu Tyr Lys Cys Lys
    130                 135                 140

Val Ser Asn Lys Ala Leu Pro Ala Pro Ile Glu Lys Thr Ile Ser Lys
145                 150                 155                 160

Ala Lys Gly Gln Pro Arg Glu Pro Gln Val Tyr Thr Leu Pro Pro Ser
                165                 170                 175

Arg Asp Glu Leu Thr Lys Asn Gln Val Ser Leu Thr Cys Leu Val Lys
            180                 185                 190

Gly Phe Tyr Pro Ser Asp Ile Ala Val Glu Trp Glu Ser Asn Gly Gln
        195                 200                 205

Pro Glu Asn Asn Tyr Lys Thr Thr Pro Pro Val Leu Asp Ser Asp Gly
    210                 215                 220

Ser Phe Phe Leu Tyr Ser Lys Leu Thr Val Asp Lys Ser Arg Trp Gln
225                 230                 235                 240

Gln Gly Asn Val Phe Ser Cys Ser Val Met His Glu Ala Leu His Asn
                245                 250                 255

His Tyr Thr Gln Lys Ser Leu Ser Leu Ser Pro Gly Lys Val Asp Glu
            260                 265                 270

Gln Lys Leu Ile Ser Glu Glu Asp Leu Asn
        275                 280
```

<210> SEQ ID NO 17
<211> LENGTH: 852
<212> TYPE: DNA
<213> ORGANISM: Artificial
<220> FEATURE:
<223> OTHER INFORMATION: artificial sequence encoding IgG1-Fc

<400> SEQUENCE: 17

```
atggagacag acacactcct gctatgggta ctgctgctct gggttccagg ttccactggt      60

gactatccat atgatgttcc agattatgct ggggcccagc cggccgtcga cgaggccaaa     120
```

-continued

| | |
|---|---|
| tcttgtgaca aaactcacac atgcccaccg tgcccagcac ccgaactcct gggggaccg | 180 |
| tcagtcttcc tcttcccccc aaaacccaag gacaccctca tgatctcccg gacccctgag | 240 |
| gtcacatgcg tggtggtgga cgtgagccac gaagaccctg aggtcaagtt caactggtac | 300 |
| gtggacggcg tggaggtgca taatgccaag acaaagccgc gggaggagca gtacaacagc | 360 |
| acgtaccgtg tggtcagcgt cctcaccgtc ctgcaccagg actggctgaa tggcaaggag | 420 |
| tacaagtgca aggtctccaa caaagccctc ccagccccca tcgagaaaac catctccaaa | 480 |
| gccaaggggc agccccgaga accacaggtg tacaccctgc ccccatcccg ggatgagctg | 540 |
| accaagaacc aggtcagcct gacctgcctg gtcaaaggct tctatcccag cgacatcgcc | 600 |
| gtggagtggg agagcaatgg gcagccggag aacaactaca agaccacgcc tcccgtgctg | 660 |
| gactccgacg gctccttctt cctctacagc aagctcaccg tggacaagag caggtggcag | 720 |
| caggggaacg tcttctcatg ctccgtgatg catgaggctc tgcacaacca ctacacgcag | 780 |
| aagagcctct ccctgtctcc gggtaaagtc gacgaacaaa aactcatctc agaagaagat | 840 |
| ctgaattgat ag | 852 |